United States Patent
Ohsawa et al.

(10) Patent No.: US 9,412,956 B2
(45) Date of Patent: Aug. 9, 2016

(54) ORGANOMETALLIC IRIDIUM COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Nobuharu Ohsawa, Kanagawa (JP); Hideko Inoue, Kanagawa (JP); Satoshi Seo, Kanagawa (JP); Miki Kanamoto, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 14/482,536

(22) Filed: Sep. 10, 2014

(65) Prior Publication Data

US 2015/0073142 A1    Mar. 12, 2015

(30) Foreign Application Priority Data

Sep. 12, 2013    (JP) .................. 2013-189385

(51) Int. Cl.
| | | |
|---|---|---|
| C07D 239/26 | (2006.01) |
| C09K 11/06 | (2006.01) |
| C01G 55/00 | (2006.01) |
| H01L 51/50 | (2006.01) |
| H01L 51/52 | (2006.01) |
| H05B 33/14 | (2006.01) |
| H01L 51/00 | (2006.01) |

(52) U.S. Cl.
CPC ............ *H01L 51/0085* (2013.01); *C09K 11/06* (2013.01); *H05B 33/14* (2013.01); *C09K 2211/1007* (2013.01); *C09K 2211/1029* (2013.01); *C09K 2211/1044* (2013.01); *C09K 2211/185* (2013.01); *H01L 51/0059* (2013.01); *H01L 51/0072* (2013.01); *H01L 51/0074* (2013.01); *H01L 51/5016* (2013.01); *H01L 2251/5384* (2013.01)

(58) Field of Classification Search
CPC ...... C07D 239/26; C09K 11/06; C01G 55/00; H05B 33/14; H01L 51/5032; H01L 51/5064; H01L 51/0032; H01L 51/5296
USPC .............. 544/242; 423/22; 313/504
See application file for complete search history.

(56) References Cited

U.S. PATENT DOCUMENTS

| | | | |
|---|---|---|---|
| 6,097,147 A | 8/2000 | Baldo et al. |
| 6,830,828 B2 | 12/2004 | Thompson et al. |
| 6,902,830 B2 | 6/2005 | Thompson et al. |
| 6,974,639 B2 | 12/2005 | Tsuboyama et al. |
| 7,001,536 B2 | 2/2006 | Thompson et al. |
| 7,220,495 B2 | 5/2007 | Tsuboyama et al. |
| 7,291,406 B2 | 11/2007 | Thompson et al. |
| 7,354,662 B2 | 4/2008 | Tsuboyama et al. |
| 7,537,844 B2 | 5/2009 | Thompson et al. |
| 7,807,839 B2 | 10/2010 | Inoue et al. |
| 7,883,787 B2 | 2/2011 | Thompson et al. |
| 8,519,384 B2 | 8/2013 | Xia et al. |
| 8,653,553 B2 * | 2/2014 | Yamazaki et al. .............. 257/98 |
| 8,921,548 B2 * | 12/2014 | Inoue et al. ................... 544/242 |
| 2005/0221123 A1 | 10/2005 | Inoue et al. |
| 2007/0129545 A1 | 6/2007 | Inoue et al. |

(Continued)

FOREIGN PATENT DOCUMENTS

| | | |
|---|---|---|
| CN | 101525354 A | 9/2009 |
| CN | 101550167 A | 10/2009 |

(Continued)

OTHER PUBLICATIONS

Bredereck, H. et al. , "Formamide Reactions, VIII. A New Pyrimidine-Synthesis," *Chem. Ber.*, 1957, vol. 90 (1957), pp. 942-952.

(Continued)

*Primary Examiner* — Venkataraman Balasubramanian

(74) *Attorney, Agent, or Firm* — Husch Blackwell LLP

(57) ABSTRACT

An organometallic iridium complex has high emission efficiency and a long lifetime. The iridium complex includes the structure represented by Formula (G1). In the formula, Ar represents a substituted or unsubstituted arylene group having 6 to 13 carbon atoms. $R^1$ to $R^6$ independently represent any one of hydrogen and a substituted or unsubstituted alkyl group having 1 to 6 carbon atoms, and one of $R^2$ and $R^6$ represents the alkyl group. X represents a carbon atom or a nitrogen atom, and when X represents a carbon atom, hydrogen or an alkyl group having 1 to 6 carbon atoms is bonded to the carbon atom. A dihedral angle between a ring bonded to $R^1$ and a phenyl group bonded to $R^2$ to $R^6$ is 30° or more and 90° or less. An interior angle of the pyridine/pyrimidine ring facing $R^1$ is within a range of 118° to 122°.

(G1)

9 Claims, 16 Drawing Sheets

(56) References Cited

U.S. PATENT DOCUMENTS

| | | |
|---|---|---|
| 2007/0244320 A1 | 10/2007 | Inoue et al. |
| 2009/0015143 A1 | 1/2009 | Inoue et al. |
| 2009/0039776 A1 | 2/2009 | Yamada et al. |
| 2009/0184631 A1 | 7/2009 | Kim et al. |
| 2010/0102710 A1 | 4/2010 | Cho et al. |
| 2010/0105902 A1 | 4/2010 | Inoue et al. |
| 2011/0049496 A1 | 3/2011 | Fukuzaki |
| 2011/0057560 A1 | 3/2011 | Inoue et al. |
| 2011/0082296 A1 | 4/2011 | Inoue et al. |
| 2011/0112296 A1 | 5/2011 | Thompson et al. |
| 2011/0227049 A1 | 9/2011 | Xia et al. |
| 2012/0061707 A1 | 3/2012 | Seo et al. |
| 2012/0098417 A1* | 4/2012 | Inoue et al. ............ 313/504 |
| 2012/0208999 A1 | 8/2012 | Konno |
| 2013/0165653 A1* | 6/2013 | Inoue et al. ............ 544/225 |
| 2014/0021449 A1 | 1/2014 | Xia et al. |
| 2014/0135498 A1 | 5/2014 | Fukuzaki |
| 2014/0231755 A1 | 8/2014 | Xia et al. |
| 2014/0231756 A1 | 8/2014 | Alleyne et al. |
| 2015/0005496 A1 | 1/2015 | Inoue et al. |

FOREIGN PATENT DOCUMENTS

| | | |
|---|---|---|
| CN | 102232105 A | 11/2011 |
| CN | 103168043 A | 6/2013 |
| CN | 103254241 A | 8/2013 |
| CN | 103827119 A | 5/2014 |
| CN | 103864675 A | 6/2014 |
| DE | 112011103544 T5 | 8/2013 |
| EP | 2 066 150 A1 | 6/2009 |
| EP | 2 103 665 A1 | 9/2009 |
| EP | 2 769 982 A2 | 8/2014 |
| JP | 2003-109758 A | 4/2003 |
| JP | 2006-120905 A | 5/2006 |
| JP | 2007-137872 A | 6/2007 |
| JP | 2008-069221 A | 3/2008 |
| JP | 2009-185017 A | 8/2009 |
| JP | 2009-275030 A | 11/2009 |
| JP | 2010-185068 A | 8/2010 |
| JP | 2011-089103 A | 5/2011 |
| JP | 2012-502046 | 1/2012 |
| JP | 2012-149030 A | 8/2012 |
| JP | 2012-199562 A | 10/2012 |
| JP | 5045100 B2 | 10/2012 |
| JP | 2013-053158 A | 3/2013 |
| JP | 2013-147496 A | 8/2013 |
| JP | 2013-149880 A | 8/2013 |
| JP | 2014-162796 A | 9/2014 |
| KR | 2009-0054507 A | 6/2009 |
| KR | 2009-0100013 A | 9/2009 |
| KR | 2011-0065496 A | 6/2011 |
| KR | 2013-0011405 A | 1/2013 |
| KR | 2014-0001850 A | 1/2014 |
| KR | 2014-0012440 A | 2/2014 |
| KR | 2014-0012769 A | 2/2014 |
| TW | I231157 B | 4/2005 |
| TW | 200946639 | 11/2009 |
| TW | 200946643 | 11/2009 |
| TW | 201016665 | 5/2010 |
| TW | 201016666 | 5/2010 |
| TW | 201233767 | 8/2012 |
| TW | 201307336 | 2/2013 |
| TW | 201333019 | 8/2013 |
| TW | 201336969 | 9/2013 |
| TW | 201410686 | 3/2014 |
| WO | WO 2005/097943 A1 | 10/2005 |
| WO | WO 2008/035664 A1 | 3/2008 |
| WO | WO 2010/027583 A1 | 3/2010 |
| WO | WO 2010/028151 A1 | 3/2010 |
| WO | WO 2012/053627 A1 | 4/2012 |
| WO | WO 2013/012297 A1 | 1/2013 |
| WO | WO 2013/094620 A1 | 6/2013 |
| WO | WO 2014/014310 A1 | 1/2014 |
| WO | WO 2014/094960 A1 | 6/2014 |
| WO | WO 2014/094961 A1 | 6/2014 |
| WO | WO 2014/094962 A2 | 6/2014 |
| WO | WO 2014/147006 A1 | 9/2014 |
| WO | WO 2014/147134 A1 | 9/2014 |

OTHER PUBLICATIONS

Niu, Y.-H. et al., "Highly Efficient Red Electrophosphorescent Devices Based on an Iridium Complex with Trifluoromethyl-Substituted Pyrimidine Ligand," *Appl. Phys. Lett.*, Aug. 30, 2004, vol. 85 (2004), No. 9, pp. 1619-1621.

Caygill, G.B. et al., "Cyclometallated Compounds IV. Cyclopalladation of Phenylpyrimidines and X-ray Structure of a Doubly Cyclopalladated Derivative of 4,6-diphenylpyrimidine," *J. Organomet. Chem.*, Feb. 13, 1990, vol. 382 (1990), Issue 3, pp. 455-469.

Kawanishi, Y. et al., "Dependence of Spectroscopic, Electrochemical, and Excited-State Properties of Tris Chelate Ruthenium(II) Complexes on Ligand Structure," *Inorg. Chem.*, Jul. 1989, vol. 28 (1989), Issue 15, pp. 2968-2975.

Kozhevnikov, V. N. et al., "Highly Luminescent Mixed-Metal Pt(II)/Ir(III) Complexes: Bis-Cyclometalation of 4,6-Diphenylpyrimidine As a Versatile Route to Rigid Multimetallic Assemblies," *Inorg. Chem.*, May 31, 2011, vol. 50 (2011), Issue 13, pp. 6304-6313.

Baldo, M.A. et al., "Very High-Efficiency Green Organic Light-Emitting Devices Based on Electrophosphorescence," *Appl. Phys. Lett.*, Jul. 5, 1999, vol. 75 (1999), No. 1, pp. 4-6.

King, KA. et al., "Excited-State Properties of a Triply Ortho-Metalated Iridium(III) Complex," *J. Am. Chem. Soc.*, Mar. 1, 1985, vol. 107 (1985), Issue 5, pp. 1431-1432.

Kozhevnikov, V.N. et al., "Cyclometalated Ir(III) Complexes for High-Efficiency Solution-Processable Blue PhOLEDs," Chemistry of Materials, May 16, 2013, vol. 25, No. 11, pp. 2352-2358.

International Search Report re Application No. PCT/JP2014/073594, dated Nov. 25, 2014.

Written Opinion re Application No. PCT/JP2014/073594, dated Nov. 25, 2014.

* cited by examiner

ORGANOMETALLIC IRIDIUM COMPLEX, LIGHT-EMITTING ELEMENT, LIGHT-EMITTING DEVICE, ELECTRONIC DEVICE, AND LIGHTING DEVICE

TECHNICAL FIELD

The present invention relates to an object, a method, and a manufacturing method. In addition, the present invention relates to a process, a machine, manufacture, and a composition of matter. One embodiment of the present invention relates to a semiconductor device, a display device, a light-emitting device, a lighting device, a driving method thereof, and a manufacturing method thereof. One embodiment of the present invention relates to an organometallic iridium complex. In particular, one embodiment of the present invention relates to an organometallic iridium complex that is capable of converting a triplet excited state into light. In addition, one embodiment of the present invention relates to a light-emitting element, a light-emitting device, an electronic device, and a lighting device each including the organometallic iridium complex.

BACKGROUND ART

In recent years, a light-emitting element using a light-emitting organic compound or inorganic compound as a light-emitting material has been actively developed. In particular, a light-emitting element called an electroluminescence (EL) element has attracted attention as a next-generation flat panel display element because it has a simple structure in which a light-emitting layer containing a light-emitting material is provided between electrodes, and characteristics such as feasibility of being thinner and more lightweight and responsive to input signals and capability of driving with direct current at a low voltage. In addition, a display using such a light-emitting element has a feature that it is excellent in contrast and image quality, and has a wide viewing angle. Further, since such a light-emitting element is a plane light source, the light-emitting element is considered applicable to a light source such as a backlight of a liquid crystal display and an illumination device.

In the case where the light-emitting substance is an organic compound having a light-emitting property, the emission mechanism of the light-emitting element is a carrier-injection type. Specifically, by applying a voltage with a light-emitting layer provided between electrodes, electrons and holes injected from the electrodes recombine to raise the light-emitting substance to an excited state, and light is emitted when the substance in the excited state returns to the ground state. There are two types of the excited states which are possible: a singlet excited state ($S^*$) and a triplet excited state ($T^*$). In addition, the statistical generation ratio thereof in a light-emitting element is considered to be $S^*:T^*=1:3$.

In general, the ground state of a light-emitting organic compound is a singlet state. Light emission from a singlet excited state ($S^*$) is referred to as fluorescence where electron transition occurs between the same multiplicities. In contrast, light emission from a triplet excited state ($T^*$) is referred to as phosphorescence where electron transition occurs between different multiplicities. Here, in a compound emitting fluorescence (hereinafter referred to as a fluorescent compound), in general, phosphorescence cannot observed at room temperature, and only fluorescence can be observed. Accordingly, the internal quantum efficiency (the ratio of generated photons to injected carriers) in a light-emitting element using a fluorescent compound is assumed to have a theoretical limit of 25% based on $S^*:T^*=1:3$.

In contrast, the use of a phosphorescent compound can increase the internal quantum efficiency to 100% in theory. In other words, emission efficiency can be 4 times as much as that of the fluorescent compound. For these reasons, in order to obtain a highly efficient light-emitting element, a light-emitting element using a phosphorescent compound has been developed actively recently. As the phosphorescent compound, an organometallic complex that has iridium or the like as a central metal have particularly attracted attention because of their high phosphorescence quantum yield (for example, see Patent Documents 1 to 4).

Specifically, Patent Document 4 discloses an organometallic complex that has a 4-arylpyrimidine derivative as a ligand and iridium as a central metal.

REFERENCE

Patent Document

[Patent Document 1] Japanese Published Patent Application No. 2007-137872
[Patent Document 2] Japanese Published Patent Application No. 2008-069221
[Patent Document 3] PCT International Publication No. 2008-035664
[Patent Document 4] Japanese Published Patent Application No. 2012-149030

DISCLOSURE OF INVENTION

Although phosphorescent materials exhibiting various emission colors have been actively developed as disclosed in Patent Documents 1 to 4, development of novel materials with higher efficiency or a longer lifetime has been demanded.

The organometallic complex disclosed in Patent Document 4 has particularly excellent characteristics. For example, when the 4-arylpyrimidine derivative has a phenyl group at the 6-position, the transition dipole moment becomes stronger and the oscillator strength becomes larger. Such large oscillator strength leads to, for example, higher efficiency of energy transfer from a host material to the organometallic complex, so that highly efficient light emission can be achieved. However, depending on the substituent and its position, π-conjugation in the organometallic complex extends, which means that even if highly efficient light emission is achieved, the emission wavelength becomes long in some cases. When the emission wavelength becomes long, the organometallic complex emits light having a low luminosity factor.

In view of the above, an object of one embodiment of the present invention is to provide an organometallic iridium complex with high emission efficiency and a long lifetime. An object of one embodiment of the present invention is to provide an organometallic iridium complex in which π-conjugation does not easily extend and which has high emission efficiency. An object of one embodiment of the present invention is to provide an organometallic iridium complex that emits light having a high luminosity factor at high efficiency. An object of one embodiment of the present invention is to provide a novel organometallic iridium complex. An object of one embodiment of the present invention is to provide a light-emitting element, a light-emitting device, an electronic device, or a lighting device having high emission efficiency.

An object of one embodiment of the present invention is to provide a novel light-emitting element and a novel light-emitting device.

Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is an organometallic iridium complex including a structure represented by General Formula (G1).

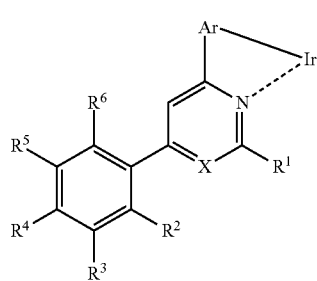

(G1)

In General Formula (G1), Ar represents a substituted or unsubstituted arylene group having 6 to 13 carbon atoms. $R^1$ to $R^6$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. A dihedral angle between a pyridine ring and a phenyl group having $R^2$ to $R^6$, or a dihedral angle between a pyrimidine ring and the phenyl group having $R^2$ to $R^6$ is greater than or equal to 30° and less than or equal to 90°. An interior angle of the pyridine ring facing $R^1$ or an interior angle of the pyrimidine ring facing $R^1$ is within a range of ±2° of 120°.

Another embodiment of the present invention is an organometallic iridium complex represented by General Formula (G2).

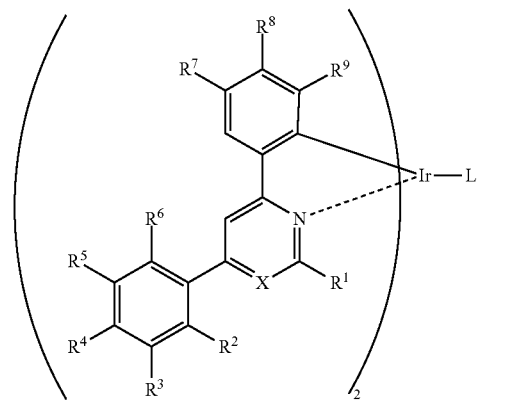

(G2)

In General Formula (G2), $R^1$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. Further, L represents a monoanionic ligand. A dihedral angle between a pyridine ring and a phenyl group having $R^7$ to $R^9$, or a dihedral angle between a pyrimidine ring and the phenyl group having $R^7$ to $R^9$ is greater than or equal to 0° and less than 2°. A dihedral angle between the pyridine ring and a phenyl group having $R^2$ to $R^6$, or a dihedral angle between the pyrimidine ring and the phenyl group having $R^2$ to $R^6$ is greater than or equal to 30° and less than or equal to 90°.

Another embodiment of the present invention is an organometallic iridium complex represented by General Formula (G3).

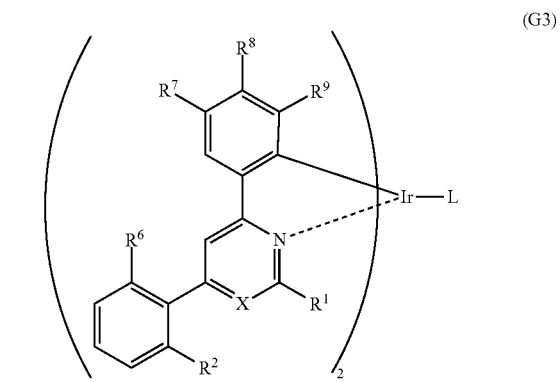

(G3)

In General Formula (G3), $R^1$, $R^2$, and $R^6$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. Further, L represents a monoanionic ligand. A dihedral angle between a pyridine ring and a phenyl group having $R^7$ to $R^9$, or a dihedral angle between a pyrimidine ring and the phenyl group having $R^7$ to $R^9$ is greater than or equal to 0° and less than 2°. A dihedral angle between the pyridine ring and a phenyl group having $R^2$ and $R^6$, or a dihedral angle between the pyrimidine ring and the phenyl group having $R^2$ and $R^6$ is greater than or equal to 30° and less than or equal to 90°.

Another embodiment of the present invention is an organometallic iridium complex represented by General Formula (G4).

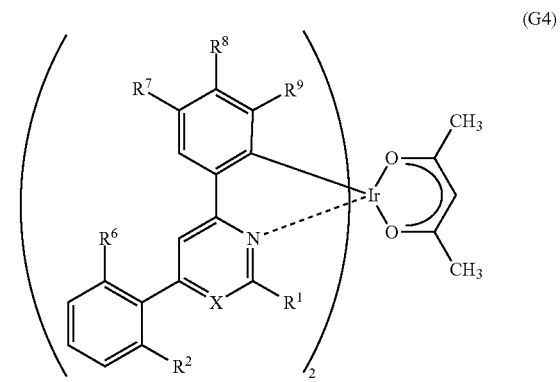

(G4)

In General Formula (G4), $R^1$, $R^2$, and $R^6$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. A dihedral angle between a pyridine ring and a phenyl group having $R^7$ to $R^9$, or a dihedral angle between a pyrimidine ring and the phenyl group having $R^7$ to $R^9$ is greater than or equal to 0° and less than 2°. A dihedral angle between the pyridine ring and a phenyl group having $R^2$ and $R^6$, or a dihedral angle between the pyrimidine ring and the phenyl group having $R^2$ and $R^6$ is greater than or equal to 30° and less than or equal to 90°.

Another embodiment of the present invention is an organometallic iridium complex represented by General Formula (G5).

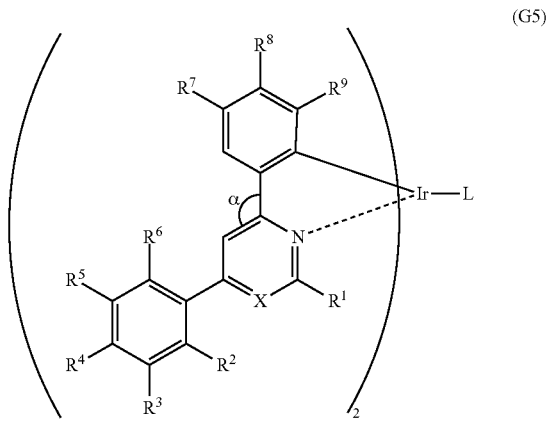

(G5)

In General Formula (G5), $R^1$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. Further, L represents a monoanionic ligand. A bond angle denoted by a in the formula is greater than or equal to 120° and less than 129°. A dihedral angle between a pyridine ring and a phenyl group having $R^2$ to $R^6$, or a dihedral angle between a pyrimidine ring and the phenyl group having $R^2$ to $R^6$ is greater than or equal to 30° and less than or equal to 90°.

Another embodiment of the present invention is an organometallic iridium complex represented by General Formula (G6).

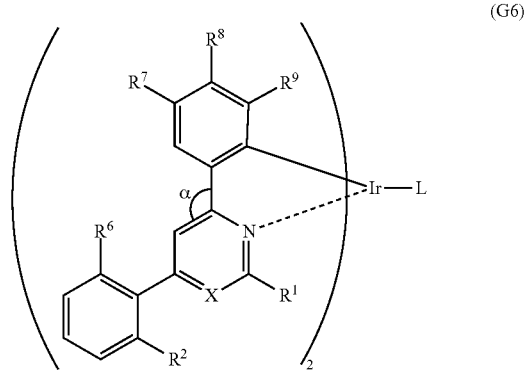

(G6)

In General Formula (G6), $R^1$, $R^2$ and $R^6$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. Further, L represents a monoanionic ligand. A bond angle denoted by a in the formula is greater than or equal to 120° and less than 129°. A dihedral angle between a pyridine ring and a phenyl group having $R^2$ and $R^6$, or a dihedral angle between a pyrimidine ring and the phenyl group having $R^2$ and $R^6$ is greater than or equal to 30° and less than or equal to 90°.

Another embodiment of the present invention is an organometallic iridium complex represented by General Formula (G7).

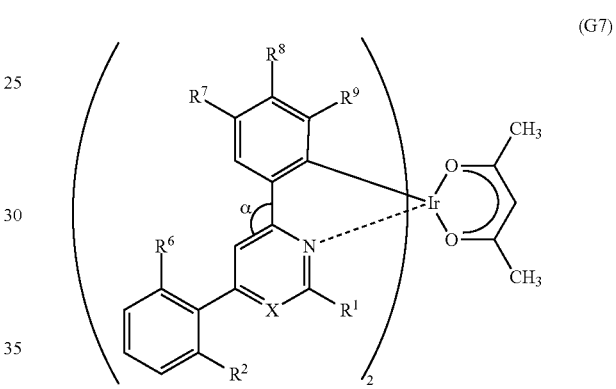

(G7)

In General Formula (G7), $R^1$, $R^2$ and $R^6$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. A bond angle denoted by a in the formula is greater than or equal to 120° and less than 129°. A dihedral angle between a pyridine ring and a phenyl group having $R^2$ and $R^6$, or a dihedral angle between a pyrimidine ring and the phenyl group having $R^2$ and $R^6$ is greater than or equal to 30° and less than or equal to 90°.

In addition, in the above-described structures, the monoanionic ligand is preferably a ligand represented by any one of General Formulae (L1) to (L7).

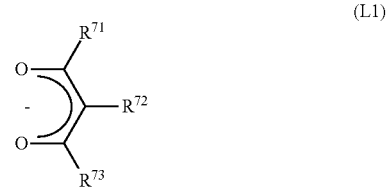

(L1)

-continued

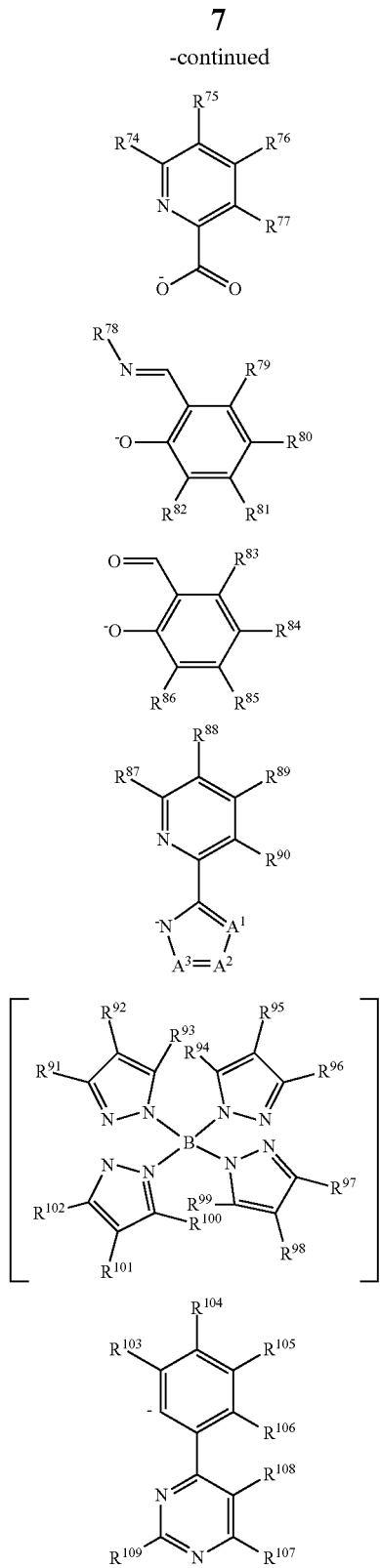

In General Formulae (L1) to (L7), $R^{71}$ to $R^{109}$ independently represent any one of hydrogen, a substituted or unsubstituted alkyl group having 1 to 6 carbon atoms, a halogen, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms. In addition, $A^1$ to $A^3$ independently represent any one of nitrogen and carbon bonded to hydrogen or to a substituent R. The substituent R is any one of an alkyl group having 1 to 6 carbon atoms, a halogen, a haloalkyl group having 1 to 6 carbon atoms, and a phenyl group.

One embodiment of the present invention is a light-emitting element including, between a pair of electrodes, any of the organometallic iridium complexes described above. In particular, any of the organometallic iridium complexes described above is preferably contained in a light-emitting layer.

Other embodiments of the present invention are a light-emitting device, an electronic device, and a lighting device each of which includes the above light-emitting element.

In one embodiment of the present invention, an organometallic iridium complex with high emission efficiency and a long lifetime can be provided. An organometallic iridium complex in which π-conjugation does not easily extend and which has high emission efficiency can be provided. An organometallic iridium complex that emits light having a high luminosity factor at high efficiency can be provided. A light-emitting element, a light-emitting device, an electronic device, or a lighting device having high emission efficiency can be provided.

Note that one embodiment of the present invention is not limited to the above effects. For example, depending on circumstances or conditions, one embodiment of the present invention might produce another effect. Furthermore, depending on circumstances or conditions, one embodiment of the present invention might not produce any of the above effects.

BEST MODE FOR CARRYING OUT THE INVENTION

Figure 1:
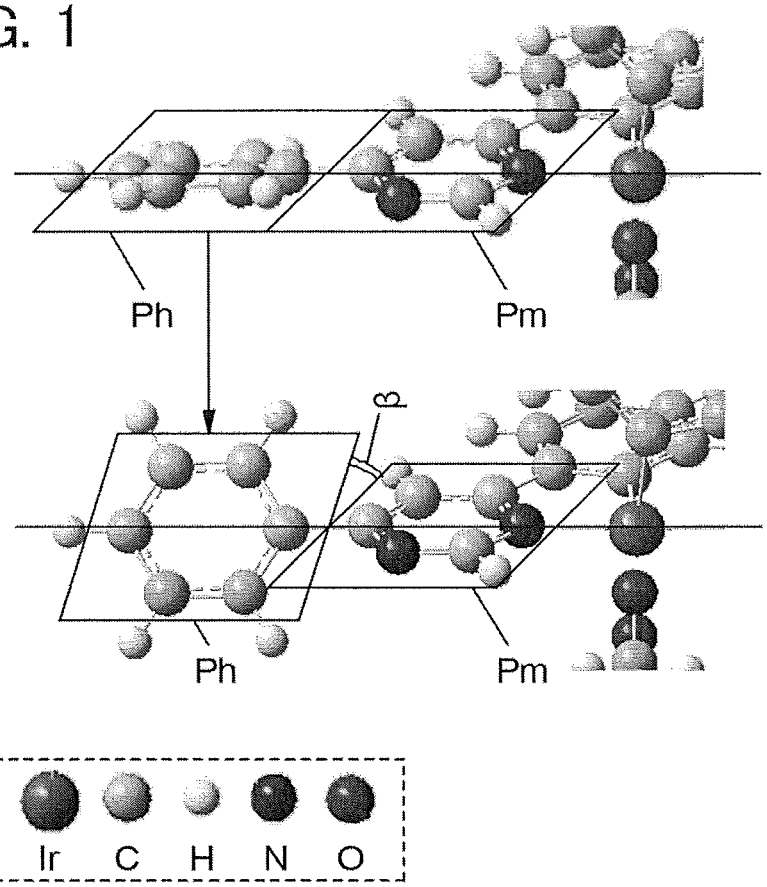
FIG. 1 illustrates models of atomic arrangement used for calculation.

Embodiments will be described in detail with reference to drawings. Note that the present invention is not limited to the description below, and it is easily understood by those skilled in the art that various changes and modifications can be made without departing from the spirit and scope of the present invention. Thus, the present invention should not be interpreted as being limited to the content of the embodiments below. Note that in the structures of the invention described below, the same portions or portions having similar functions are denoted by the same reference numerals in different drawings, and description of such portions is not repeated.

A top-emission structure, a bottom-emission structure, and a dual-emission structure can be applied to the light-emitting elements described in the present specification.

In the present specification and the like, a dihedral angle and a bond angle in a molecular structure of an organometallic iridium complex are values calculated using a quantum chemistry calculation program produced by Gaussian, Inc. When another quantum chemistry calculation program is used to calculate the molecular structure of the organometallic iridium complex of one embodiment of the present invention, the calculated value is sometimes different from that obtained by using the above quantum chemistry calculation program produced by Gaussian, Inc. A calculated value might also be influenced by the calculation conditions of the quantum chemistry calculation program.

The light-emitting device in this specification and the like includes, in its category, an image display device and a light source. The light-emitting device includes the following modules in its category: a module in which a connector, such as a flexible printed circuit (FPC) or a tape carrier package (TCP), is attached to a panel, a module in which a printed wiring board is provided at the end of a TCP, and a module in which an integrated circuit (IC) is directly mounted on a light-emitting element by a chip-on-glass (COG) method.

(Embodiment 1)

In this embodiment, organometallic iridium complexes which are embodiments of the present invention are described.

One embodiment of the present invention is an organometallic iridium complex including a structure represented by General Formula (G1).

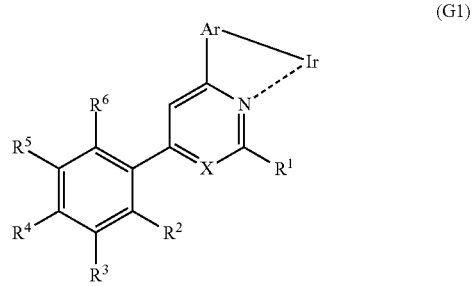

(G1)

In General Formula (G1), Ar represents a substituted or unsubstituted arylene group having 6 to 13 carbon atoms. $R^1$ to $R^6$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. A dihedral angle between a pyridine ring and a phenyl group having $R^2$ to $R^6$, or a dihedral angle between a pyrimidine ring and the phenyl group having $R^2$ to $R^6$ is greater than or equal to 30° and less than or equal to 90°. An interior angle of the pyridine ring facing $R^1$ or an interior angle of the pyrimidine ring facing $R^1$ is within a range of ±2° of 120°.

One embodiment of the present invention is an organometallic iridium complex represented by General Formula (G2).

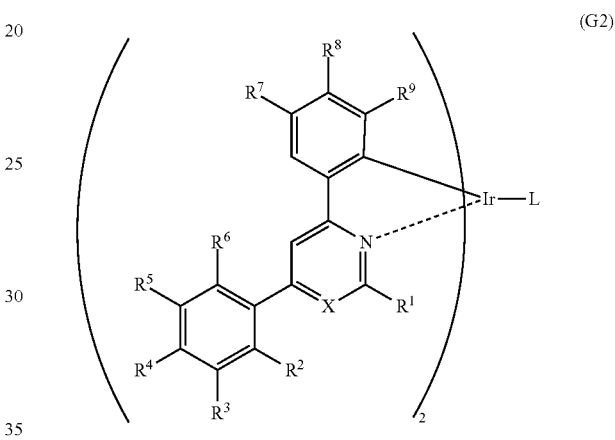

(G2)

In General Formula (G2), $R^1$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. Further, L represents a monoanionic ligand. A dihedral angle between a pyridine ring and a phenyl group having $R^7$ to $R^9$, or a dihedral angle between a pyrimidine ring and the phenyl group having $R^7$ to $R^9$ is greater than or equal to 0° and less than 2°. A dihedral angle between the pyridine ring and a phenyl group having $R^2$ to $R^6$, or a dihedral angle between the pyrimidine ring and the phenyl group having $R^2$ to $R^6$ is greater than or equal to 30° and less than or equal to 90°.

As described with reference to General Formula (G1) or (G2), one embodiment of the present invention is technically characterized by a dihedral angle between the pyridine ring or the pyrimidine ring and the phenyl group that is bonded to the pyridine ring or the pyrimidine ring in the molecular structure of the organometallic iridium complex. Since the dihedral angle between the pyridine ring or the pyrimidine ring and the phenyl group that is bonded to the pyridine ring or the pyrimidine ring is in the predetermined range, it is possible to provide an organometallic iridium complex with high emission efficiency and a long lifetime, an organometallic iridium complex in which π-conjugation does not easily extend and which has high emission efficiency, or an organometallic iridium complex that emits light having a high luminosity factor at high efficiency.

Here, from a dihedral angle between a pyridine ring or a pyrimidine ring and a phenyl group bonded to the pyridine or pyrimidine ring in the molecular structure of an organometallic iridium complex, the triplet excited level of the organometallic iridium complex was calculated. Specifically, the triplet level of (acetylacetonato)bis(4,6-diphenylpyrimidinato)iridium(III) (abbreviation: Ir(dppm)$_2$(acac)) represented by Structural Formula (500) was calculated from the dihedral angle between the pyrimidine ring and the phenyl group at the 6-position of the pyrimidine ring.

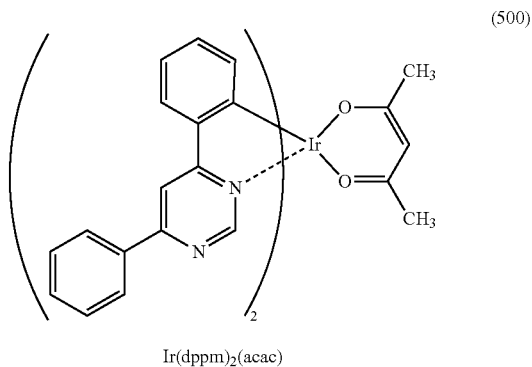

Ir(dppm)$_2$(acac)

(500)

FIG. 1 shows model diagrams of atomic arrangement used for the calculation. The model diagrams in FIG. 1 schematically illustrate atomic arrangement of a part of Ir(dppm)$_2$(acac), and are ones for explaining the dihedral angle between the pyrimidine ring (Pm) and the phenyl group (Ph) at the 6-position of the pyrimidine ring.

In the model diagram in the upper part of FIG. 1, the dihedral angle (β) between the pyrimidine ring (Pm) and the phenyl group (Ph) at the 6-position of the pyrimidine ring is 0°. The dihedral angle (β) was increased as shown in the lower part of FIG. 1, and the triplet levels of the organometallic iridium complex were calculated. Note that the dihedral angle between the pyrimidine ring (Pm) and the phenyl group at the 6-position of the pyrimidine ring in Ir(dppm)$_2$(acac) was changed from 0° to 90° at a step interval of 10°. In FIG. 1, the kinds of the atoms (an iridium atom (Ir), a carbon atom (C), a hydrogen atom (H), a nitrogen atom (N), and an oxygen atom (O)) are shown in the box bounded by the dashed line.

The calculating method is as follows. Note that Gaussian 09 was used as the quantum chemistry calculation program. A high performance computer (Altix 4700, manufactured by SGI Japan, Ltd.) was used for the calculations.

As basis functions, 6-311G(d,p) was used for H, C, N, and O, and Lanl2dz was used for Ir. As a functional, B3PW91 was used. The triplet level was worked out by TD-DFT calculation of singlet and triplet excited states. The results of calculation are shown in FIG. 2.

Figure 2:
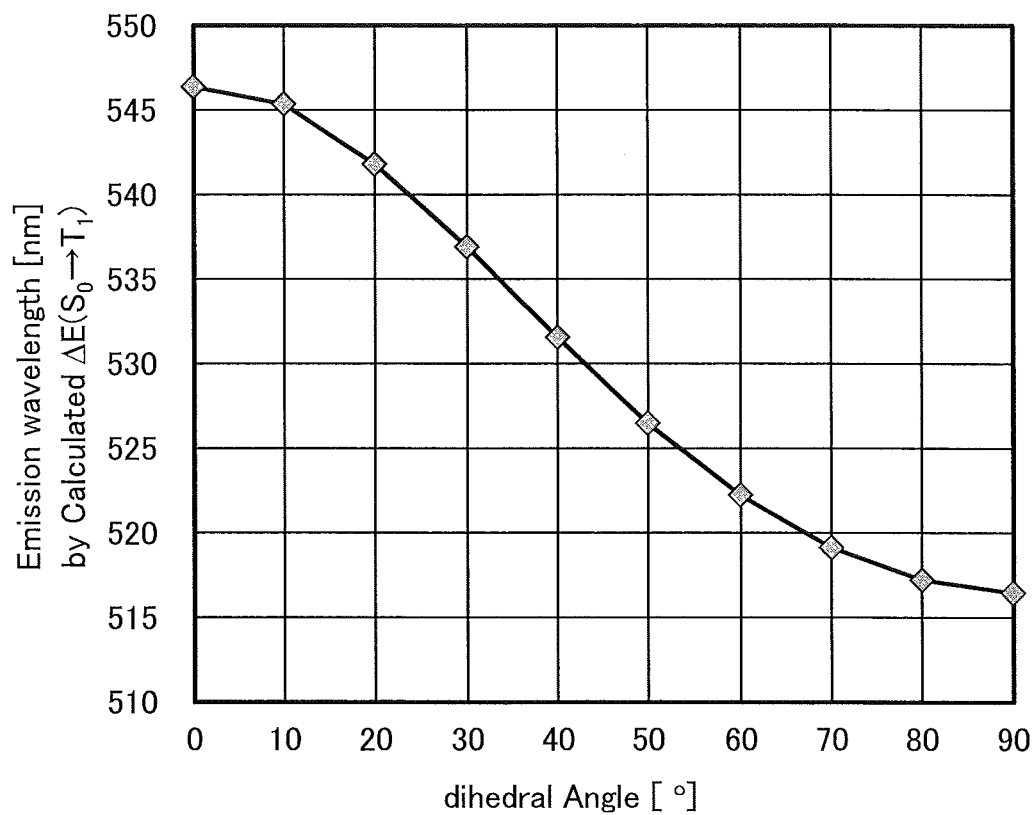
FIG. 2 shows calculation results of a dihedral angle between a pyrimidine ring and a phenyl group.

As shown by the results in FIG. 2, when the dihedral angle between the pyrimidine ring and the phenyl group at the 6-position of the pyrimidine ring in Ir(dppm)$_2$(acac) is 0°, the triplet excitation energy equivalent to a wavelength of 547 nm, and when the dihedral angle is 30°, the triplet excitation energy equivalent to a wavelength of 542 nm. When the dihedral angle between the pyrimidine ring and the phenyl group at the 6-position of the pyrimidine ring is 90°, the triplet excitation energy equivalent to a wavelength of 517 nm. FIG. 2 shows the results of calculation using dihedral angles from 0° to 90° at a step interval of 10°. In Ir(dppm)$_2$(acac) represented by Structural Formula (500), the dihedral angle between the pyrimidine ring and the phenyl group at the 6-position of the pyrimidine ring was found to be 18° by calculation. In FIG. 2, triplet excitation energy is converted into a wavelength (nm).

The calculation results in FIG. 2 suggest that in the case where the dihedral angle between the pyrimidine ring and the phenyl group at the 6-position of the pyrimidine ring in the organometallic iridium complex is greater than or equal to 30° and less than or equal to 90°, the emission wavelength becomes shorter than that in the case where the dihedral angle between the pyrimidine ring and the phenyl group at the 6-position of the pyrimidine ring in the organometallic iridium complex is 0°, by greater than or equal to 5 nm and less than or equal to 30 nm.

When the dihedral angle between the pyrimidine ring and the phenyl group at the 6-position of the pyrimidine ring in the organometallic iridium complex is increased in the above manner, i.e., when the phenyl group at the 6-position of the pyrimidine ring in the organometallic iridium complex is twisted, π-conjugation does not easily extend, and the emission wavelength decreases by approximately 30 nm at the maximum. In this manner, the emission wavelength of the organometallic iridium complex depends on the dihedral angle formed by a substituent bonded to the pyridine ring or the pyrimidine ring (here, the dihedral angle formed by the phenyl group at the 6-position of the pyrimidine ring) in the organometallic iridium complex.

Note that in the model diagrams in FIG. 1, in order that the dihedral angle formed by the phenyl group at the 6-position of the pyrimidine ring in the organometallic iridium complex can be changed, no substituent is bonded to the pyrimidine ring or the phenyl group bonded to the 6-position of the pyrimidine ring. In an actual organometallic iridium complex, bonding of a substituent to the pyridine or pyrimidine ring or the phenyl group bonded to the pyridine or pyrimidine ring can change the dihedral angle between the pyridine or pyrimidine ring and the phenyl group bonded to the pyridine or pyrimidine ring in the molecular structure of the organometallic iridium complex. However, depending on a substituent, the pyridine ring or the pyrimidine ring might be distorted.

Here, bond angles and a dihedral angle in each of organometallic iridium complexes represented by Structural Formulae (501), (500), (100), (502), (503), and (504) were calculated.

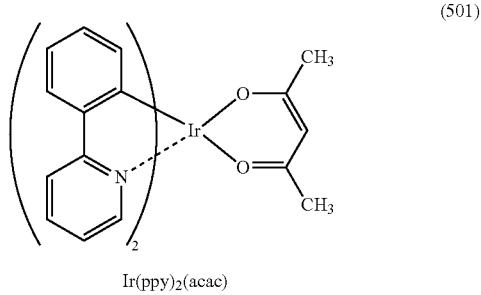

Ir(ppy)$_2$(acac)

(501)

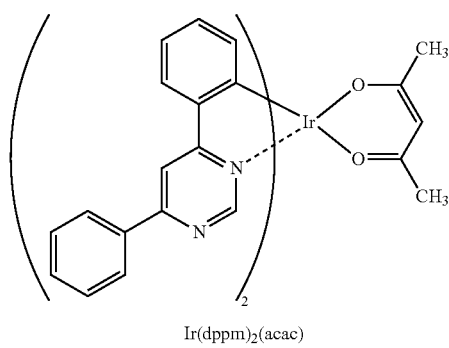

Ir(dppm)₂(acac) (500)

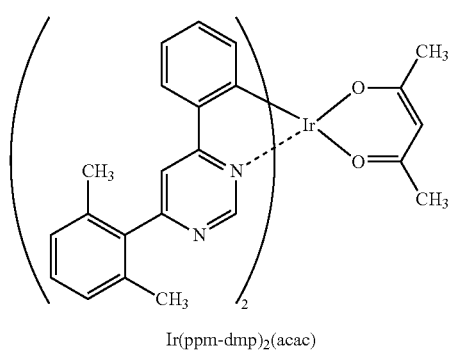

Ir(ppm-dmp)₂(acac) (100)

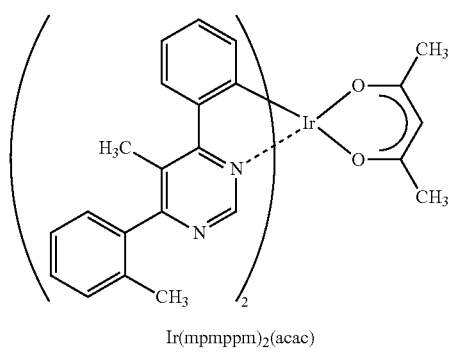

Ir(mpmppm)₂(acac) (502)

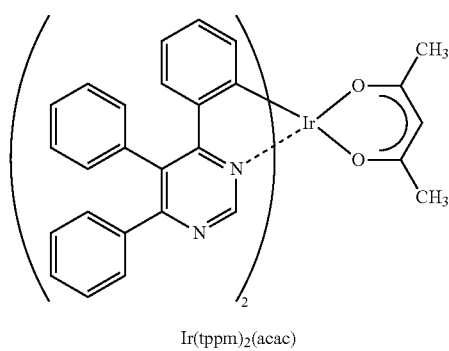

Ir(tppm)₂(acac) (503)

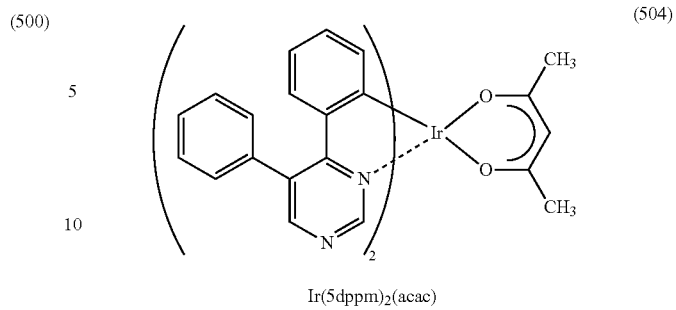

Ir(5dppm)₂(acac) (504)

Note that the organometallic iridium complex represented by Structural Formula (501) is bis(2-phenylpyridinato-N,C$^{2'}$) iridium(III) acetylacetonate (abbreviation: Ir(ppy)₂(acac)). The organometallic iridium complex represented by Structural Formula (500) is Ir(dppm)₂(acac). The organometallic iridium complex represented by Structural Formula (100) is bis{2-[6-(2,6-dimethylphenyl)-4-pyrimidinyl-κN3]phenyl-κC}(2,4-pentanedionato-κO,O')iridium(III) (abbreviation: Ir(ppm-dmp)₂(acac)). The organometallic iridium complex represented by Structural Formula (502) is (acetylacetonato)bis[5-methyl-6-(2-methylphenyl)-4-phenylpyrimidinato]iridium(III) (another name: bis {2-[5-methyl-6-(2-methylphenyl)-4-pyrimidinyl-κN3]phenyl-κC}(2,4-pentanedionato-κ²O,O')iridium(III)) (abbreviation: Ir(mpmppm)₂(acac)). The organometallic iridium complex represented by Structural Formula (503) is (acetylacetonato)bis(4,5,6-triphenylpyrimidinato)iridium(III) (another name: bis[2-(5,6-diphenyl-4-pyrimidinyl-κK3)phenyl-κC](2,4-pentanedionato-κ²O,O')iridium(III)) (abbreviation: Ir(tppm)₂(acac)). The organometallic iridium complex represented by Structural Formula (504) is bis[2-(5-phenyl-4-pyrimidinyl-κN3)phenyl-κC](2,4-pentanedionato-κ²O,O')iridium(III) (abbreviation: Ir(5dppm)₂(acac)).

The calculating method is as follows. Note that Gaussian 09 was used as the quantum chemistry calculation program. A high performance computer (Altix 4700, manufactured by SGI Japan, Ltd.) was used for the calculations.

As basis functions, 6-311G(d,p) was used for H, C, N, and O, and Lanl2dz was used for Ir. As a functional, B3PW91 was used.

As the bond angle and the dihedral angle in the organometallic iridium complexes represented by Structural Formulae (501), (500), (100), (502), (503), and (504), bond angles $\alpha_1$ and $\alpha_2$, an interior angle $\alpha_3$, and a dihedral angle $\beta_2$ of a molecular structure represented by Structural Formula (600) were calculated. The organometallic iridium complexes represented by Structural Formulae (501), (500), (100), (502), (503), and (504) have the molecular structure represented by Structural Formula (600) in common.

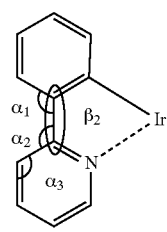

(600)

Note that in Structural Formula (600), a bond angle denoted by $\alpha_1$ is the exterior angle of the phenyl group at the 2-position of the pyridine ring; a bond angle denoted by $\alpha_2$ is the exterior angle at the 2-position of the pyridine ring; $\alpha_3$ denotes the interior angle at the 3-position of the pyridine ring; and $\beta_2$ denotes the dihedral angle between the pyridine ring and the phenyl group at the 2-position of the pyridine ring. Note that although a pyridine ring is used for description of the bond angles $\alpha_1$ and $\alpha_2$, the interior angle $\alpha_3$, and the dihedral angle $\beta_2$ in Structural Formula (600) for easy understanding, it is also possible to apply the bond angles $\alpha_1$ and $\alpha_2$, the interior angle $\alpha_3$, and the dihedral angle $\beta_2$ to a pyrimidine ring. Note that in the case of a pyrimidine ring, the site of substitution of a phenyl group is the 4-position of the pyrimidine ring.

The results of calculation are shown in Table 1.

TABLE 1

| | Structural formula | | | | | |
|---|---|---|---|---|---|---|
| | (501) | (500) | (100) | (502) | (503) | (504) |
| Angle $\alpha_1$ (°) | 123.6 | 123.5 | 123.5 | 125.6 | 125.3 | 124.7 |
| Angle $\alpha_2$ (°) | 126.5 | 127.4 | 127.6 | 129.6 | 129.8 | 129.7 |
| Angle $\alpha_3$ (°) | 120.2 | 119.3 | 119.1 | 117.0 | 117.6 | 116.9 |
| Dihedral angle $\beta_2$ (°) | 0.13 | 0.48 | 0.56 | 2.98 | 6.10 | 4.66 |

As shown in Table 1, in Structural Formulae (501), (500), and (100), the angle $\alpha_1$ is greater than or equal to 120° and less than 124°. In Structural Formulae (502), (503), and (504), the angle $\alpha_1$ is greater than or equal to 124°. In Structural Formulae (501), (500), and (100), the angle $\alpha_2$ is greater than or equal to 120° and less than 129°. In Structural Formulae (502), (503), and (504), the angle $\alpha_2$ is greater than or equal to 129°. In Structural Formulae (501), (500), and (100), the angle $\alpha_3$ is within a range of ±2° of 120°, while the angle $\alpha_3$ is outside the range of ±2° of 120° in Structural Formulae (502), (503), and (504). In Structural Formulae (501), (500), and (100), the dihedral angle $\beta_2$ is greater than or equal to 0° and less than or equal to 2°, while the dihedral angle $\beta_2$ is greater than or equal to 2° in Structural Formulae (502), (503), and (504).

As described above, depending on the position or the kind of a substituent bonded to the pyridine ring or the pyrimidine ring, the shape of the pyridine ring or the pyrimidine ring is changed. In other words, the molecular structure of the pyridine ring or the pyrimidine ring is distorted. As shown in Table 1, in the organometallic iridium complexes represented by Structural Formulae (501), (500), and (100), the molecular structure distortion of the pyridine ring or the pyrimidine ring is extremely small. Meanwhile, in each of the organometallic iridium complexes represented by Structural Formulae (502), (503), and (504), the molecular structure distortion of the pyridine ring or the pyrimidine ring is large. Molecular structure distortion of the pyridine ring or the pyrimidine ring can be found by calculating any one of the angles $\alpha_1$ to $\alpha_3$ and the dihedral angle $\beta_2$ as shown in Table 1. Note that when molecular structure distortion of the pyridine ring or the pyrimidine ring is large, the quantum efficiency cannot be high in some cases.

In view of the above, in one embodiment of the present invention, the phenyl group is bonded at the predetermined position of the pyridine ring or the pyrimidine ring in the organometallic iridium complex as illustrated in General Formula (G1) or (G2). Furthermore, in the organometallic iridium complex, the dihedral angle formed by the phenyl group bonded to the pyridine ring or the pyrimidine ring is within the predetermined range. Extension of π-conjugation is thus inhibited and the wavelength of light emitted from the organometallic iridium complex becomes shorter. Moreover, molecular structure distortion of the pyridine ring or the pyrimidine ring is inhibited, whereby high quantum efficiency can be achieved.

The structure of an organometallic iridium complex of one embodiment of the present invention can be represented by not only General Formulae (G1) and (G2) but also the formulae that are shown below.

One embodiment of the present invention is an organometallic iridium complex represented by General Formula (G3).

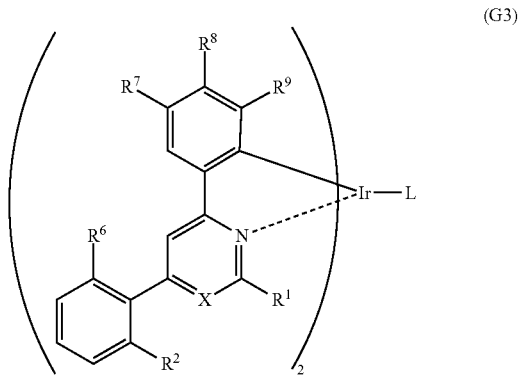

(G3)

In General Formula (G3), $R^1$, $R^2$, and $R^6$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. Further, L represents a monoanionic ligand. A dihedral angle between a pyridine ring and a phenyl group having $R^7$ to $R^9$, or a dihedral angle between a pyrimidine ring and the phenyl group having $R^7$ to $R^9$ is greater than or equal to 0° and less than 2°. A dihedral angle between the pyridine ring and a phenyl group having $R^2$ and $R^6$, or a dihedral angle between the pyrimidine ring and the phenyl group having $R^2$ and $R^6$ is greater than or equal to 30° and less than or equal to 90°.

One embodiment of the present invention is an organometallic iridium complex represented by General Formula (G4).

(G4)

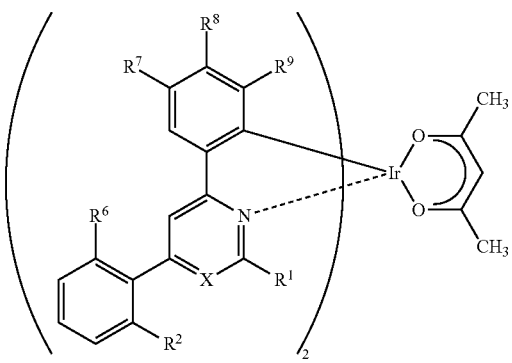

In General Formula (G4), $R^1$, $R^2$, and $R^6$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. A dihedral angle between a pyridine ring and a phenyl group having $R^7$ to $R^9$, or a dihedral angle between a pyrimidine ring and the phenyl group having $R^7$ to $R^9$ is greater than or equal to 0° and less than 2°. A dihedral angle between the pyridine ring and a phenyl group having $R^2$ and $R^6$, or a dihedral angle between the pyrimidine ring and the phenyl group having $R^2$ and $R^6$ is greater than or equal to 30° and less than or equal to 90°.

One embodiment of the present invention is an organometallic iridium complex represented by General Formula (G5).

(G5)

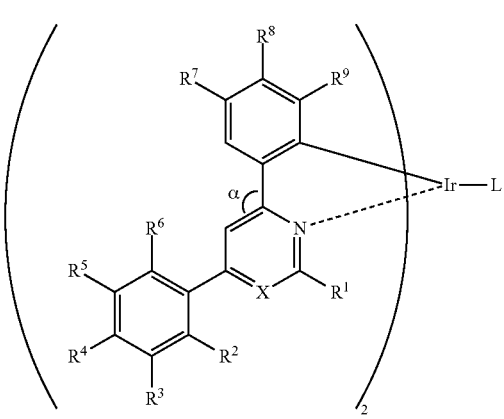

In General Formula (G5), $R^1$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. Further, L represents a monoanionic ligand. A bond angle denoted by a is greater than or equal to 120° and less than 129°. A dihedral angle between a pyridine ring and a phenyl group having $R^2$ to $R^6$, or a dihedral angle between a pyrimidine ring and the phenyl group having $R^2$ to $R^6$ is greater than or equal to 30° and less than or equal to 90°.

One embodiment of the present invention is an organometallic iridium complex represented by General Formula (G6).

(G6)

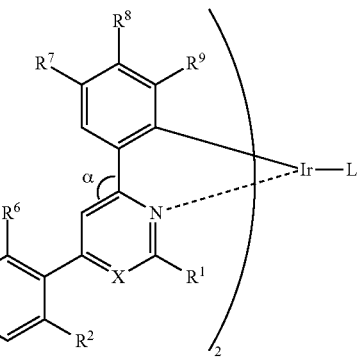

In General Formula (G6), $R^1$, $R^2$ and $R^6$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. Further, L represents a monoanionic ligand. A bond angle denoted by a in the formula is greater than or equal to 120° and less than 129°. A dihedral angle between a pyridine ring and a phenyl group having $R^2$ and $R^6$, or a dihedral angle between a pyrimidine ring and the phenyl group having $R^2$ and $R^6$ is greater than or equal to 30° and less than or equal to 90°.

One embodiment of the present invention is an organometallic iridium complex represented by General Formula (G7).

(G7)

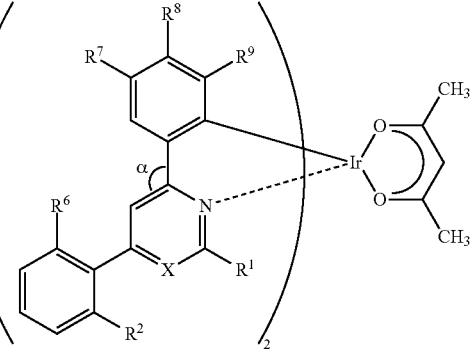

In General Formula (G7), $R^1$, $R^2$ and $R^6$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. A bond angle denoted by a in the formula is greater than or equal to 120° and less than 129°. A dihedral angle between a pyridine ring and a phenyl group having $R^2$ and $R^6$, or a dihedral angle between a pyrimidine ring and the phenyl group having $R^2$ and $R^6$ is greater than or equal to 30° and less than or equal to 90°.

In each of General Formulae (G1) to (G7), it is preferable that at least one of $R^2$ and $R^6$, further preferably both of them, represent an alkyl group. With this structure, a broad electron distribution caused by a conjugated bond between the pyridine or pyrimidine ring and the phenyl group can be prevented. In a structure in which both of $R^2$ and $R^6$ represent alkyl groups, the dihedral angle between the pyridine or pyrimidine ring and the phenyl group having $R^2$ and $R^6$ can be large.

When the interior angle of the pyridine ring facing $R^1$, or the interior angle of the pyrimidine ring facing $R^1$ is within a range of ±2° of 120° as described with reference to General Formula (G1), molecular structure distortion of the pyridine ring or the pyrimidine ring can be inhibited. When the bond angle denoted by a is greater than or equal to 120° and less than 129° as described with reference to General Formulae (G5) to (G7), molecular structure distortion of the pyridine ring or the pyrimidine ring can be inhibited.

In this manner, in the organometallic iridium complexes of embodiments of the present invention represented by General Formulae (G1) to (G7), the dihedral angle or bond angle between the pyridine or pyrimidine ring and the phenyl group bonded to the pyridine or pyrimidine ring is in the predetermined range, so that molecular structure distortion of the pyridine ring or the pyrimidine ring can be inhibited, or extension of π-conjugation between the pyridine or pyrimidine ring and the phenyl group can be inhibited by a twist formed because of steric hindrance. Thus, an emission spectrum of each of the organometallic iridium complexes can be shifted to a shorter wavelength side. In addition, higher efficiency can be achieved.

In each of the organometallic iridium complexes of embodiments of the present invention represented by General Formulae (G1) to (G7), the metal iridium and the ligand form a metal-carbon bond, so that electric charges are easily transferred from the metal to the pyridine or pyrimidine ring of the ligand (metal to ligand charge transfer (MLCT) transition easily occurs). As a result, phosphorescence, which is a forbidden transition, easily occurs, the triplet excitation lifetime is shortened, and the emission efficiency of the organometallic iridium complex can be increased.

Note that in General Formula (G2), (G3), (G5) or (G6), the monoanionic ligand can be represented by any of General Formulae (L1) to (L7). It is particularly preferable that the monoanionic ligand have the structure represented by General Formula (L1), i.e., a structure including a beta-diketone. It is further preferable that the monoanionic ligand have a structure including acetylacetone as illustrated in General Formulae (G4) and (G7). When the monoanionic ligand has a structure including a beta-diketone or a structure including acetylacetone, the emission wavelength can be reduced.

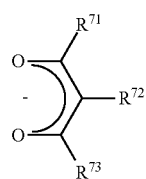

(L1)

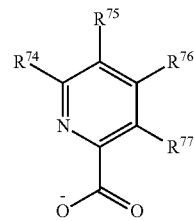

(L2)

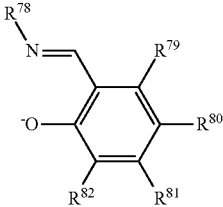

(L3)

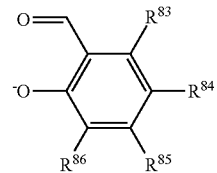

(L4)

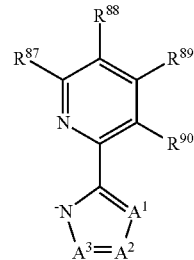

(L5)

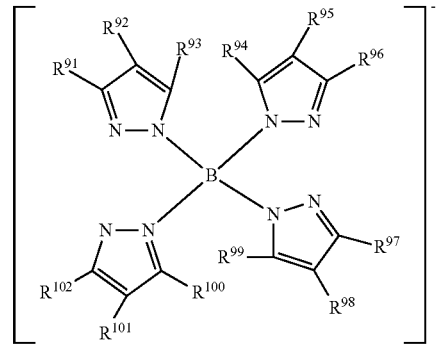

(L6)

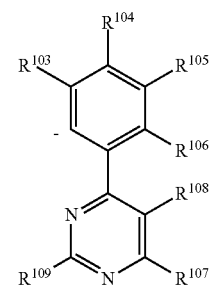

(L7)

In General Formulae (L1) to (L7), $R^{71}$ to $R^{109}$ independently represent any one of hydrogen, a substituted or unsubstituted alkyl group having 1 to 6 carbon atoms, a halogen, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms. In addition, $A^1$ to $A^3$ independently represent any one of nitrogen and carbon bonded to hydrogen or to a substituent R. The substituent R is any one of an alkyl group having 1 to 6 carbon atoms, a halogen, a haloalkyl group having 1 to 6 carbon atoms, and a phenyl group.

Next, specific structural formulae of the above-described organometallic iridium complexes of embodiments of the present invention are shown (Structural Formulae (100) to (134)). However, one embodiment of the present invention is not limited thereto.

(100)
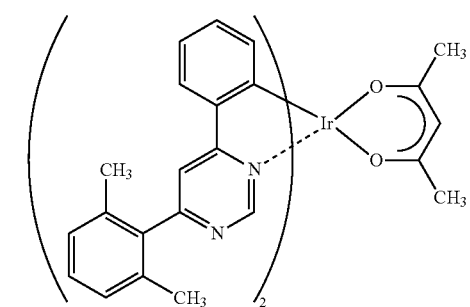

(101)
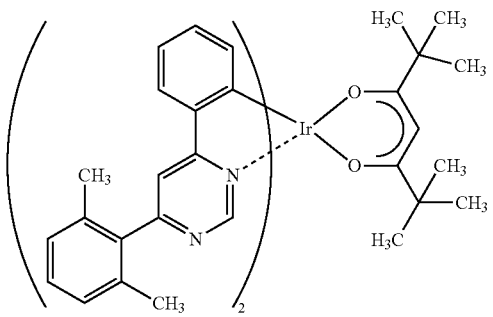

(102)
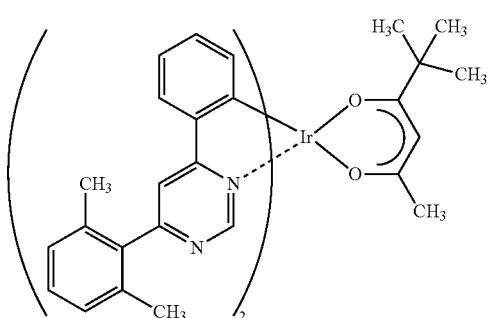

(103)
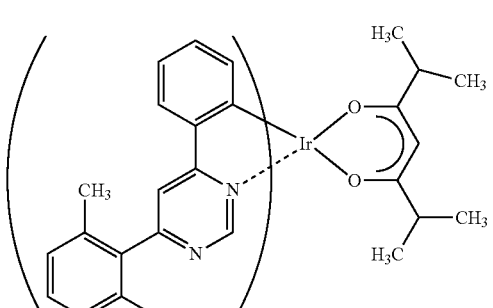

(104)
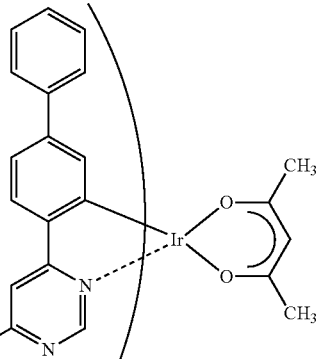

(105)
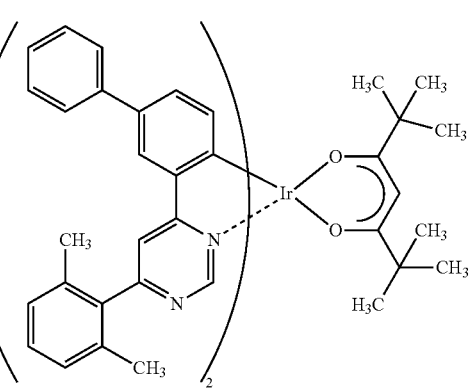

(106)
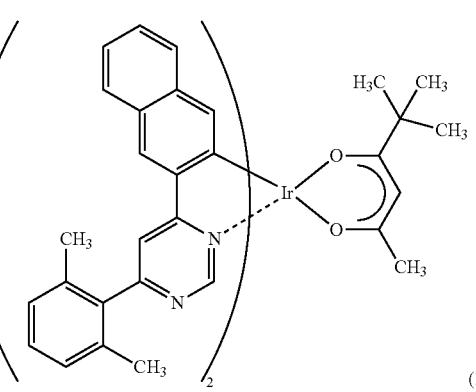

(107)
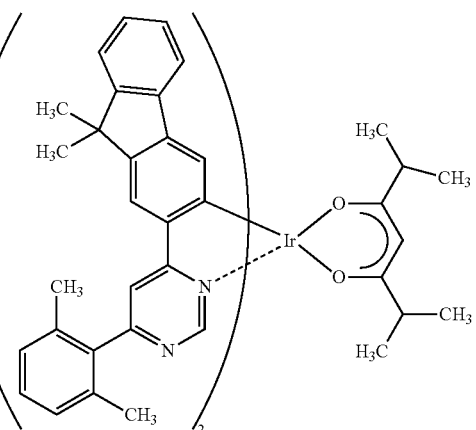

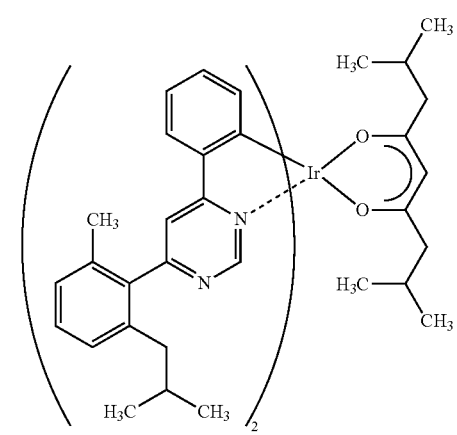
(108)
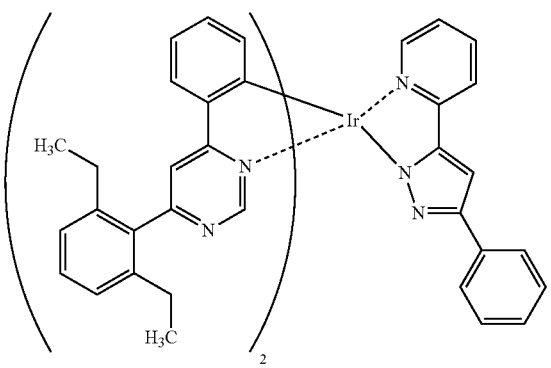
(112)
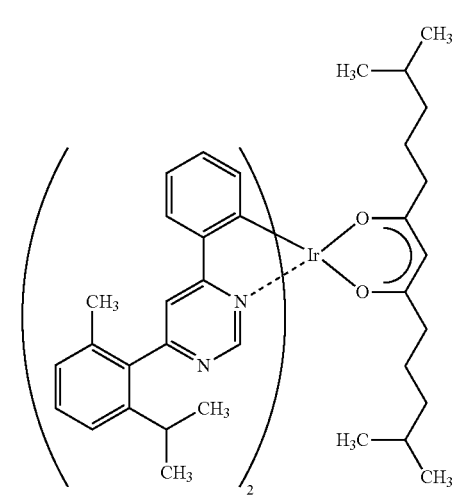
(109)
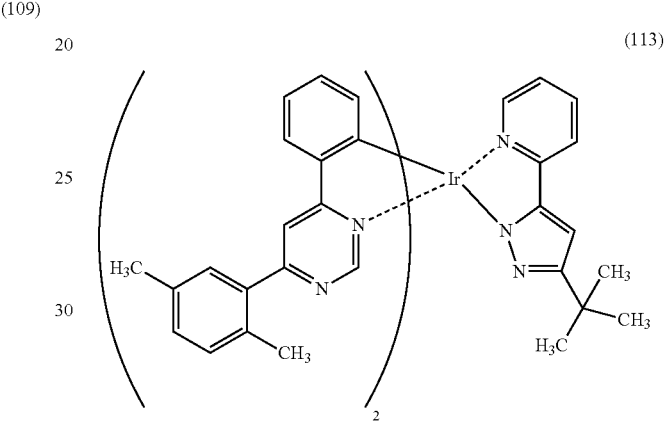
(113)
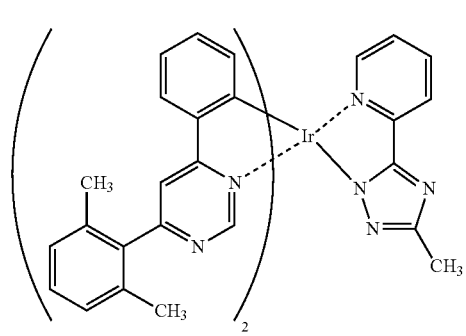
(110)
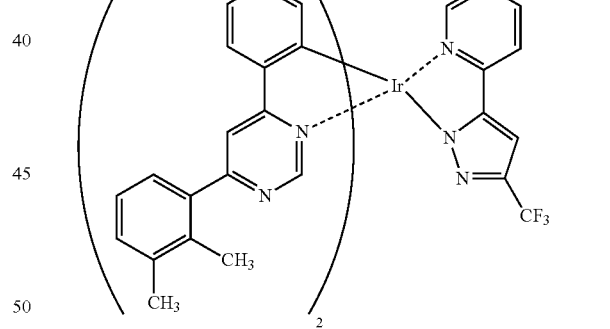
(114)
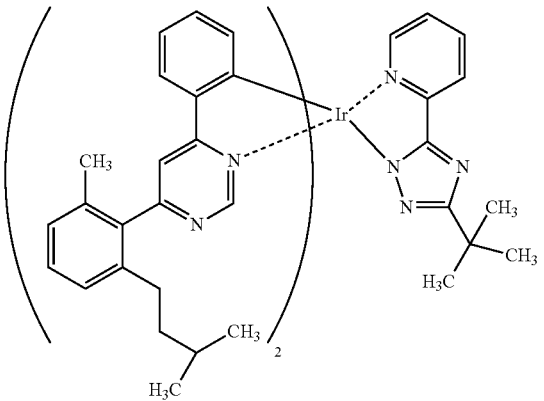
(111)
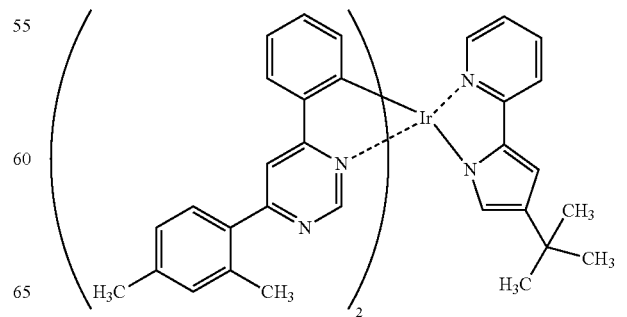
(115)

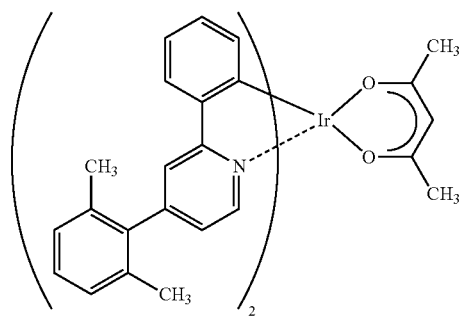
(116)
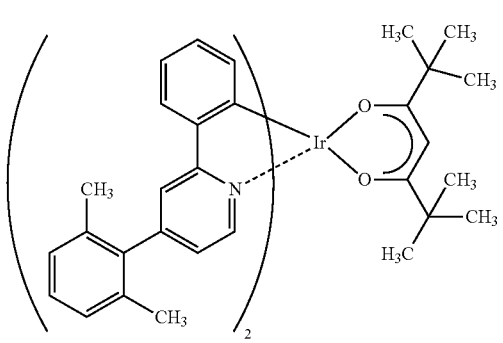
(117)
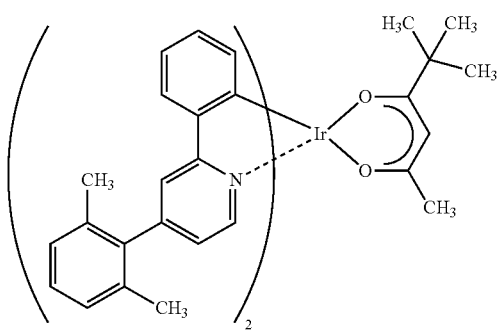
(118)
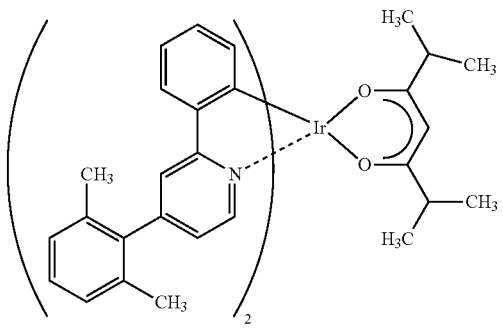
(119)
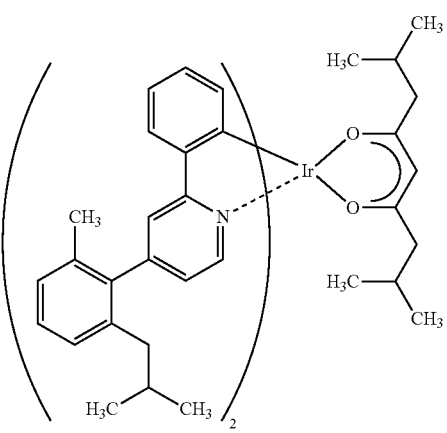
(120)
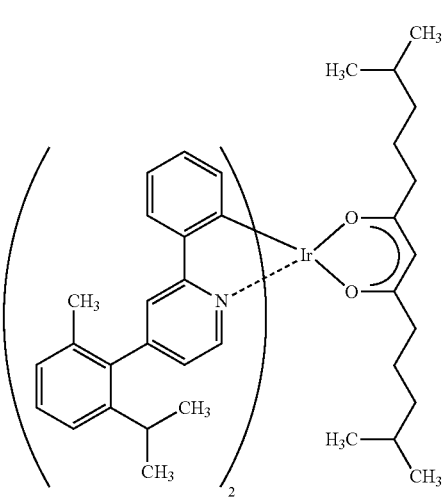
(121)
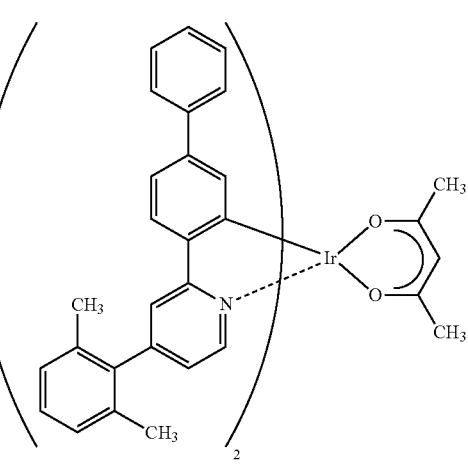
(122)

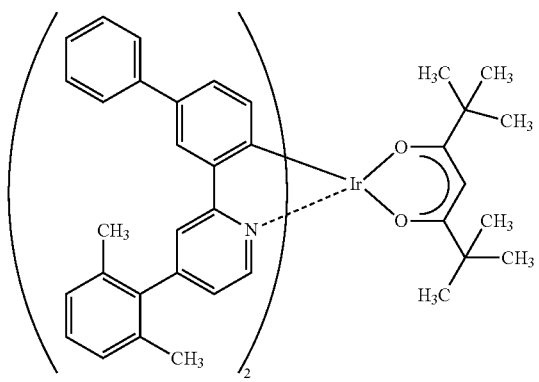
(123)
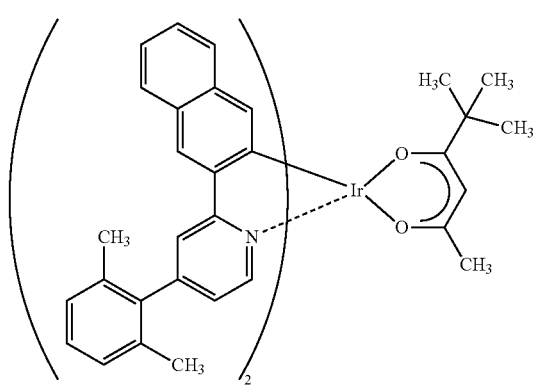
(124)
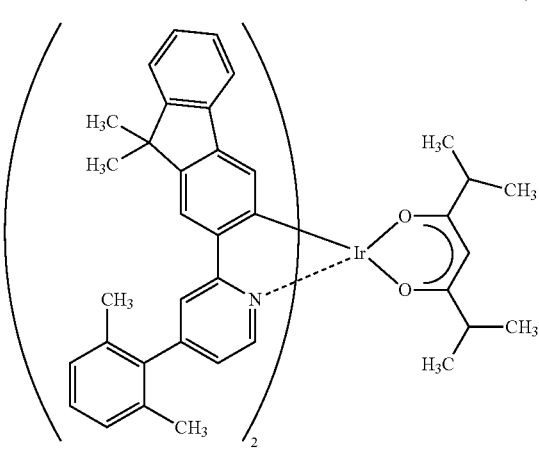
(125)
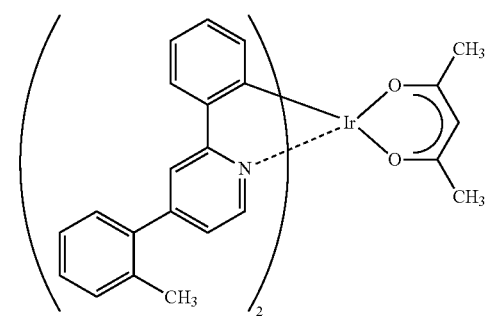
(126)
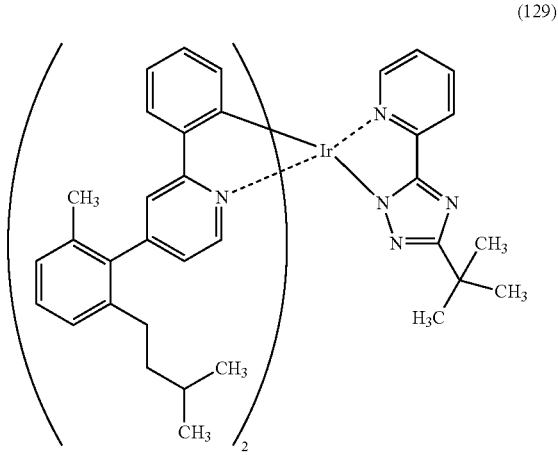
(127)
(128)
(129)
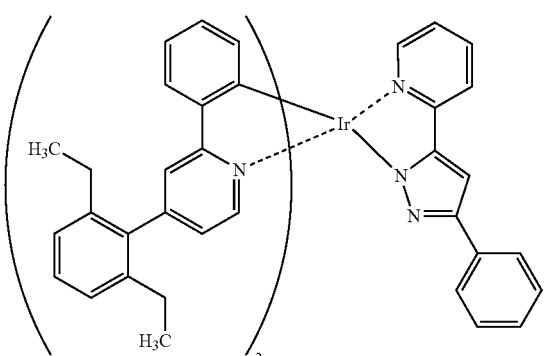
(130)

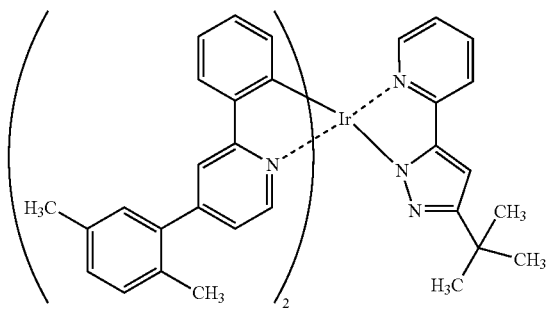
(131)

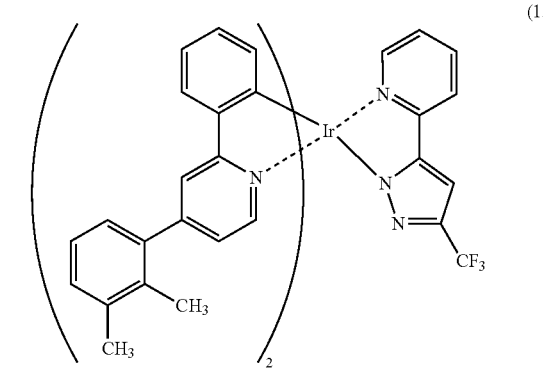
(132)

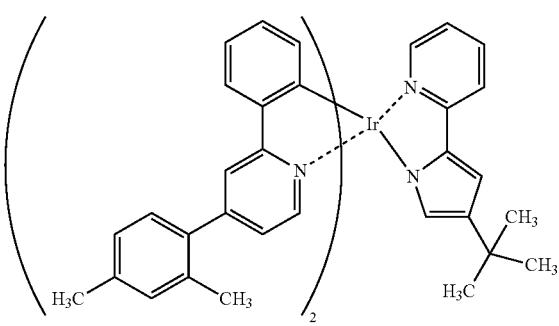
(133)

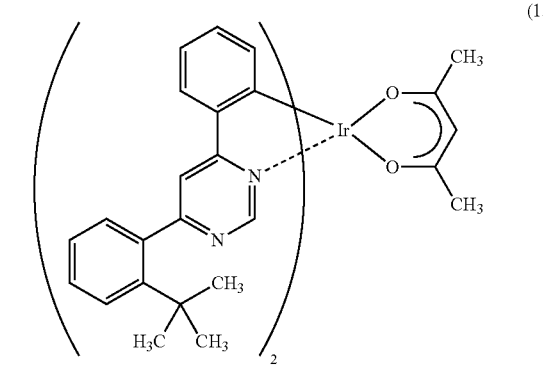
(134)

Note that organometallic iridium complexes represented by Structural Formulae (100) to (134) are novel substances capable of emitting phosphorescence. There can be geometrical isomers and stereoisomers of these substances depending on the type of the ligand. The organometallic iridium complex of one embodiment of the present invention includes all of these isomers.

Next, an example of a method for synthesizing the organometallic iridium complex represented by General Formula (G2) is described.

<<Method for Synthesizing Pyridine Derivative or Pyrimidine Derivative Represented by General Formula (G0)>>

First, an example of a method for synthesizing a pyridine derivative or a pyrimidine derivative represented by General Formula (G0) is described.

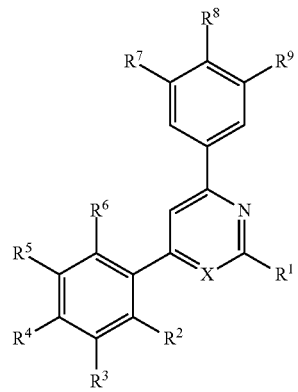
(G0)

In General Formula (G0), $R^1$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. A dihedral angle between a pyridine ring and a phenyl group having $R^7$ to $R^9$, or a dihedral angle between a pyrimidine ring and the phenyl group having $R^7$ to $R^9$ is greater than or equal to 0° and less than 2°. A dihedral angle between the pyridine ring and a phenyl group having $R^2$ to $R^6$, or a dihedral angle between the pyrimidine ring and the phenyl group having $R^2$ to $R^6$ is greater than or equal to 30° and less than or equal to 90°.

Synthesis Scheme (A) of the pyridine derivative or pyrimidine derivative represented by General Formula (G0) is shown below.

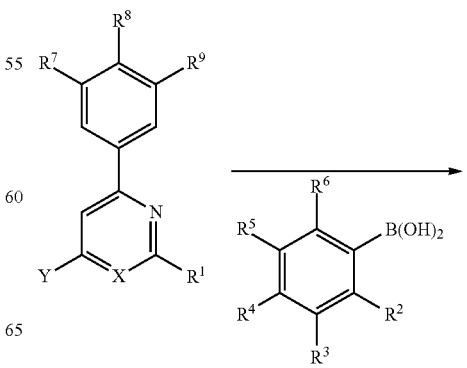
(A)

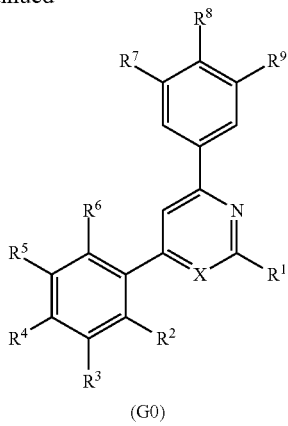

(G0)

In Synthesis Scheme (A), $R^1$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. A dihedral angle between a pyridine ring and a phenyl group having $R^7$ to $R^9$, or a dihedral angle between a pyrimidine ring and the phenyl group having $R^7$ to $R^9$ is greater than or equal to 0° and less than 2°. A dihedral angle between the pyridine ring and a phenyl group having $R^2$ to $R^6$, or a dihedral angle between the pyrimidine ring and the phenyl group having $R^2$ to $R^6$ is greater than or equal to 30° and less than or equal to 90°. In addition, Y represents a halogen. As illustrated in Synthesis Scheme (A), the pyridine derivative or pyrimidine derivative represented by General Formula (G0) can be synthesized by causing coupling reaction between 4-halogeno-2-phenylpyridine or 6-halogeno-4-phenylpyrimidine and arylboronic acid.

Since 4-halogeno-2-phenylpyridine, 6-halogen-4-phenylpyrimidine, and arylboronic acid described above are commercially available or can be synthesized, many kinds of pyridine derivatives and pyrimidine derivatives represented by General Formula (G0) can be synthesized. Thus, a feature of the organometallic iridium complex of one embodiment of the present invention is the abundance of ligand variations.

<<Method for Synthesizing an Organometallic Iridium Complex of One Embodiment of the Present Invention Represented by General Formula (G2)>>

Next, a method for synthesizing the organometallic iridium complex of one embodiment of the present invention represented by General Formula (G2), which is formed using the pyridine derivative or pyrimidine derivative represented by General Formula (G0), is described.

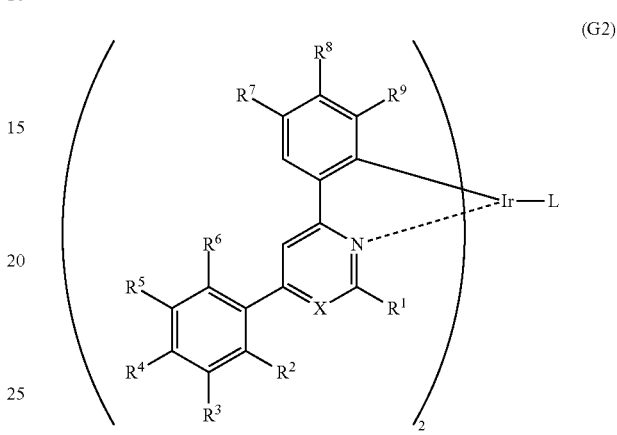

(G2)

In General Formula (G2), $R^1$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. Further, L represents a monoanionic ligand. A dihedral angle between a pyridine ring and a phenyl group having $R^7$ to $R^9$, or a dihedral angle between a pyrimidine ring and the phenyl group having $R^7$ to $R^9$ is greater than or equal to 0° and less than 2°. A dihedral angle between the pyridine ring and a phenyl group having $R^2$ to $R^6$, or a dihedral angle between the pyrimidine ring and the phenyl group having $R^2$ to $R^6$ is greater than or equal to 30° and less than or equal to 90°.

Synthesis Scheme (B) of the organometallic iridium complex represented by General Formula (G2) is shown below.

(B)

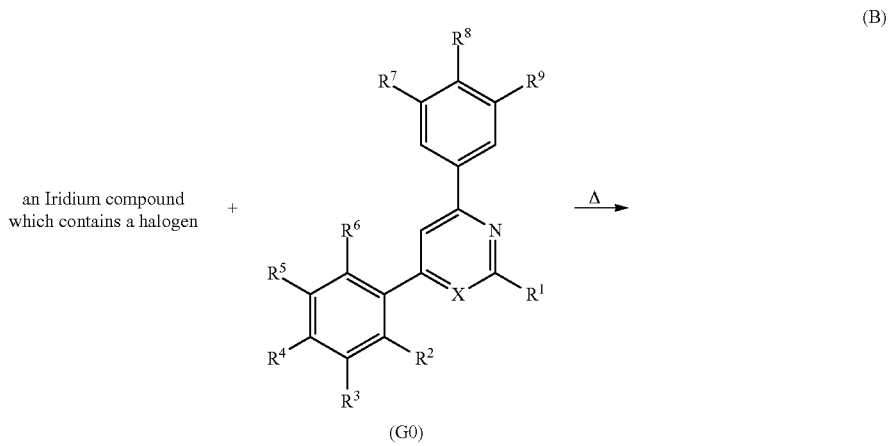

(G0)

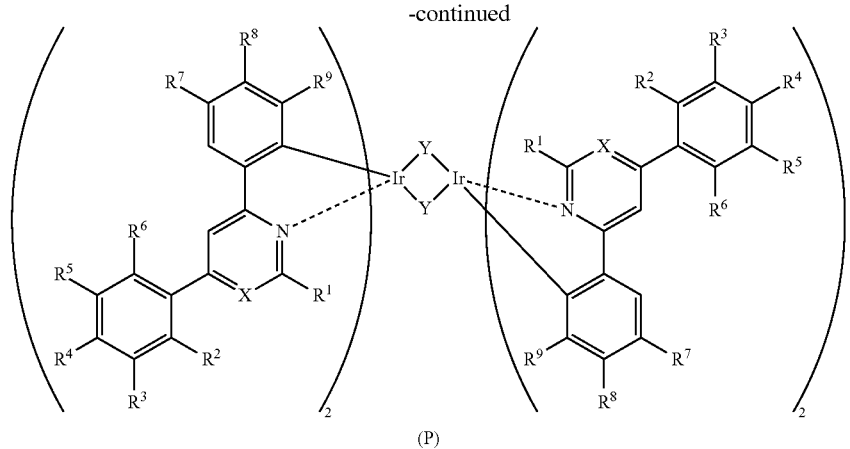

(P)

In Synthesis Scheme (B), $R^1$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. A dihedral angle between a pyridine ring and a phenyl group having $R^7$ to $R^9$, or a dihedral angle between a pyrimidine ring and the phenyl group having $R^7$ to $R^9$ is greater than or equal to 0° and less than 2°. A dihedral angle between the pyridine ring and a phenyl group having $R^2$ to $R^6$, or a dihedral angle between the pyrimidine ring and the phenyl group having $R^2$ to $R^6$ is greater than or equal to 30° and less than or equal to 90°. In addition, Y represents a halogen.

As shown in Synthesis Scheme (B), the pyridine derivative or pyrimidine derivative represented by General Formula (G0) and an iridium compound which contains a halogen (e.g., iridium chloride, iridium bromide, or iridium iodide) are heated in an inert gas atmosphere by using no solvent, an alcohol-based solvent (e.g., glycerol, ethylene glycol, 2-methoxyethanol, or 2-ethoxyethanol) alone, or a mixed solvent of water and one or more of the alcohol-based solvents, whereby a dinuclear complex (P), which is one type of an organometallic iridium complex including a halogen-bridged structure, can be obtained.

There is no particular limitation on a heating unit, and an oil bath, a sand bath, or an aluminum block may be used. Alternatively, microwaves can be used as a heating unit.

As shown in Synthesis Scheme (C), the dinuclear complex (P) obtained under Synthesis Scheme (B) is reacted with a ligand H-L in an inert gas atmosphere, whereby a proton of the ligand H-L is released and a monoanionic ligand L coordinates to the central metal iridium. Thus, the organometallic iridium complex of one embodiment of the present invention represented by General Formula (G2) can be obtained.

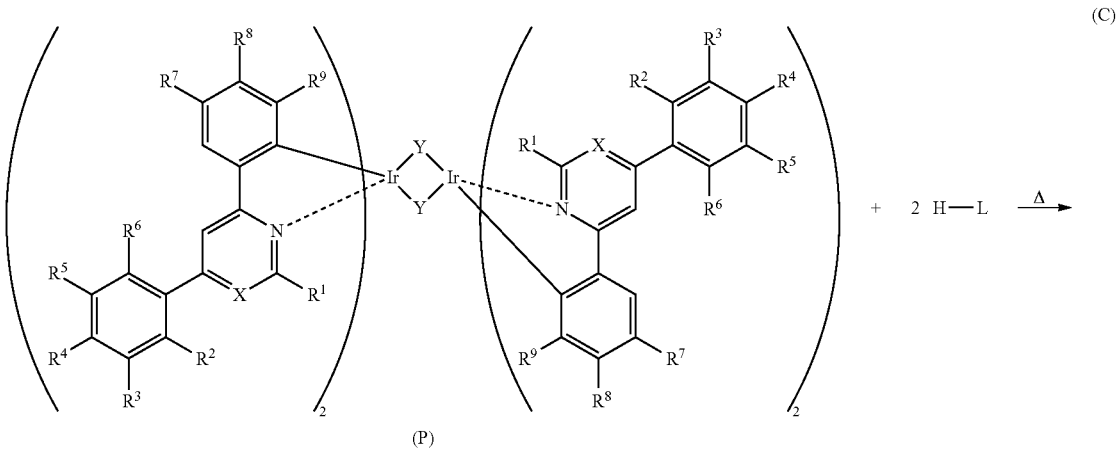

(C)

(P)

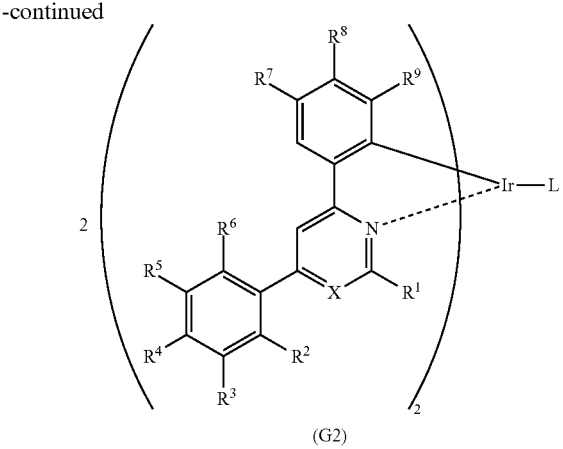

(G2)

In Synthesis Scheme (C), $R^1$ to $R^9$ independently represent any one of hydrogen and a substituted or unsubstituted alkyl group having 1 to 6 carbon atoms. Note that at least one of $R^2$ and $R^6$ represents an alkyl group having 1 to 6 carbon atoms. X represents any one of a carbon atom and a nitrogen atom, and the carbon atom has any one of hydrogen and an alkyl group having 1 to 6 carbon atoms. A dihedral angle between a pyridine ring and a phenyl group having $R^7$ to $R^9$, or a dihedral angle between a pyrimidine ring and the phenyl group having $R^7$ to $R^9$ is greater than or equal to 0° and less than 2°. A dihedral angle between the pyridine ring and a phenyl group having $R^2$ to $R^6$, or a dihedral angle between the pyrimidine ring and the phenyl group having $R^2$ to $R^6$ is greater than or equal to 30° and less than or equal to 90°. In addition, Y represents a halogen.

There is no particular limitation on a heating unit, and an oil bath, a sand bath, or an aluminum block may be used. Alternatively, microwaves can be used as a heating unit.

The above is the description of the example of a method for synthesizing an organometallic iridium complex of one embodiment of the present invention; however, one embodiment of the present invention is not limited thereto and any other synthesis method may be employed.

The above-described organometallic iridium complex of one embodiment of the present invention can emit phosphorescence and thus can be used as a light-emitting material or a light-emitting substance of a light-emitting element.

With the use of the organometallic iridium complex of one embodiment of the present invention, a light-emitting element, a light-emitting device, an electronic device, or a lighting device with high emission efficiency can be provided. Alternatively, it is possible to provide a light-emitting element, a light-emitting device, an electronic device, or a lighting device with low power consumption.

Note that the structure described in this embodiment can be combined as appropriate with any of the structures described in other embodiments.

(Embodiment 2)

In this embodiment, a light-emitting element in which the organometallic iridium complex described in Embodiment 1 as one embodiment of the present invention is used for a light-emitting layer is described with reference to FIG. 3.

Figure 3:
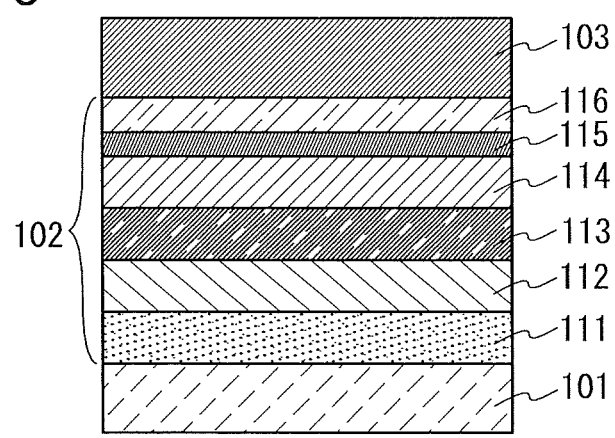
FIG. 3 illustrates a structure of a light-emitting element.

In a light-emitting element described in this embodiment, as illustrated in FIG. 3, an EL layer 102 including a light-emitting layer 113 is provided between a pair of electrodes (a first electrode 101 and a second electrode 103), and the EL layer 102 includes a hole-injection layer 111, a hole-transport layer 112, an electron-transport layer 114, an electron-injection layer 115, a charge generation layer 116, and the like in addition to the light-emitting layer 113. Note that in this embodiment, the first electrode 101 is used as an anode and the second electrode 103 is used as a cathode.

By application of a voltage to such a light-emitting element, holes injected from the first electrode 101 side and electrons injected from the second electrode 103 side recombine in the light-emitting layer 113 to raise the organometallic iridium complex to an excited state. Then, light is emitted when the organometallic iridium complex in the excited state returns to the ground state. Thus, the organometallic iridium complex of one embodiment of the present invention functions as a light-emitting substance in the light-emitting element.

The hole-injection layer 111 included in the EL layer 102 is a layer containing a substance having a high hole-transport property and an acceptor substance. When electrons are extracted from the substance having a high hole-transport property with the acceptor substance, holes are generated. Thus, holes are injected from the hole-injection layer 111 into the light-emitting layer 113 through the hole-transport layer 112.

The charge generation layer 116 is a layer containing a substance having a high hole-transport property and an acceptor substance. With the acceptor substance, electrons are extracted from the substance having a high hole-transport property and the extracted electrons are injected from the electron-injection layer 115 having an electron-injection property into the light-emitting layer 113 through the electron-transport layer 114. Note that the charge generation layer 116 is not necessarily provided and a structure without the charge generation layer 116 may be employed.

A specific example in which the light-emitting element described in this embodiment is manufactured is described.

For the first electrode 101 and the second electrode 103, a metal, an alloy, an electrically conductive compound, a mixture thereof, and the like can be used. Specifically, indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg, AlLi), a rare earth metal such as europium (Eu) or ytterbium (Yb), an alloy containing such an element, graphene, and the like can be used. The first electrode 101 and the second electrode 103 can be formed by, for example, a sputtering method, an evaporation method (including a vacuum evaporation method), or the like.

As the substance with a high hole-transport property which is used for the hole-injection layer 111, the hole-transport layer 112, and the charge generation layer 116, the following can be given, for example: aromatic amine compounds such as 4,4'-bis[N-(1-naphthyl)-N-phenylamino]biphenyl (abbreviation: NPB or α-NPD), N,N'-bis(3-methylphenyl)-N,N-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); and 3-[N-(1-naphthyl)-N-(9-phenylcarbazol-3-yl)amino]-9-phenylcarbazole (abbreviation: PCzPCN1). In addition, carbazole derivatives such as 4,4'-di(N-carbazolyl)biphenyl (abbreviation: CBP), 1,3,5-tris[4-(N-carbazolyl)phenyl] benzene (abbreviation: TCPB), and 9-[4-(10-phenyl-9-anthracenyl)phenyl]-9H-carbazole (abbreviation: CzPA) can be used. The substances mentioned here are mainly ones that have a hole mobility of $10^{-6}$ cm$^2$/Vs or higher. Note that any substance other than the above substances may be used as long as the hole-transport property is higher than the electron-transport property.

Further, a high molecular compound such as poly(N-vinylcarbazole) (abbreviation: PVK), poly(-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), and poly[N,N'-bis(4-butylphenyl)-N,N-bis(phenyl)benzidine] (abbreviation: Poly-TPD) can be used.

As examples of the acceptor substance that is used for the hole-injection layer 111 and the charge generation layer 116, a transition metal oxide or an oxide of a metal belonging to any of Group 4 to Group 8 of the periodic table can be given. Specifically, molybdenum oxide is particularly preferable.

The light-emitting layer 113 contains, as a guest material, the organometallic iridium complex of one embodiment of the present invention serving as a light-emitting substance. The light-emitting layer 113 also contains, as a host material, a substance having higher triplet excitation energy than the organometallic iridium complex.

Preferable examples of the substance (i.e., host material) used for dispersing any of the above-described organometallic iridium complexes include any of compounds having an arylamine skeleton, such as 2,3-bis(4-diphenylaminophenyl)quinoxaline (abbreviation: TPAQn) and NPB, carbazole derivatives such as CBP and 4,4',4''-tris(carbazol-9-yl)triphenylamine (abbreviation: TCTA), and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), and tris(8-quinolinolato)aluminum (abbreviation: Alq$_3$). Alternatively, a high molecular compound such as PVK can be used.

Note that in the case where the light-emitting layer 113 contains the above-described organometallic iridium complex (guest material) and the host material, phosphorescence with high emission efficiency can be obtained from the light-emitting layer 113.

The electron-transport layer 114 is a layer containing a substance having a high electron-transport property. For the electron-transport layer 114, a metal complex such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, and bis[2-(2-hydroxyphenyl)benzothiazolato]zinc (abbreviation: Zn(BTZ)$_2$) can be used. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can be used. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy) can be used. The substances mentioned here are mainly ones that have an electron mobility of $10^{-6}$ cm$^2$/Vs or higher. Note that any substance other than the above substances may be used for the electron-transport layer 114 as long as the electron-transport property is higher than the hole-transport property.

Further, the electron-transport layer 114 is not limited to a single layer, and a stacked layer in which two or more layers containing any of the above-described substances are stacked may be used.

The electron-injection layer 115 is a layer containing a substance having a high electron-injection property. For the electron-injection layer 115, an alkali metal compound or an alkaline earth metal compound, such as lithium fluoride (LiF), cesium fluoride (CsF), calcium fluoride (CaF$_2$), and lithium oxide (LiO$_x$) can be used. Alternatively, a rare earth metal compound such as erbium fluoride (ErF$_3$) can be used. Electride may also be used for the electron-injection layer 115. Examples of the electride include a mixed oxide of calcium and aluminum that contains electrons at a high concentration. The substances for forming the electron-transport layer 114, which are described above, may be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, the substances for forming the electron-transport layer 114 (e.g., a metal complex and a heteroaromatic compound), which are described above, or the like can be used. As the electron donor, a substance showing an electron-donating property with respect to the organic compound may be used. Preferable examples are an alkali metal, an alkaline earth metal, and a rare earth metal. Specifically, lithium, cesium, magnesium, calcium, erbium, ytterbium and the like can be used. In addition, alkali metal oxide and alkaline earth metal oxide such as lithium oxide, calcium oxide, and barium oxide can be given. A Lewis base such as magnesium oxide can alternatively be used. An organic compound such as tetrathiafulvalene (abbreviation: TTF) can alternatively be used.

Note that each of the above-described hole-injection layer 111, hole-transport layer 112, light-emitting layer 113, electron-transport layer 114, electron-injection layer 115, and charge generation layer 116 can be formed by an evaporation method (e.g., a vacuum evaporation method), an ink-jet method, a coating method, or the like.

In the above-described light-emitting element, current flows owing to a potential difference generated between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a light-transmitting property.

The above-described light-emitting element can emit phosphorescence originating from the organometallic iridium complex and thus can have higher efficiency than a light-emitting element using a fluorescent compound.

Note that the structure described in this embodiment can be combined as appropriate with any of the structures described in other embodiments.

(Embodiment 3)

In this embodiment, a light-emitting element in which two or more kinds of organic compounds as well as the organometallic iridium complex of one embodiment of the present invention are used for a light-emitting layer is described.

Figure 4:
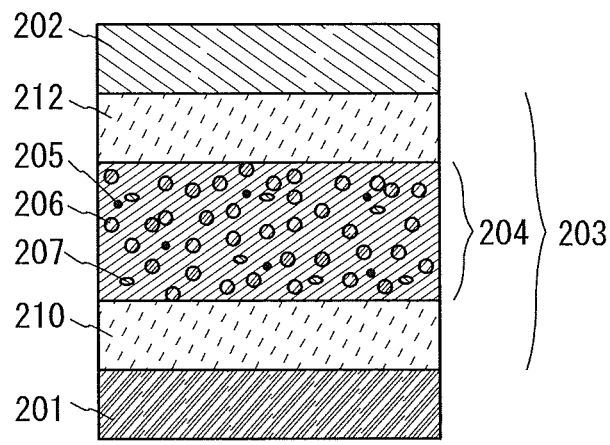
FIG. 4 illustrates a structure of a light-emitting element.

A light-emitting element described in this embodiment includes an EL layer 203 between a pair of electrodes (a first electrode 201 and a second electrode 202) as illustrated in FIG. 4. Note that the EL layer 203 includes at least a light-emitting layer 204 and may include a hole-injection layer, a hole-transport layer, an electron-transport layer, an electron-injection layer, a charge generation layer, and the like. Note that for the hole-injection layer, the hole-transport layer, the electron-transport layer, the electron-injection layer, and the charge generation layer, the substances described in Embodiment 2 can be used. FIG. 4 illustrates an example in which a first layer 210 is provided between the first electrode 201 and the light-emitting layer 204 and a second layer 212 is provided between the second electrode 202 and the light-emitting layer 204. As the first layer 210 and the second layer 212, optimal layers can be selected by the practitioner from the above-described hole-injection layer, hole-transport layer, electron-transport layer, electron-injection layer, charge generation layer, and the like. Note that in this embodiment, the first electrode 201 is used as an anode and the second electrode 202 is used as a cathode.

The light-emitting layer 204 described in this embodiment contains a phosphorescent compound 205 using the organometallic iridium complex of one embodiment of the present invention, a first organic compound 206, and a second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

Note that it is preferable that a triplet excitation energy level ($T_1$ level) of each of the first organic compound 206 and the second organic compound 207 be higher than that of the phosphorescent compound 205. The reason for this is that, when the $T_1$ level of the first organic compound 206 or the second organic compound 207 is lower than that of the phosphorescent compound 205, the triplet excitation energy of the phosphorescent compound 205, which is to contribute to light emission, is quenched by the first organic compound 206 or the second organic compound 207 and accordingly the emission efficiency decreases.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (a fluorescence spectrum in energy transfer from a singlet excited state, and a phosphorescence spectrum in energy transfer from a triplet excited state) have a large overlap with an absorption spectrum of a guest material (specifically, a spectrum in an absorption band on the longest wavelength (lowest energy) side). However, in general, it is difficult to obtain an overlap between a fluorescence spectrum of a host material and an absorption spectrum in an absorption band in the longest wavelength (lowest energy) range of a guest material. The reason for this is as follows: if the fluorescence spectrum of the host material overlaps with the absorption spectrum in the absorption band on the longest wavelength (lowest energy) side of the guest material, since the phosphorescence spectrum of the host material is located on a longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound in order to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band in the longest wavelength (lowest energy) range of a guest material so as to maximize energy transfer from a singlet excited state of the host material.

Thus, in this embodiment, the first organic compound 206 preferably forms an excited complex (also referred to as exciplex) in combination with the second organic compound 207. In that case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex which is located on a longer wavelength side. Moreover, when the first organic compound 206 and the second organic compound 207 are selected in such a manner that the emission spectrum of the exciplex has a large overlap with the absorption spectrum of the guest material, energy transfer from a singlet excited state can be maximized. Note that also in the case of a triplet excited state, energy transfer from the exciplex, not the host material, is presumed to occur.

For the phosphorescent compound 205, the organometallic iridium complex of one embodiment of the present invention is used. Although the combination of the first organic compound 206 and the second organic compound 207 can be determined such that an exciplex is formed, a combination of a compound that easily accepts electrons (a compound having an electron-trapping property) and a compound that easily accepts holes (a compound having a hole-trapping property) is preferably employed.

Examples of the compound that easily accepts electrons include 2-[3-(dibenzothiophen-4-yl)phenyl]dibenzo[f,h]quinoxaline (abbreviation: 2mDBTPDBq-II), 2-[4-(3,6-diphenyl-9H-carbazol-9-yl)phenyl]dibenzo[0]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[0]quinoxaline (abbreviation: 6mDBTPDBq-II).

Examples of the compound that easily accepts holes include 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]spiro-9,9'-bifluorene (abbreviation: DPA2SF), N,N-bis(9-phenylcarbazol-3-yl)-N,N-diphenylbenzene-1,3-diamine (abbreviation: PCA2B), N-(9,9-dimethyl-2-N,N-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N-bis[4-(carbazol-9-yl)phenyl]-N,N-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

As for the above-described first and second organic compounds 206 and 207, the present invention is not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound that easily accepts electrons and a compound that easily accepts holes are used for the first organic compound 206 and the second organic compound 207, carrier balance can be controlled by the mixture ratio of the compounds. Specifically, the weight ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; thus, it is possible to achieve high external quantum efficiency of the light-emitting element.

Note that in another structure of one embodiment of the present invention, the light-emitting layer 204 can be formed using a host molecule having a hole-trapping property and a host molecule having an electron-trapping property as the two kinds of organic compounds (the first organic compound 206 and the second organic compound 207) other than the phosphorescent compound 205 (guest material) so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds that easily accept holes and the above-described compounds that easily accept electrons.

Note that the structure described in this embodiment can be combined as appropriate with any of the structures described in other embodiments.

(Embodiment 4)

In this embodiment, as one embodiment of the present invention, a light-emitting element (hereinafter referred to as tandem light-emitting element) in which a charge generation layer is provided between a plurality of EL layers is described.

Figure 5A:
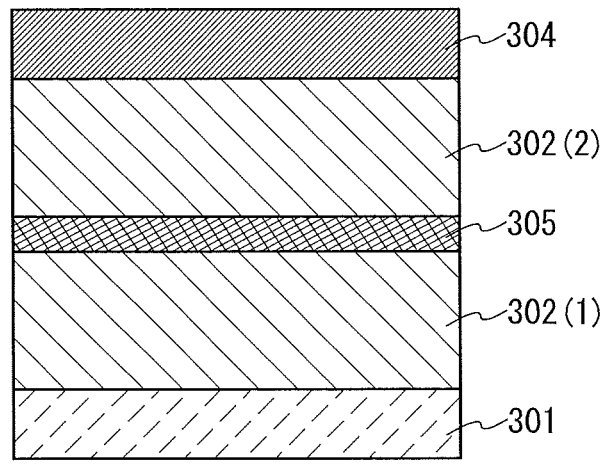
FIGS. 5A and 5B each illustrate a structure of a light-emitting element.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 5A.

In this embodiment, the first electrode 301 functions as an anode, and the second electrode 304 functions as a cathode. Note that the first electrode 301 and the second electrode 304 can have structures similar to those described in Embodiment 2. In addition, although the plurality of EL layers (the first EL layer 302(1) and the second EL layer 302(2)) may have a structure similar to that of the EL layer described in Embodiment 2 or 3, any of the EL layers may have a structure similar to that of the EL layer described in Embodiment 2 or 3. In other words, the structures of the first EL layer 302(1) and the second EL layer 302(2) may be the same or different from each other and can be similar to that of the EL layer described in Embodiment 2 or 3.

Further, a charge generation layer 305 is provided between the plurality of EL layers (the first EL layer 302(1) and the second EL layer 302(2)). The charge generation layer 305 has a function of injecting electrons into one of the EL layers and injecting holes into the other of the EL layers when a voltage is applied between the first electrode 301 and the second electrode 304. In this embodiment, when a voltage is applied such that the potential of the first electrode 301 is higher than that of the second electrode 304, the charge generation layer 305 injects electrons into the first EL layer 302(1) and injects holes into the second EL layer 302(2).

Note that in terms of light extraction efficiency, the charge generation layer 305 preferably has a light-transmitting property with respect to visible light (specifically, the charge generation layer 305 has a visible light transmittance of 40% or more). Further, the charge generation layer 305 functions even if it has lower conductivity than the first electrode 301 or the second electrode 304.

The charge generation layer 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^4$ cm$^2$/Vs or higher. Note that any substance other than the above substances may be used as long as they are organic compounds with a hole-transport property higher than an electron-transport property.

Further, as the electron acceptor, 7,7,8,8-tetracyano-2,3,5,6-tetrafluoroquinodimethane (abbreviation: F$_4$-TCNQ), chloranil, or the like can be used. Alternatively, a transition metal oxide can be used. Further alternatively, an oxide of metals that belong to Group 4 to Group 8 of the periodic table can be used. Specifically, it is preferable to use vanadium oxide, niobium oxide, tantalum oxide, chromium oxide, molybdenum oxide, tungsten oxide, manganese oxide, or rhenium oxide because the electron-accepting property is high. Among these, molybdenum oxide is especially preferable because it is stable in the air, has a low hygroscopic property, and is easily handled.

In the case of the structure in which an electron donor is added to an organic compound having a high electron-transport property, as the organic compound having a high electron-transport property for example, a metal complex having a quinoline skeleton or a benzoquinoline skeleton, such as Alq, Almq$_3$, BeBq$_2$, or BAlq, or the like can be used. Alternatively, it is possible to use a metal complex having an oxazole-based ligand or a thiazole-based ligand, such as Zn(BOX)$_2$ or Zn(BTZ)$_2$. Further alternatively, instead of a metal complex, it is possible to use PBD, OXD-7, TAZ, Bphen, BCP, or the like. The substances mentioned here are mainly ones that have an electron mobility of $10^{-6}$ cm$^2$/Vs or higher. Note that any substance other than the above substances may be used as long as they are organic compounds with an electron-transport property higher than a hole-transport property.

As the electron donor, it is possible to use an alkali metal, an alkaline earth metal, a rare earth metal, a metal belonging to Group 2 or 13 of the periodic table, or an oxide or a carbonate thereof. Specifically, it is preferable to use lithium (Li), cesium (Cs), magnesium (Mg), calcium (Ca), ytterbium (Yb), indium (In), lithium oxide, cesium carbonate, or the like. Alternatively, an organic compound such as tetrathianaphthacene may be used as the electron donor.

Note that forming the charge generation layer 305 by using any of the above materials can suppress an increase in drive voltage caused by the stack of the EL layers.

Figure 5B:
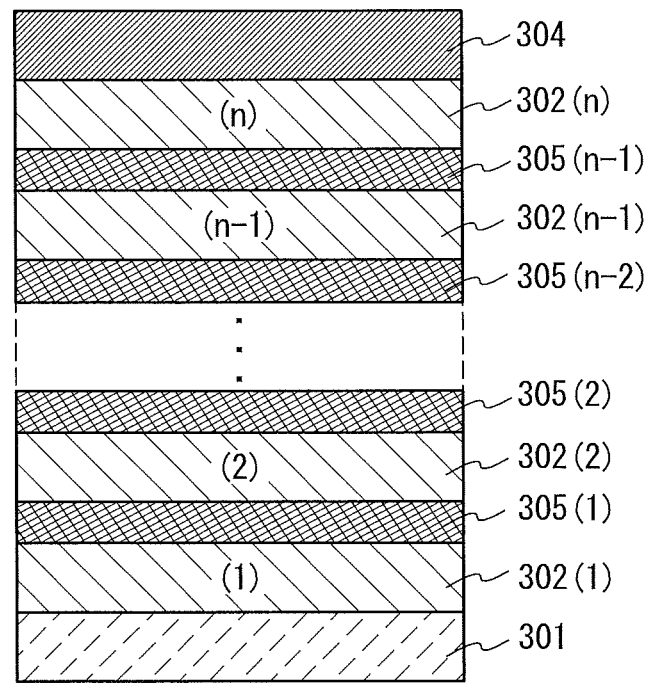

Although FIG. 5A shows the light-emitting element having two EL layers, the present invention can be similarly applied to a light-emitting element in which n EL layers (302(1) to 302(n)) (n is three or more) are stacked as illustrated in FIG. 5B. In the case where a plurality of EL layers are included between a pair of electrodes as in the light-emitting element according to this embodiment, by providing charge generation layers (305(1) to 305(n−1)) between the EL layers, light emission in a high luminance region can be obtained with current density kept low. Since the current density can be kept low, the element can have a long lifetime. When the light-emitting element is applied to lighting, voltage drop due to resistance of an electrode material can be reduced, which results in homogeneous light emission in a large area. Moreover, a light-emitting device having low power consumption, which can be driven at low voltage, can be obtained.

By making the EL layers emit light of different colors from each other, the light-emitting element can provide light emission of a desired color as a whole. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. In other words, when light obtained from a light-emitting substance and light of a complementary color are mixed, white light emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in other embodiments.

(Embodiment 5)

In this embodiment, a light-emitting device that includes a light-emitting element using the organometallic iridium complex of one embodiment of the present invention is described.

The light-emitting device can be either a passive matrix light-emitting device or an active matrix light-emitting device. Note that any of the light-emitting elements described in other embodiments can be applied to the light-emitting device described in this embodiment.

In this embodiment, an active matrix light-emitting device is described with reference to FIGS. 6A and 6B.

Figure 6A:
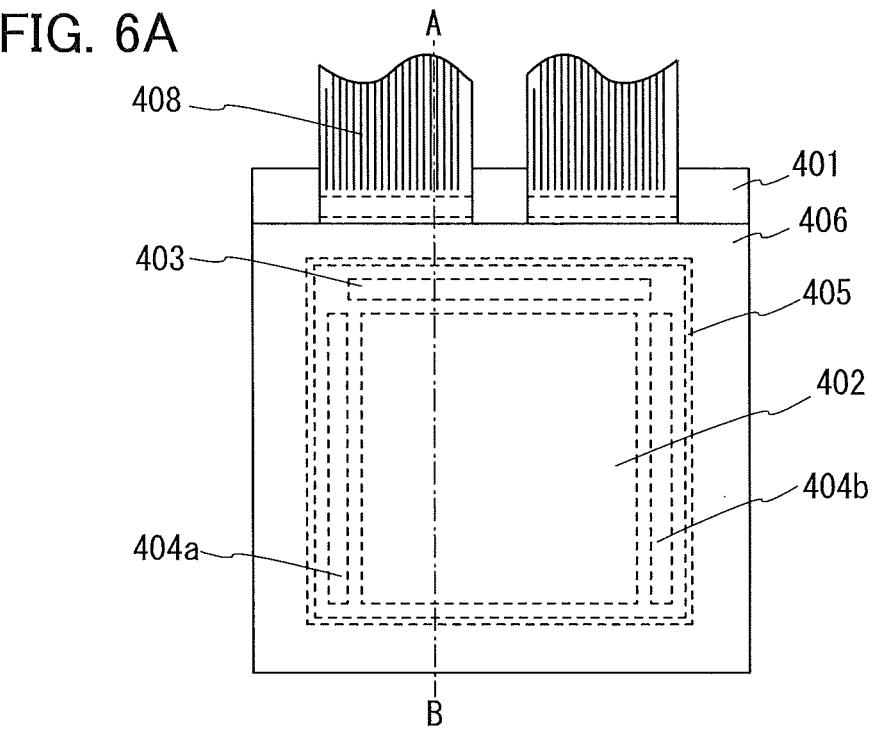
FIGS. 6A and 6B illustrate a light-emitting device.
Figure 6B:
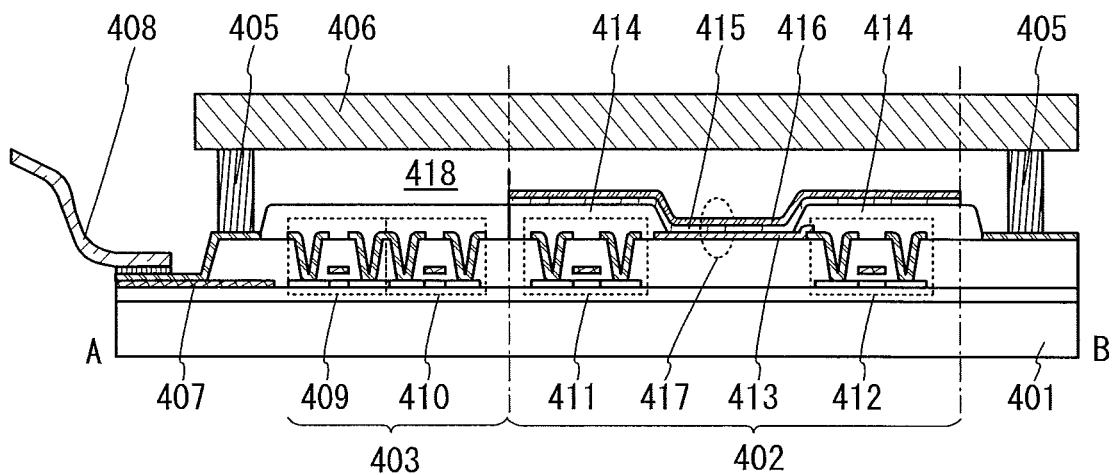

Note that FIG. 6A is a top view illustrating a light-emitting device and FIG. 6B is a cross-sectional view taken along the dashed-dotted line A-B in FIG. 6A. The active matrix light-emitting device according to this embodiment includes a pixel portion 402 provided over an element substrate 401, a driver circuit portion 403 having a function of a source line driver circuit, and driver circuit portions 404a and 404b each having a function of a gate line driver circuit. The pixel portion 402, the driver circuit portion 403, and the driver circuit portions 404a and 404b are sealed between the element substrate 401 and the sealing substrate 406 with a sealant 405.

In addition, a lead wiring 407 (not shown in FIG. 6A) is provided over the element substrate 401. The lead wiring 407 is provided for connecting an external input terminal through which a signal (e.g., a video signal, a clock signal, a start signal, and a reset signal) or a potential from the outside is transmitted to the driver circuit portion 403 and the driver circuit portions 404a and 404b. Here is shown an example in which an FPC 408 is provided as the external input terminal. Note that the FPC 408 has a function of what is called a flexible printed circuit. Although the FPC 408 is illustrated alone, this FPC 408 may be provided with a printed wiring board (PWB).

Next, the light-emitting device illustrated in FIG. 6A will be described with reference to FIG. 6B. Note that FIG. 6B does not illustrate cross-sectional structures of the driver circuit portions 404a and 404b. The structures of the driver circuit portions 404*a* and 404*b* may be the same as or different from that of the driver circuit portion 403.

FIG. 6B illustrates an example of the driver circuit portion 403 in which an FET 409 and an FET 410 are combined. The FET 409 and the FET 410 included in the driver circuit portion 403 may be formed with a circuit including transistors having the same conductivity type (either an n-channel transistor or a p-channel transistor) or a CMOS circuit including an n-channel transistor and a p-channel transistor. Furthermore, in the driver circuit portion 403, one transistor may be used or three or more transistors may be combined. Although this embodiment shows a driver integrated type in which the driver circuit is formed over the substrate, the driver circuit is not necessarily formed over the substrate, and may be formed outside the substrate.

The pixel portion 402 is formed of a plurality of pixels each of which includes a switching FET 411, a current control FET 412, and a first electrode 413 which is electrically connected to a wiring (a source electrode or a drain electrode) of the current control FET 412. Although the pixel portion 402 includes two FETs, the switching FET 411 and the current control FET 412, in this embodiment, one embodiment of the present invention is not limited thereto. The pixel portion 402 may include, for example, three or more FETs and a capacitor in combination.

As the FETs 409, 410, 411, and 412, for example, a staggered transistor, an inverted staggered transistor, or a fin-type transistor can be used. Examples of a semiconductor material that can be used for the FETs 409, 410, 411, and 412 include Group IV semiconductors (e.g., silicon and gallium), compound semiconductors, oxide semiconductors, and organic semiconductors. In addition, there is no particular limitation on the crystallinity of the semiconductor material, and an amorphous semiconductor or a crystalline semiconductor can be used. It is particularly preferable to use an oxide semiconductor for the FETs 409, 410, 411, and 412. Examples of the oxide semiconductor include an In—Ga oxide and an In—M-Zn oxide (M is Al, Ga, Y, Zr, La, Ce, or Nd). For example, an oxide semiconductor that has an energy gap of 2 eV or more, preferably 2.5 eV or more, further preferably 3 eV or more is used for the FETs 409, 410, 411, and 412, so that the off-state current of the transistors can be reduced.

An insulator 414 is formed to cover end portions of the first electrode 413. In this embodiment, the insulator 414 is formed using a positive photosensitive acrylic resin. The first electrode 413 is used as an anode in this embodiment.

The insulator 414 preferably has a curved surface with curvature at an upper end portion or a lower end portion thereof. This enables the coverage with a film to be formed over the insulator 414 to be favorable. The insulator 414 can be formed using, for example, either a negative photosensitive resin or a positive photosensitive resin. The material of the insulator 414 is not limited to an organic compound, and an inorganic compound such as silicon oxide, silicon oxynitride, or silicon nitride can also be used.

An EL layer 415 and a second electrode 416 are formed over the first electrode 413. In the EL layer 415, at least a light-emitting layer is provided. Further, in the EL layer 415, a hole-injection layer, a hole-transport layer, an electron-transport layer, an electron-injection layer, a charge generation layer, and the like can be provided as appropriate in addition to the light-emitting layer. Note that in this embodiment, the second electrode 416 is used as a cathode.

A light-emitting element 417 includes the first electrode 413, the EL layer 415, and the second electrode 416. For the first electrode 413, the EL layer 415, and the second electrode 416, the materials described in Embodiment 2 can be used. Although not illustrated, the second electrode 416 is electrically connected to the FPC 408 which is an external input terminal.

Although the cross-sectional view of FIG. 6B illustrates only one light-emitting element 417, a plurality of light-emitting elements are arranged in matrix in the pixel portion 402. Light-emitting elements which provide three kinds of light emission (R, G, and B) are selectively formed in the pixel portion 402, whereby a light-emitting device capable of full color display can be fabricated. Other than a light-emitting element which provides three kinds of light emission (R, G, and B), for example, a light-emitting element which emits white (W), yellow (Y), magenta (M), and cyan (C) light may be formed. When the above light-emitting element that provides several kinds of light emission is provided as well as a light-emitting element that provides three kinds of light emission (R, G, and B), for example, higher color purity, lower power consumption, or the like can be achieved. Alternatively, a light-emitting device capable of performing full color display may be provided by combining light-emitting elements capable of emitting white light with color filters.

Further, the sealing substrate 406 is attached to the element substrate 401 with the sealant 405, whereby the light-emitting element 417 is provided in a space 418 surrounded by the element substrate 401, the sealing substrate 406, and the sealant 405. The space 418 may be filled with an inert gas (such as nitrogen or argon), or the sealant 405.

An epoxy-based resin is preferably used for the sealant 405. It is preferable that such a material do not transmit moisture or oxygen as much as possible. As the sealing substrate 406, a glass substrate, a quartz substrate, or a plastic substrate formed of fiber reinforced plastic (FRP), poly(vinyl fluoride) (PVF), a polyester-based resin, an acrylic-based resin, or the like can be used.

As described above, an active matrix light-emitting device can be obtained.

Note that the structure described in this embodiment can be combined as appropriate with any of the structures described in other embodiments.

(Embodiment 6)

This embodiment describes examples in which a light-emitting element including the organometallic iridium complex of one embodiment of the present invention or a light-emitting device using the light-emitting element is applied to a variety of electronic devices with reference to FIGS. 7A to 7D.

Examples of the electronic devices are a television device (also referred to as television or television receiver), a monitor of a computer or the like, a camera such as a digital camera or a digital video camera, a digital photo frame, a mobile phone (also referred to as cellular phone or cellular phone device), a portable game machine, a portable information terminal, an audio reproducing device, and a large-sized game machine such as a pachinko machine.

An electronic device or a lighting device that has a light-emitting portion with a curved surface can be obtained with the use of the light-emitting element of one embodiment of the present invention which is manufactured over a substrate having flexibility.

In addition, an electronic device or a lighting device that has a see-through light-emitting portion can be obtained with the use of the light-emitting element of one embodiment of the present invention in which a pair of electrodes are formed using a material having a property of transmitting visible light.

Further, a light-emitting device to which one embodiment of the present invention is applied can also be applied to lighting for motor vehicles, examples of which are lighting for a dashboard, a windshield, a ceiling, and the like.

Figure 7A:
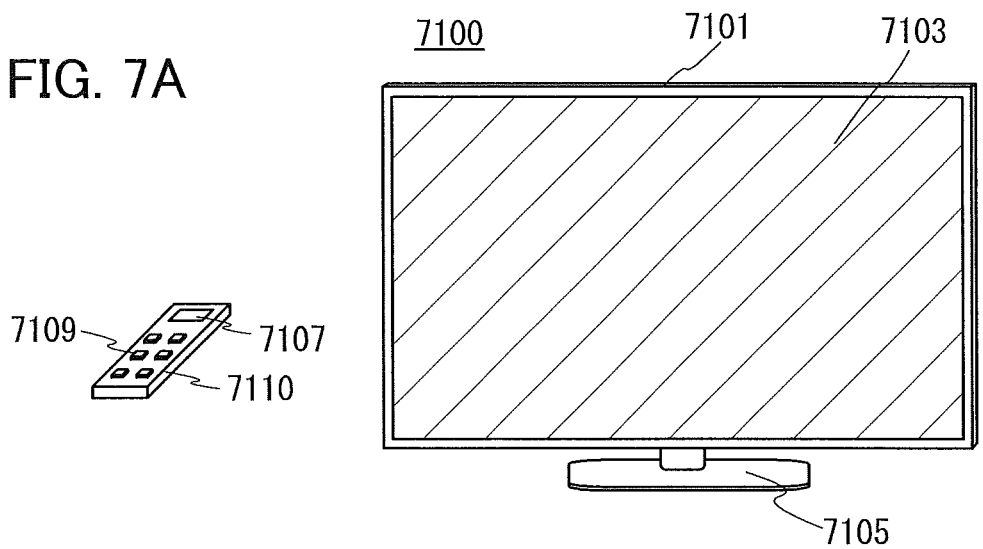
FIGS. 7A to 7D each illustrate an electronic device.

FIG. 7A illustrates an example of a television set. In a television set 7100, a display portion 7103 is incorporated in a housing 7101. Images can be displayed on the display portion 7103, and the light-emitting device can be used for the display portion 7103. In addition, here, the housing 7101 is supported by a stand 7105.

Operation of the television set 7100 can be performed with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television set 7100 is provided with a receiver, a modem, and the like. With the receiver, a general television broadcast can be received. Furthermore, when the television set 7100 is connected to a communication network by wired or wireless connection via the modem, one-way (from a transmitter to a receiver) or two-way (between a transmitter and a receiver, between receivers, or the like) data communication can be performed.

Figure 7B:
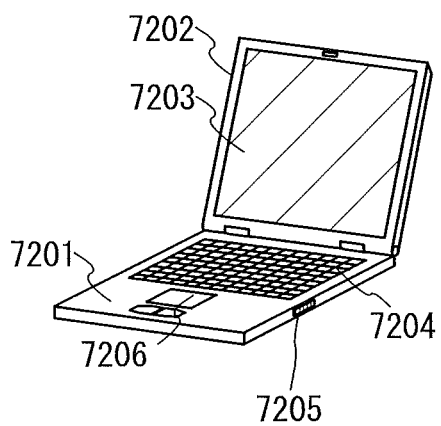

FIG. 7B illustrates a computer having a main body 7201, a housing 7202, a display portion 7203, a keyboard 7204, an external connection port 7205, a pointing device 7206, and the like. Note that this computer is manufactured using the light-emitting device for the display portion 7203.

Figure 7C:
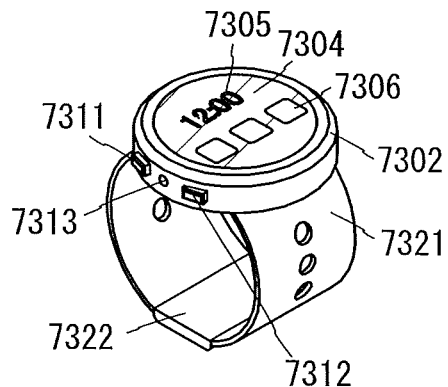

FIG. 7C illustrates a smart watch. The smart watch includes a housing 7302, a display panel 7304, operation buttons 7311 and 7312, a connection terminal 7313, a band 7321, a clasp 7322, and the like.

The display panel 7304 mounted in the housing 7302 serving as a bezel includes a non-rectangular display region. The display panel 7304 may have a rectangular display region. The display panel 7304 can display an icon 7305 indicating time, another icon 7306, and the like.

The smart watch in FIG. 7C can have a variety of functions, for example, a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display panel 7304.

Figure 7D:
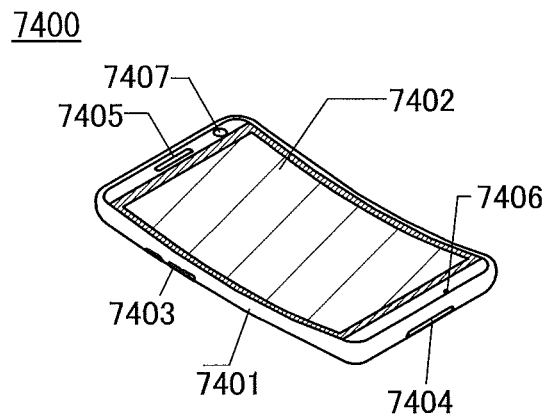

FIG. 7D illustrates an example of a mobile phone. A mobile phone 7400 includes a housing 7401 provided with a display portion 7402, a microphone 7406, a speaker 7405, a camera 7407, an external connection portion 7404, an operation button 7403, and the like. In the case where the light-emitting element of one embodiment of the present invention is formed over a flexible substrate, the light-emitting element can be used for the display portion 7402 having a curved surface as illustrated in FIG. 7D.

When the display portion 7402 of the mobile phone 7400 illustrated in FIG. 7D is touched with a finger or the like, data can be input to the mobile phone 7400. Further, operations such as making a call and composing e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing e-mail, a text input mode mainly for inputting text is selected for the display portion 7402 so that text displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically switched by determining the orientation of the mobile phone 7400 (whether the mobile phone is placed horizontally or vertically for a landscape mode or a portrait mode).

The screen modes are switched by touching the display portion 7402 or operating the operation button 7403 of the housing 7401. The screen modes can also be switched depending on the kind of an image displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken when the display portion 7402 is touched with the palm or the finger, whereby personal authentication can be performed. Further, by providing a backlight or a sensing light source which emits near-infrared light in the display portion, an image of a finger vein, a palm vein, or the like can be taken.

As described above, the electronic devices can be obtained using the light-emitting device that includes the light-emitting element of one embodiment of the present invention. Note that the light-emitting device can be used for electronic devices in a variety of fields without being limited to the electronic devices described in this embodiment.

Note that the structure described in this embodiment can be combined as appropriate with any of the structures described in other embodiments.

(Embodiment 7)

In this embodiment, examples of a lighting device and an electronic device to each of which a light-emitting element including the organometallic iridium complex of one embodiment of the present invention or a light-emitting device including the light-emitting element is applied are described with reference to FIGS. 8A to 8C.

Figure 8A:
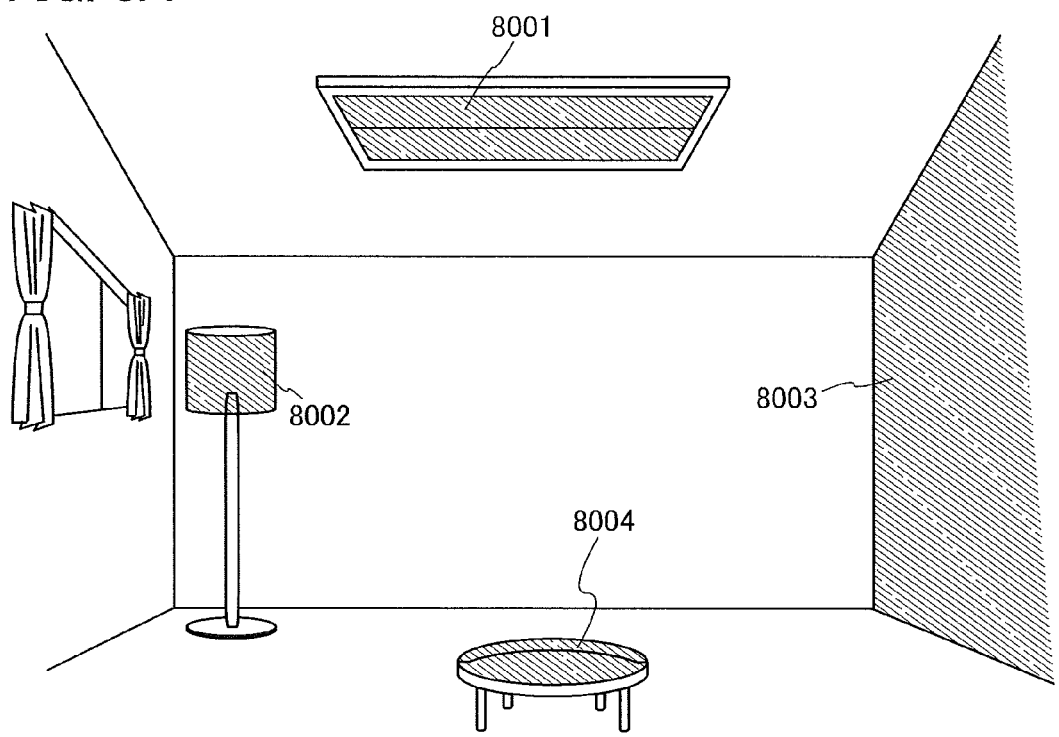
FIGS. 8A to 8C illustrate lighting devices and an electronic device.

FIG. 8A illustrates an example in which the light-emitting device is used as an indoor lighting device 8001. Since the light-emitting device can have a large area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large-sized lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

Figure 8B:
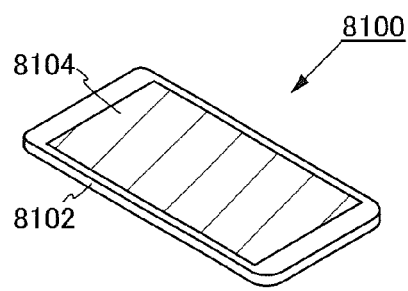
Figure 8C:
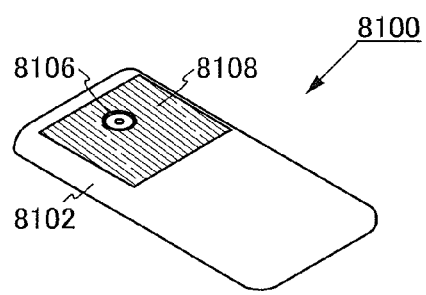

FIG. 8B is a perspective view illustrating one surface of a mobile phone, and FIG. 8C is a perspective view illustrating the other surface of the mobile phone. A mobile phone 8100 has a housing 8102 in which a display portion 8104, a camera 8106, an illumination device 8108, and the like are incorporated. The light-emitting device of one embodiment of the present invention can be used for the display portion 8104 and the illumination device 8108.

The illumination device 8108 that includes the light-emitting element containing the organometallic iridium complex of one embodiment of the present invention functions as a planar light source. Thus, unlike a point light source typified by an LED, the illumination device 8108 can provide light emission with low directivity. When the illumination device 8108 and the camera 8106 are used in combination, for example, imaging can be performed by the camera 8106 with the illumination device 8108 lighting or flashing. Because the illumination device 8108 functions as a planar light source, a photograph as if taken under natural light can be taken.

As described above, it is possible to provide various lighting devices and electronic devices to which the light-emitting element including the organometallic iridium complex of one embodiment of the present invention or the light-emitting device including the light-emitting element is applied. Note that such lighting devices and electronic devices are also embodiments of the present invention.

Note that the structure described in this embodiment can be combined as appropriate with any of the structures described in other embodiments.

EXAMPLE 1

Synthesis Example 1

In this example, a method for synthesizing bis{2-[6-(2,6-dimethylphenyl)-4-pyrimidinyl-κN3]phenyl-κC}(2,4-pentanedionato-κO,O')iridium(III) (abbreviation: Ir(ppm-dmp)$_2$(acac)), which is an organometallic iridium complex of one embodiment of the present invention represented by Structural Formula (100) in Embodiment 1, is described. The structure of Ir(ppm-dmp)$_2$(acac) is shown below.

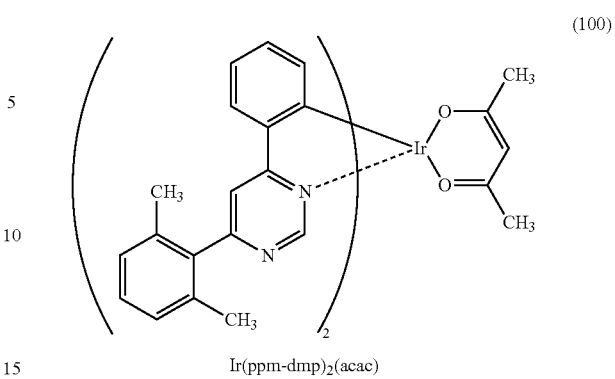

Ir(ppm-dmp)$_2$(acac)

Step 1: Synthesis of 4-chloro-6-phenylpyrimidine

First, 5.0 g of 4,6-dichloropyrimidine, 4.9 g of phenylboronic acid, 7.1 g of sodium carbonate, 0.34 g of bis(triphenylphosphine)palladium(II) dichloride, namely PdCl$_2$(PPh$_3$)$_2$, 20 mL of acetonitrile, and 20 mL of water were put into a 100-mL round-bottom flask equipped with a reflux pipe, and the air in the flask was replaced with argon. Then, heating was performed by irradiation with microwaves (2.45 GHz, 100 W) for 1 hour. An organic layer was extracted from the obtained mixture with the use of dichloromethane and was washed with water and saturated brine. Magnesium sulfate was added and gravity filtration was performed. The solvent in the obtained filtrate was distilled off, and the given residue was purified by flash column chromatography using dichloromethane as a developing solvent, whereby 1.6 g of the objective substance was obtained (yield: 23%, a pale yellow solid). Note that the irradiation with microwaves was performed using a microwave synthesis system (Discover, manufactured by CEM Corporation). A synthesis scheme of Step 1 is shown in (a-1) below.

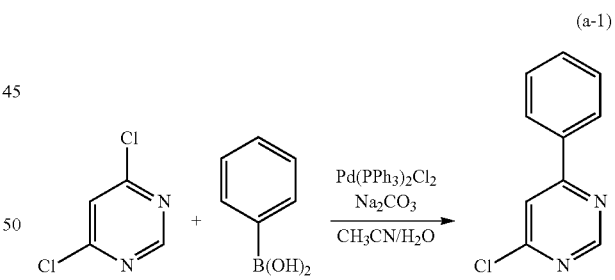

Step 2: Synthesis of 4-phenyl-6-(2,6-dimethylphenyl)pyrimidine (abbreviation: Hppm-dmp)

Next, 1.6 g of 4-chloro-6-phenylpyrimidine synthesized in Step 1, 1.5 g of 2,6-dimethylphenylboronic acid, 1.8 g of sodium carbonate, 59 mg of PdCl$_2$(PPh$_3$)$_2$, 20 mL of N,N-dimethylformamide (abbreviation: DMF), and 20 mL of water were put into a 100-mL round-bottom flask, and the air in the flask was replaced with argon. Then, heating was performed by irradiation with microwaves (2.45 GHz, 100 W) for 2 hours. An organic layer was extracted from the obtained mixture with the use of dichloromethane, and was washed with water and saturated brine. Magnesium sulfate was added and gravity filtration was performed. A solvent in the obtained filtrate was distilled off, and the given residue was purified by flash column chromatography using a mixed solvent of ethyl acetate and hexane (ethyl acetate: hexane=1:5) as a developing solvent, whereby 0.50 g of the objective substance, Hppm-dmp (abbreviation) was obtained (yield: 23%, a pale yellow oily substance). A synthesis scheme of Step 2 is shown in (a-2) below.

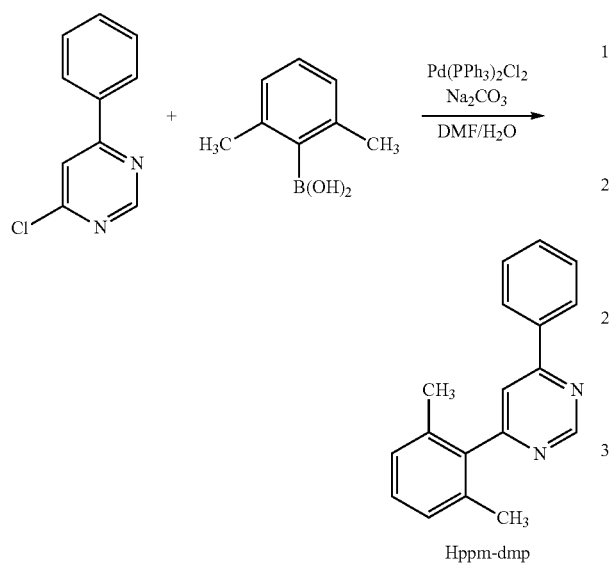

(a-2)

Hppm-dmp

Step 3: Synthesis of di-μ-chloro-tetrakis{2-[6-(2,6-dimethylphenyl)-4-pyrimidinyl-κN3]phenyl-κC}diiridium(III) (abbreviation: [Ir(ppm-dmp)₂Cl]₂)

Into a 100-mL round-bottom flask were put 1.0 g of Hppm-dmp (abbreviation) synthesized in Step 2, 0.57 g of iridium (III) chloride hydrate, 20 mL of 2-ethoxyethanol, and 20 mL of water, and the air in the flask was replaced with argon. Then, heating was performed by irradiation with microwaves (2.45 GHz, 100 W) for 3 hours. The obtained mixture was suction-filtered using methanol, whereby 1.1 g of the objective substance, [Ir(ppm-dmp)₂Cl]₂ (abbreviation) was obtained (yield: 74%, an orange solid). A synthesis scheme of Step 3 is shown in (a-3) below.

(a-3)

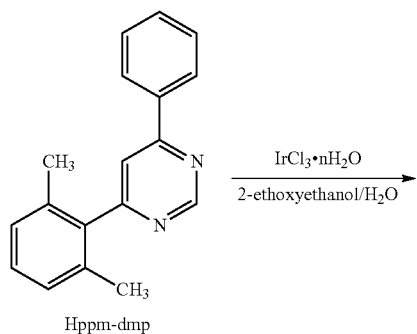

Hppm-dmp

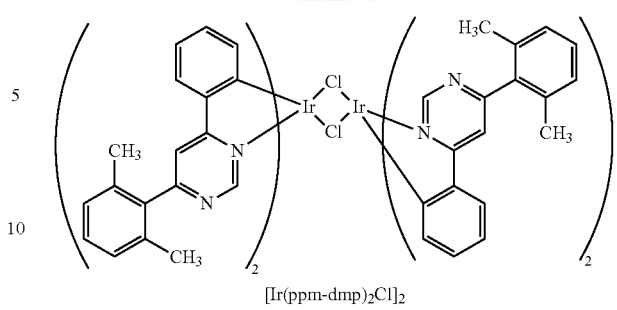

[Ir(ppm-dmp)₂Cl]₂

Step 4: Synthesis of bis{2-[6-(2,6-dimethylphenyl)-4-pyrimidinyl-κN3]phenyl-κC}(2,4-pentanedionato-κO,O')iridium(III) (abbreviation: Ir(ppm-dmp)₂(acac))

Into a 100-mL round-bottom flask equipped with a reflux pipe were put 1.1 g of [Ir(ppm-dmp)₂Cl]₂ (abbreviation) synthesized in Step 3, 0.77 g of sodium carbonate, 0.23 g of acetylacetone (abbreviation: Hacac), and 30 mL of 2-ethoxyethanol, and the air in the flask was replaced with argon. Then, heating was performed by irradiation with microwaves (2.45 GHz, 120 W) for 2 hours. The obtained mixture was suction-filtrated using methanol, and a solvent of the filtrate was distilled off. The obtained residue was purified by flash column chromatography using a mixed solvent of ethyl acetate and hexane (ethyl acetate: hexane=1:5) as a developing solvent, and recrystallization was performed using hexane, whereby an organometallic iridium complex of one embodiment of the present invention, Ir(ppm-dmp)₂(acac), was obtained (yield: 59%, an orange powdered solid). By a train sublimation method, 0.21 g of the obtained orange powdered solid was purified. In the purification by sublimation, the solid was heated at 240° C. under a pressure of 2.7 Pa with an argon flow rate of 5.0 mL/min. Thus, an orange solid, which was an objective substance, was obtained in a yield of 48%. A synthesis scheme of Step 4 is shown in (a-4) below.

(a-4)

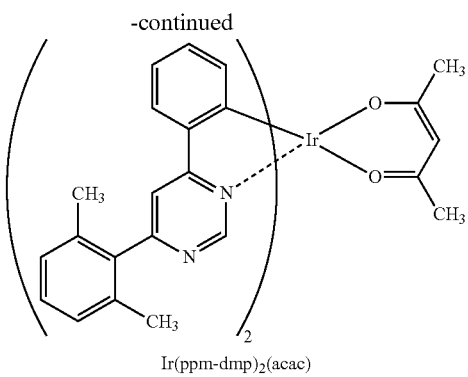

Ir(ppm-dmp)₂(acac)

Figure 9:
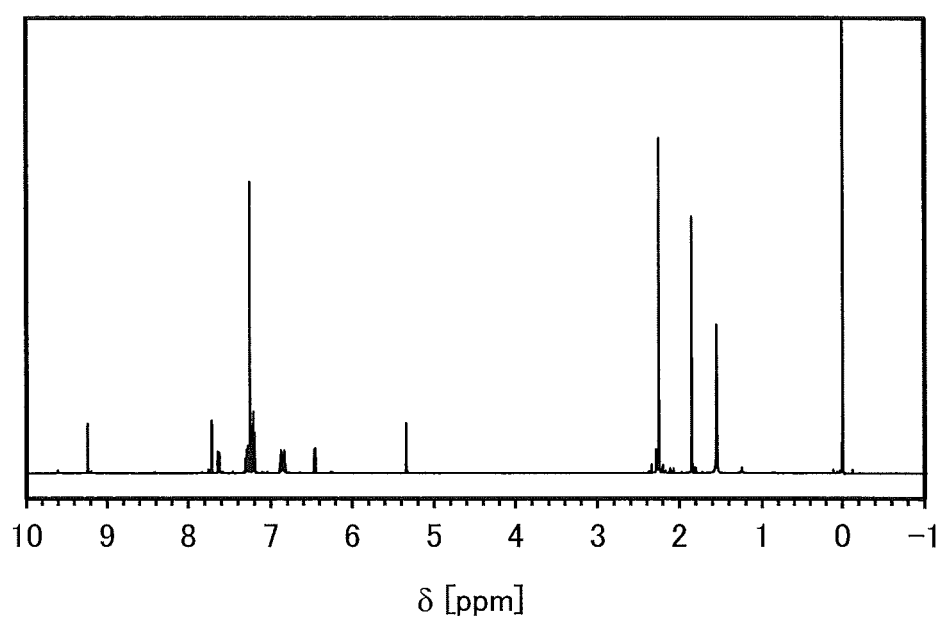
FIG. 9 is a $^1$H-NMR chart of an organometallic iridium complex represented by Structural Formula (100).

An analysis result by nuclear magnetic resonance spectrometry (¹H-NMR) of the orange solid obtained in Step 4 is described below. The ¹H NMR chart is shown in FIG. 9. The results reveal that Ir(ppm-dmp)₂(acac), which is the organometallic iridium complex of one embodiment of the present invention represented by Structural Formula (100), was obtained in Synthesis Example 1.

¹H-NMR. δ (CDCl₃): 1.85 (s, 6H), 2.26 (s, 12H), 5.35 (s, 1H), 6.46-6.48 (dd, 2H), 6.83-6.90 (dm, 4H), 7.20-7.22 (d, 4H), 7.29-7.32 (t, 2H), 7.63-7.65 (dd, 2H), 7.72 (ds, 2H), 9.24 (ds, 2H).

Figure 10:
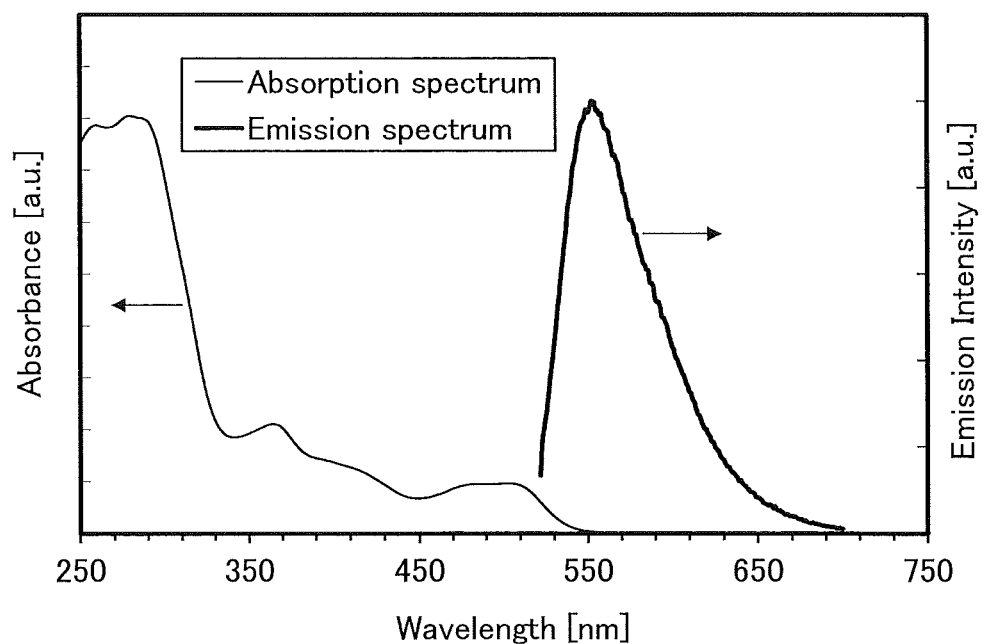
FIG. 10 shows an ultraviolet-visible absorption spectrum and an emission spectrum of an organometallic iridium complex represented by Structural Formula (100).

Next, an ultraviolet-visible absorption spectrum (hereinafter, simply referred to as an "absorption spectrum") and an emission spectrum of a dichloromethane solution of Ir(ppm-dmp)₂(acac) were measured. The measurement of the absorption spectrum was conducted at room temperature, for which an ultraviolet-visible light spectrophotometer (V550 type manufactured by Japan Spectroscopy Corporation) was used and the dichloromethane solution (0.090 mmol/L) was put in a quartz cell. In addition, the measurement of the emission spectrum was conducted at room temperature, for which a fluorescence spectrophotometer (FS920 manufactured by Hamamatsu Photonics K. K.) was used and the degassed dichloromethane solution (0.090 mmol/L) was put in a quartz cell. Measurement results of the obtained absorption and emission spectra are shown in FIG. 10, in which the horizontal axis represents wavelength and the vertical axes represent absorption intensity and emission intensity. In FIG. 10 where there are two solid lines, the thin line represents the absorption spectrum and the thick line represents the emission spectrum. Note that the absorption spectrum in FIG. 10 is the results obtained in such a way that the absorption spectrum measured by putting only dichloromethane in a quartz cell was subtracted from the absorption spectrum measured by putting the dichloromethane solution (0.090 mmol/L) in a quartz cell.

As shown in FIG. 10, Ir(ppm-dmp)₂(acac), the organometallic iridium complex of one embodiment of the present invention, has an emission peak at 553 nm, and yellow light emission was observed from the dichloromethane solution.

Note that the structure described in this example can be combined as appropriate with any of the structures described in other embodiments and examples.

EXAMPLE 2

Synthesis Example 2

In this synthesis example, an example of synthesizing bis{2-[6-(2-tert-butylphenyl)-4-pyrimidinyl-κN3]phenyl-κC}(2,4-pentanedionato-κ²O,O')iridium(III) (abbreviation: Ir(ppm-tBup)₂(acac)), which is an organometallic iridium complex of one embodiment of the present invention represented by Structural Formula (134) in Embodiment 1, is specifically described. The structure of Ir(ppm-tBup)₂(acac) is shown below.

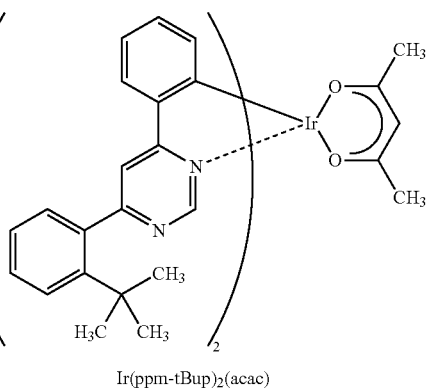

(134)

Ir(ppm-tBup)₂(acac)

Step 1: Synthesis of
4-(2-tert-butylphenyl)-6-phenylpyrimidine
(abbreviation: Hppm-tBup)

First, 1.0 g of 4-chloro-6-phenylpyrimidine, 1.1 g of 2-tert-butylphenylboronic acid, 4.0 g of potassium phosphate, 39 mL of toluene, and 3.9 mL of water were put in a three-neck flask equipped with a reflux pipe, and the air in the flask was replaced with nitrogen. In this container were added 48 mg of bis(dibenzylideneacetone)palladium(0), namely Pd₂(dba)₃, and 190 mg of tris(2,6-dimethoxyphenyl)phosphine, and heating was performed at 100° C. for 7 hours. Then, 24 mg of Pd₂(dba)₃ and 46 mg of tris(2,6-dimethoxyphenyl)phosphine were added and heating was performed at 100° C. for 17 hours. After that, 12 mg of palladium acetate and 44 mg of 2-dicyclohexylphosphino-2',6'-dimethoxybiphenyl (abbreviation: S-Phos) were added and heating was performed at 100° C. for 15 hours. Furthermore, 5.9 mg of palladium acetate and 27 mg of S-Phos (abbreviation) were added and heating was performed at 100° C. for 8 hours. Then, 0.10 g of 2-tert-butylphenylboronic acid, 2.0 g of potassium phosphate, 13 mg of palladium acetate, and 12 mg of S-Phos (abbreviation) were added and heating was performed at 100° C. for 21 hours. An organic layer was extracted from the obtained mixture with the use of ethyl acetate and was washed with saturated brine. Magnesium sulfate was added and the mixture was subjected to filtration. The solvent in the filtrate was distilled off to give a residue. The residue was purified by neutral silica gel column chromatography using a mixed solvent of ethyl acetate and hexane in a ratio of 1:4 as a developing solvent, so that 0.27 g of Hppm-tBup (abbreviation) that is an objective substance was obtained as a yellowish white solid in a yield of 18%. A synthesis scheme of Step 1 is shown in (b-1) below.

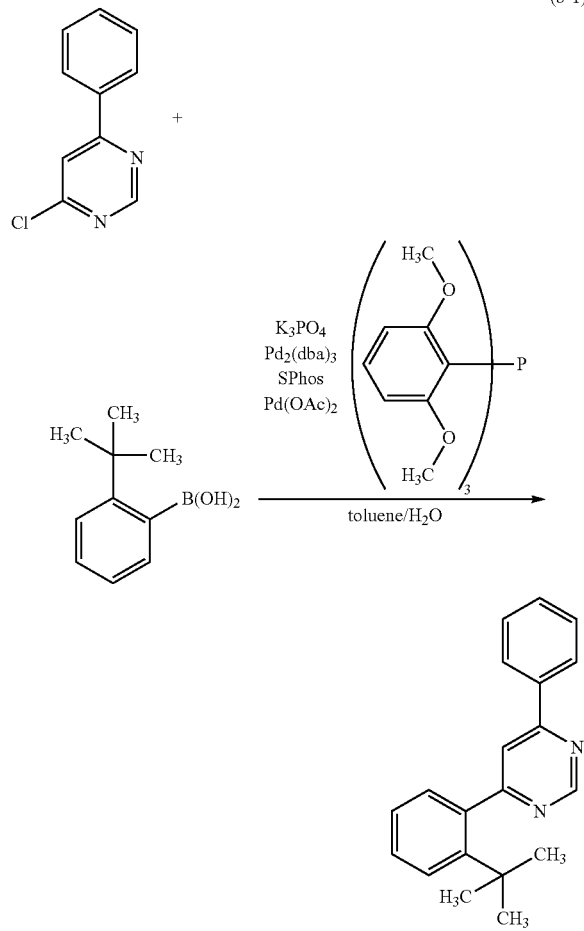

Step 2: Synthesis of di-μ-chloro-tetrakis{2-[6-(2-tert-butylphenyl)-4-pyrimidinyl-κN3]phenyl-κC}diiridium(III) (abbreviation: [Ir(ppm-tBup)$_2$Cl]$_2$)

Next, 0.27 g of Hppm-tBup (abbreviation) obtained by the synthesis method in Step 1, 0.14 g of iridium(III) chloride hydrate, 4.7 mL of 2-ethoxyethanol, and 1.6 mL of water were put in a round-bottom flask equipped with a reflux pipe, and the mixture was heated by being irradiated with microwaves (2.45 GHz, 100 W) for 20 minutes while being bubbled with argon. The resulting mixture was subjected to filtration and washing using hexane was performed; thus, 300 mg of [Ir(ppm-tBup)$_2$Cl]$_2$ (abbreviation) that is an objective substance was obtained as a dark orange solid in a yield of 80%. Note that the irradiation with microwaves was performed using a microwave synthesis system (Discover, manufactured by CEM Corporation). A synthesis scheme of Step 2 is shown in (b-2) below.

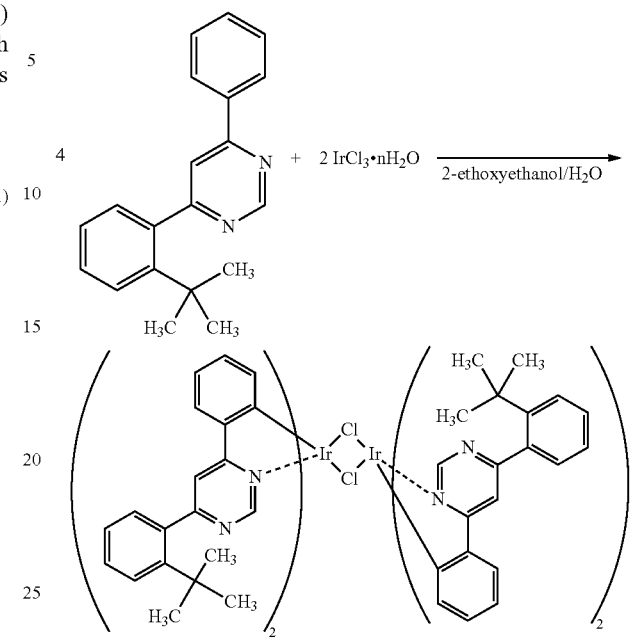

Step 3: Synthesis of bis{2-[6-(2-tert-butylphenyl)-4-pyrimidinyl-κN3]phenyl-κC}(2,4-pentanedionato-κ$^2$O,O')iridium(III) (abbreviation: Ir(ppm-tBup)$_2$(acac))

Next, 300 mg of [Ir(ppm-tBup)$_2$Cl]$_2$ (abbreviation) obtained in Step 2, 57 mg of acetylacetone (abbreviation: Hacac), 200 mg of sodium carbonate, and 2 mL of 2-ethoxyethanol were put in a flask, and the mixture was irradiated with microwaves (2.45 GHz, 80 W) for 7 minutes while being bubbled with argon. The solvent in the obtained mixture was distilled off, and the obtained residue was purified by flash column chromatography using a mixed solvent of ethyl acetate and hexane in a ratio of 1:5 as a developing solvent. The solvent was distilled off, and the obtained residue was purified by flash column chromatography (amine-modified silica gel) using a mixed solvent of ethyl acetate and hexane in a ratio of 1:5 as a developing solvent. Thus, Ir(ppm-tBup)$_2$(acac), which is the organometallic iridium complex of one embodiment of the present invention, was obtained as an orange powdered solid in a yield of 5%. A synthesis scheme of Step 3 is shown in (b-3) below.

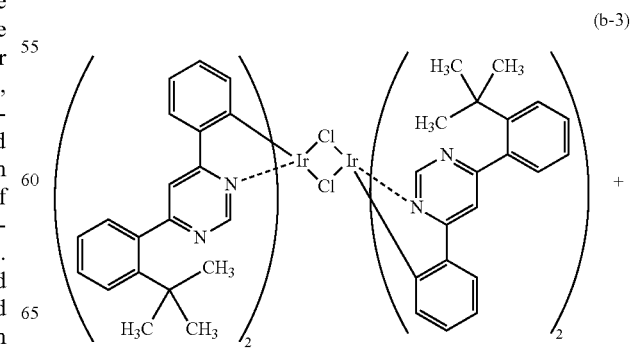

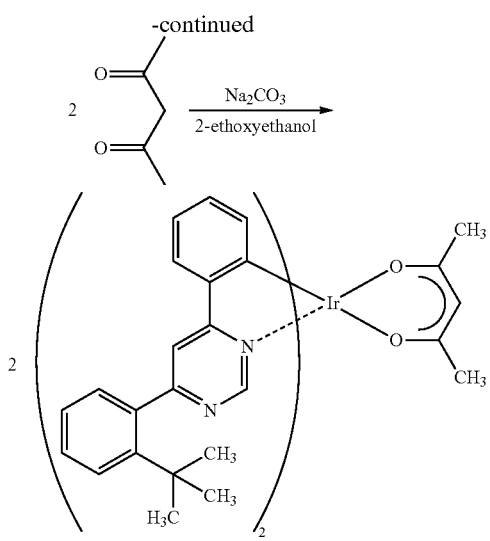

Figure 17:
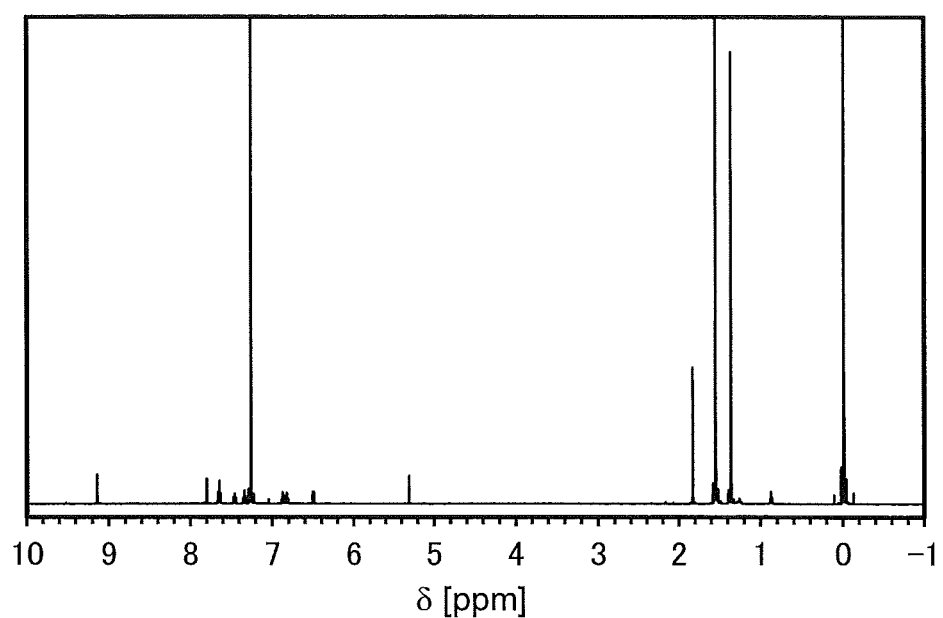
FIG. 17 shows a $^1$H-NMR chart of an organometallic iridium complex represented by Structural Formula (134).

An analysis result by nuclear magnetic resonance spectrometry ($^1$H-NMR) of the orange powdered solid obtained in Step 3 is described below. The $^1$H NMR chart is shown in FIG. 17. The results reveal that Ir(ppm-tBup)$_2$(acac), which is the organometallic complex of one embodiment of the present invention represented by Structural Formula (134), was obtained in this synthesis example. Note that the peaks observed at 0.88-0.89 and 1.25-1.29 in the $^1$H-NMR chart were derived from the hexane solvent.

$^1$H-NMR. δ (CDCl$_3$): 1.38 (s, 18H), 1.84 (s, 6H), 5.32 (s, 1H), 6.52 (d, 2H), 6.82-6.85 (dt, 2H), 6.87-6.90 (t, 2H), 7.29 (dd, 2H), 7.34-7.37 (dt, 2H), 7.45-7.49 (dt, 2H), 7.64-7.68 (dt, 4H), 7.82 (ds, 2H), 9.16 (ds, 2H).

Figure 18:
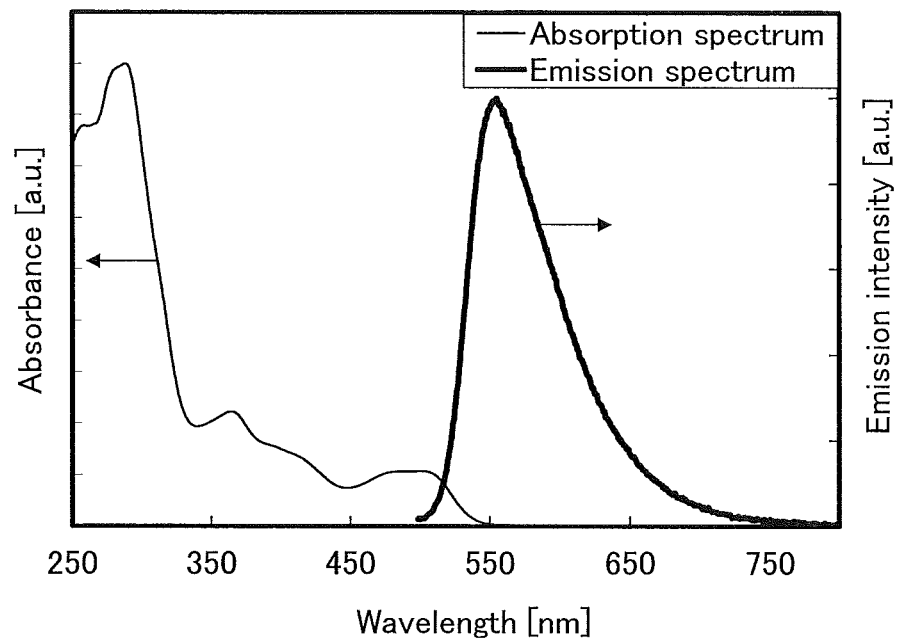
FIG. 18 shows an ultraviolet-visible absorption spectrum and an emission spectrum of an organometallic iridium complex represented by Structural Formula (134).

Next, an absorption spectrum and an emission spectrum of a deoxidized dichloromethane solution of Ir(ppm-tBup)$_2$(acac) were measured. The measurement of the absorption spectrum was conducted at room temperature, for which an ultraviolet-visible light spectrophotometer (V550 type manufactured by Japan Spectroscopy Corporation) was used and the dichloromethane solution (0.011 mmol/L) was put in a quartz cell. In addition, the measurement of the emission spectrum was conducted at room temperature, for which an absolute PL quantum yield measurement system (C11347-01 manufactured by Hamamatsu Photonics K. K.) was used. The deoxidized dichloromethane solution (0.011 mmol/L) was sealed in a quartz cell under a nitrogen atmosphere in a glove box (LABstar M13 (1250/780)) manufactured by Bright Co., Ltd. Measurement results of the obtained absorption and emission spectra are shown in FIG. 18, in which the horizontal axis represents wavelength and the vertical axes represent absorption intensity and emission intensity. In FIG. 18 where there are two solid lines, the thin line represents the absorption spectrum and the thick line represents the emission spectrum. Note that the absorption spectrum in FIG. 18 is the results obtained in such a way that the absorption spectrum measured by putting only dichloromethane in a quartz cell was subtracted from the absorption spectrum measured by putting the dichloromethane solution (0.011 mmol/L) in a quartz cell.

As shown in FIG. 18, Ir(ppm-tBup)$_2$(acac), the organometallic complex of one embodiment of the present invention, has an emission peak at 553 nm, and yellow light emission was observed from the dichloromethane solution.

Note that the structure described in this example can be combined as appropriate with any of the structures described in other embodiments and examples.

EXAMPLE 3

In this example, a light-emitting element 1, a comparative light-emitting element 2, and a comparative light-emitting element 3 were fabricated, and characteristics of these elements were measured. Light-emitting layers of the light-emitting element 1, the comparative light-emitting element 2, and the comparative light-emitting element 3 were respectively formed using Ir(ppm-dmp)$_2$(acac) (Structural Formula (100)) that is the organometallic iridium complex of one embodiment of the present invention synthesized in Example 1, (acetylacetonato)bis[5-methyl-6-(2-methylphenyl)-4-phenylpyrimidinato]iridium(III) (another name: bis{2-[5-methyl-6-(2-methylphenyl)-4-pyrimidinyl-κN3]phenyl-κC}(2,4-pentanedionato-κ$^2$O,O')iridium(III)) (abbreviation: Ir(mpmppm)$_2$(acac)) (Structural Formula (502)) that is a comparative organometallic iridium complex, and (acetylacetonato)bis(4,6-diphenylpyrimidinato)iridium(III) (abbreviation: Ir(dppm)$_2$(acac)) (Structural Formula (500)) that is a comparative organometallic iridium complex. Chemical formulae of materials used in this example are shown below.

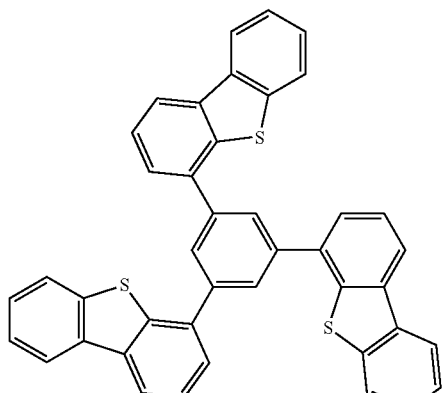

DBT3P-II

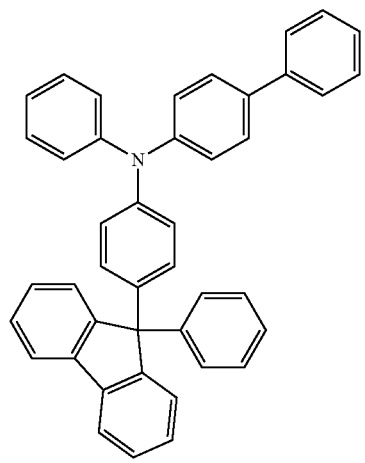

BPAFLP

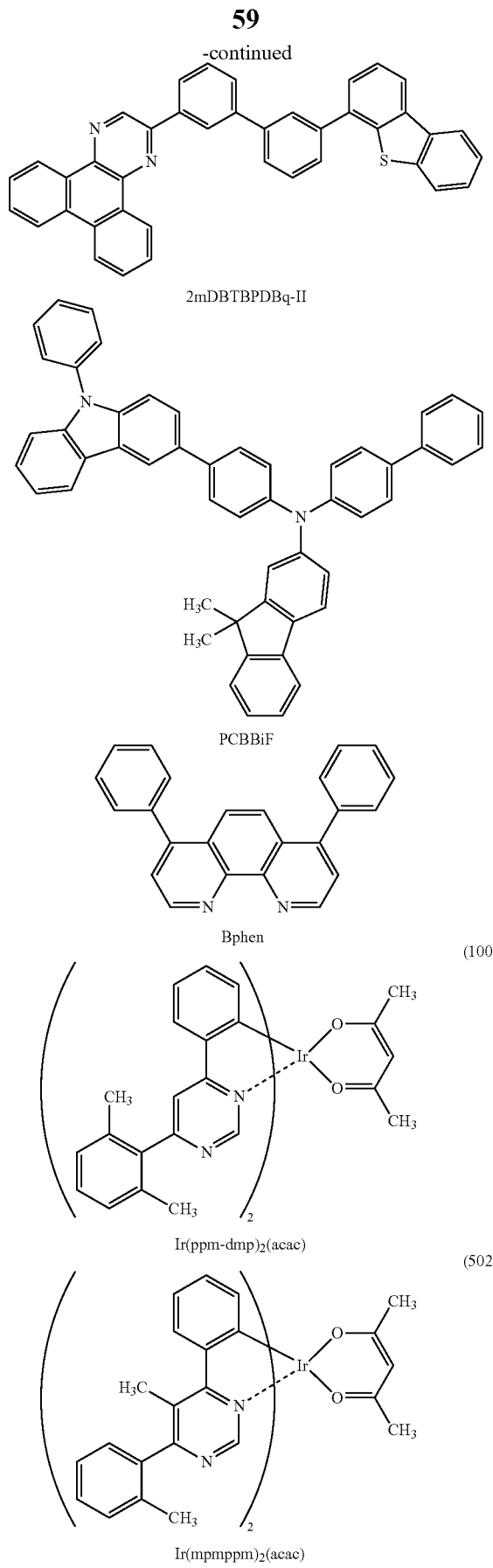
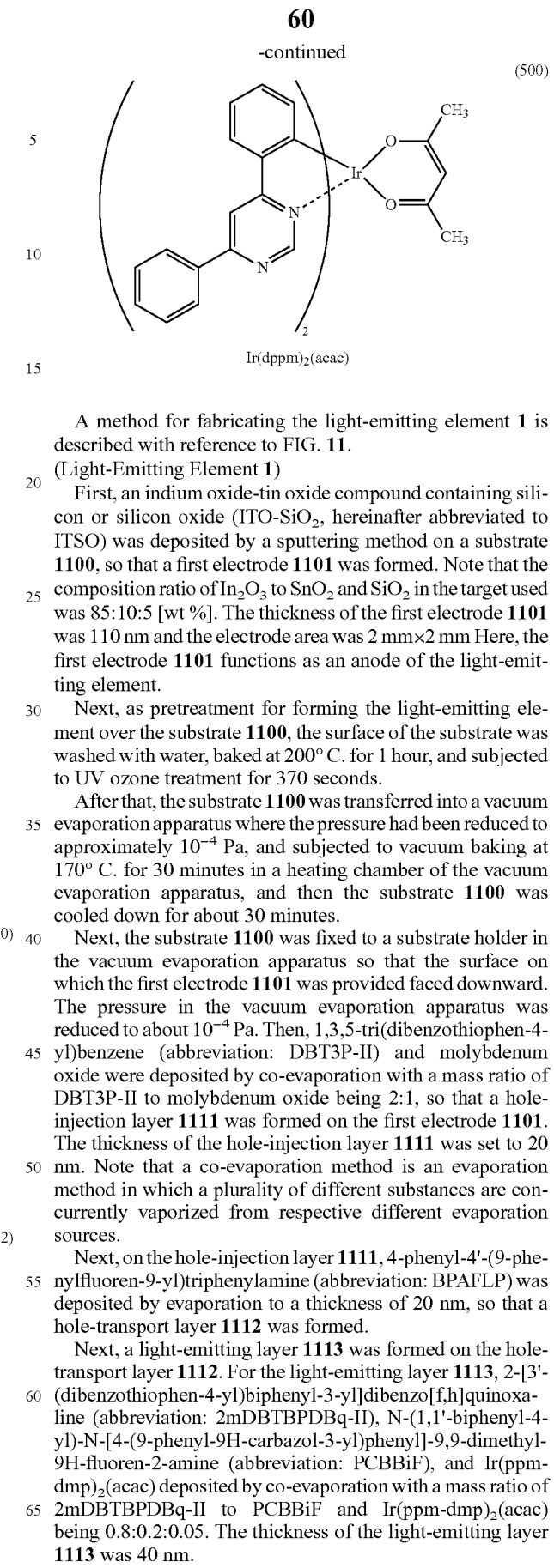

Figure 11:
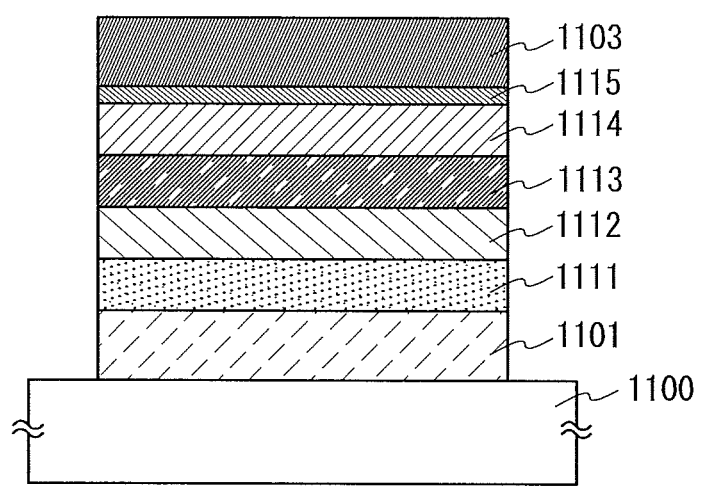
FIG. 11 illustrates a light-emitting element.

A method for fabricating the light-emitting element 1 is described with reference to FIG. 11.

(Light-Emitting Element 1)

First, an indium oxide-tin oxide compound containing silicon or silicon oxide (ITO-SiO$_2$, hereinafter abbreviated to ITSO) was deposited by a sputtering method on a substrate 1100, so that a first electrode 1101 was formed. Note that the composition ratio of In$_2$O$_3$ to SnO$_2$ and SiO$_2$ in the target used was 85:10:5 [wt %]. The thickness of the first electrode 1101 was 110 nm and the electrode area was 2 mm×2 mm Here, the first electrode 1101 functions as an anode of the light-emitting element.

Next, as pretreatment for forming the light-emitting element over the substrate 1100, the surface of the substrate was washed with water, baked at 200° C. for 1 hour, and subjected to UV ozone treatment for 370 seconds.

After that, the substrate 1100 was transferred into a vacuum evaporation apparatus where the pressure had been reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in the vacuum evaporation apparatus so that the surface on which the first electrode 1101 was provided faced downward. The pressure in the vacuum evaporation apparatus was reduced to about 10$^{-4}$ Pa. Then, 1,3,5-tri(dibenzothiophen-4-yl)benzene (abbreviation: DBT3P-II) and molybdenum oxide were deposited by co-evaporation with a mass ratio of DBT3P-II to molybdenum oxide being 2:1, so that a hole-injection layer 1111 was formed on the first electrode 1101. The thickness of the hole-injection layer 1111 was set to 20 nm. Note that a co-evaporation method is an evaporation method in which a plurality of different substances are concurrently vaporized from respective different evaporation sources.

Next, on the hole-injection layer 1111, 4-phenyl-4'-(9-phenylfluoren-9-yl)triphenylamine (abbreviation: BPAFLP) was deposited by evaporation to a thickness of 20 nm, so that a hole-transport layer 1112 was formed.

Next, a light-emitting layer 1113 was formed on the hole-transport layer 1112. For the light-emitting layer 1113, 2-[3'-(dibenzothiophen-4-yl)biphenyl-3-yl]dibenzo[f,h]quinoxaline (abbreviation: 2mDBTBPDBq-II), N-(1,1'-biphenyl-4-yl)-N-[4-(9-phenyl-9H-carbazol-3-yl)phenyl]-9,9-dimethyl-9H-fluoren-2-amine (abbreviation: PCBBiF), and Ir(ppm-dmp)$_2$(acac) deposited by co-evaporation with a mass ratio of 2mDBTBPDBq-II to PCBBiF and Ir(ppm-dmp)$_2$(acac) being 0.8:0.2:0.05. The thickness of the light-emitting layer 1113 was 40 nm.

Note that in the light-emitting layer 1113 of the light-emitting element 1, 2mDBTBPDBq-II served as a host material, PCBBiF served as a secondary host material, and Ir(ppm-dmp)$_2$(acac) served as a guest material (dopant).

Then, on the light-emitting layer 1113, 2mDBTBPDBq-II was deposited by evaporation to a thickness of 15 nm and then bathophenanthroline (abbreviation: Bphen) was deposited by evaporation to a thickness of 10 nm, whereby an electron-transport layer 1114 was formed. Furthermore, lithium fluoride was deposited by evaporation to a thickness of 1 nm on the electron-transport layer 1114, whereby an electron-injection layer 1115 was formed.

Finally, aluminum was deposited by evaporation to a thickness of 200 nm on the electron-injection layer 1115, whereby a second electrode 1103 serving as a cathode was formed. Through the above-described steps, the light-emitting element 1 was fabricated.

thickness of 20 nm with a mass ratio of 2mDBTBPDBq-II to PCBBiF and Ir(dppm)$_2$(acac) being 0.7:0.3:0.05.

Note that in the light-emitting layer 1113 of the comparative light-emitting element 3, 2mDBTBPDBq-II served as a host material, PCBBiF served as an assist material, and Ir(dppm)$_2$(acac) served as a guest material (dopant).

Note that in all the above evaporation steps, evaporation was performed by a resistance-heating method.

Since the light-emitting element 1, the comparative light-emitting element 2, and the comparative light-emitting element 3 use the respective guest materials (dopants), the structure of the light-emitting layer 1113 and the electron-transport layer 1114 were optimized Table 2 shows element structures of the light-emitting element 1, the comparative light-emitting element 2, and the comparative light-emitting element 3 formed as described above.

TABLE 2

| | First electrode | Hole-injeciton layer | Hole-transport layer | Light-emitting layer | Electron-transport layer | | Electron-injection layer | Second electrode |
|---|---|---|---|---|---|---|---|---|
| Light-emitting element 1 | ITSO (110 nm) | DBT3P-II:MoO$_x$ (2:1 20 nm) | BPAFLP (20 nm) | *1) | 2mDBTBPDBq-II (15 nm) | Bphen (10 nm) | LiF (1 nm) | Al (200 nm) |
| Comparative light-emitting element 2 | ITSO (110 nm) | DBT3P-n:MoO$_x$ (2:1 20 nm) | BPAFLP (20 nm) | *2) | 2mDBTBPDBq-II (15 nm) | Bphen (10 nm) | LiF (1 nm) | Al (200 nm) |
| Comparative light-emitting element 3 | ITSO (110 nm) | DBT3P-II:MoO$_x$ (2:1 20 nm) | BPAFLP (20 nm) | *3) | 2mDBTBPDBq-II (20 nm) | Bphen (10 nm) | LiF (1 nm) | Al (200 nm) |

*1) 2mDBTBPDBq-II:PCBBiF:Ir(ppm-dmp)$_2$(acac) (0.8:0.2:0.05 40 nm)
*2) 2mDBTBPDBq-II:PCBBiF:Ir(mpmppm)$_2$(acac) (0.8:0.2:0.05 40 nm)
*3) 2mDBTBPDBq-II:PCBBiF:Ir(dppm)$_2$(acac)\2mDBTBPDBq-II:PCBBiF:Ir(dppm)$_2$(acac) ((0.7:0.3:0.05 20 nm)\(0.8:0.2:0.05 20 nm))

Next, methods for fabricating the comparative light-emitting elements 2 and 3 are described.
(Comparative Light-Emitting Element 2)

The comparative light-emitting element 2 is different from the light-emitting element 1 in the structure of the light-emitting layer 1113. Only the structure different from the light-emitting element 1 is described below.

For the light-emitting layer 1113, 2mDBTBPDBq-II, PCBBiF, and bis{2-[5-methyl-6-(2-methylphenyl)-4-pyrimidinyl-κN3]phenyl-κC}(2,4-pentanedionato-κ$^2$O,O')iridium(III) (abbreviation: Ir(mpmppm)$_2$(acac)) deposited by co-evaporation with a mass ratio of 2mDBTBPDBq-II to PCBBiF and Ir(mpmppm)$_2$(acac) being 0.8:0.2:0.05. The thickness of the light-emitting layer 1113 was 40 nm.

Note that in the light-emitting layer 1113 of the comparative light-emitting element 2, 2mDBTBPDBq-II served as a host material, PCBBiF served as an assist material, and Ir(mpmppm)$_2$(acac) served as a guest material (dopant).
(Comparative Light-Emitting Element 3)

The comparative light-emitting element 3 is different from the light-emitting element 1 in the structures of the light-emitting layer 1113 and the electron-transport layer 1114. Only the structures different from the light-emitting element 1 are described below.

For the light-emitting layer 1113, 2mDBTBPDBq-II, PCBBiF, and (acetylacetonato)bis(4,6-diphenylpyrimidinato)iridium(III) (abbreviation: Ir(dppm)$_2$(acac)) were deposited by co-evaporation to a thickness of 20 nm with a mass ratio of 2mDBTBPDBq-II to PCBBiF and Ir(dppm)$_2$(acac) being 0.7:0.3:0.05; then, 2mDBTBPDBq-II, PCBBiF, and Ir(dppm)$_2$(acac) were deposited by co-evaporation to a Then, in a glove box containing a nitrogen atmosphere, the light-emitting element 1, the comparative light-emitting element 2, and the comparative light-emitting element 3 were sealed so as not to be exposed to the air (specifically, a sealant was applied onto an outer edge of the elements and heat treatment was performed at 80° C. for 1 hour at the time of sealing). After that, the operating characteristics of the light-emitting element 1, the comparative light-emitting element 2, and the comparative light-emitting element 3 were measured. Note that the measurement was carried out at room temperature (kept at 25° C.).

Figure 12:
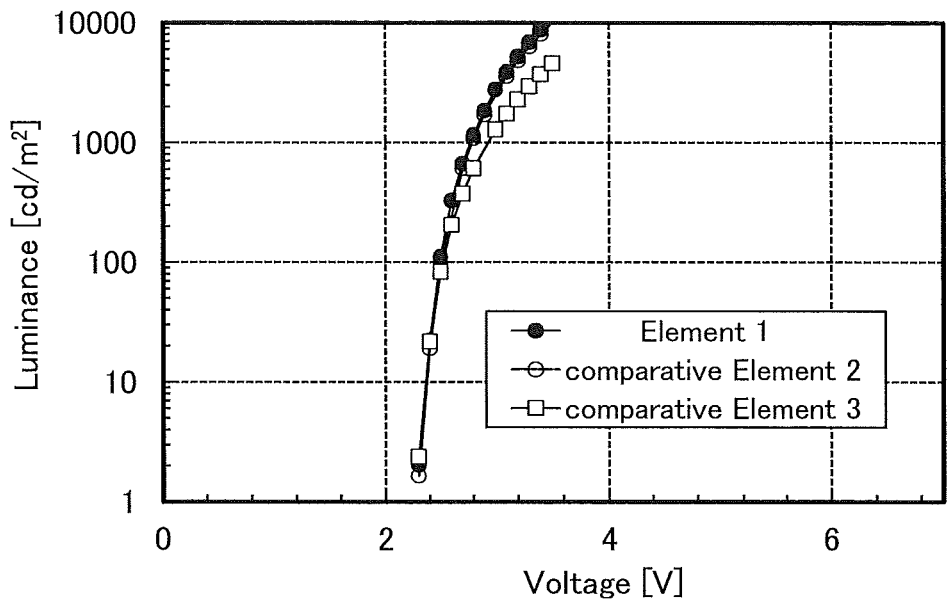
FIG. 12 shows voltage-luminance characteristics of a light-emitting element 1, a comparative light-emitting element 2, and a comparative light-emitting element 3.
Figure 13:
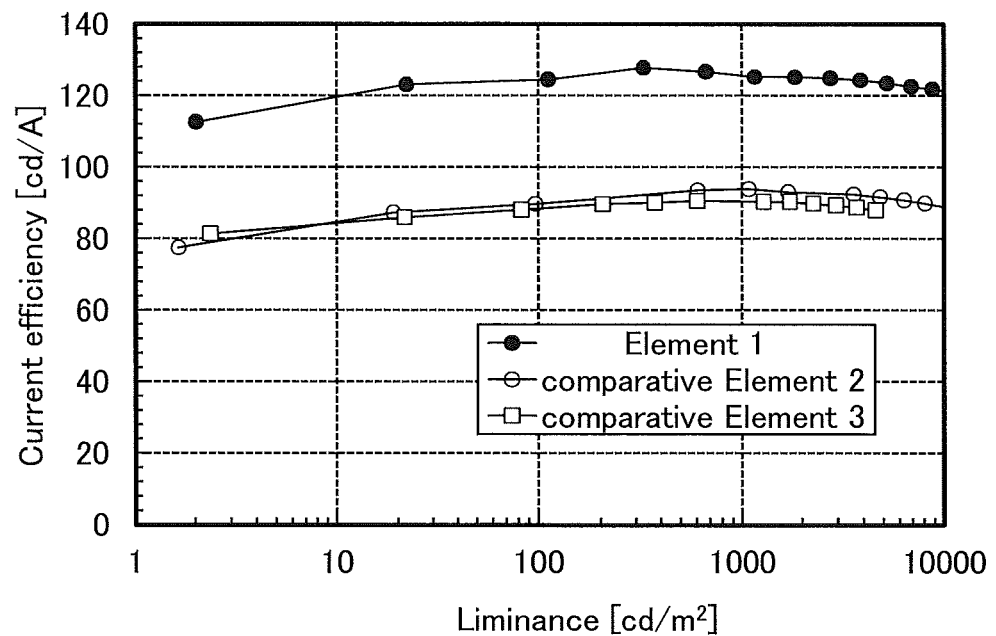
FIG. 13 shows luminance-current efficiency characteristics of a light-emitting element 1, a comparative light-emitting element 2, and a comparative light-emitting element 3.
Figure 14:
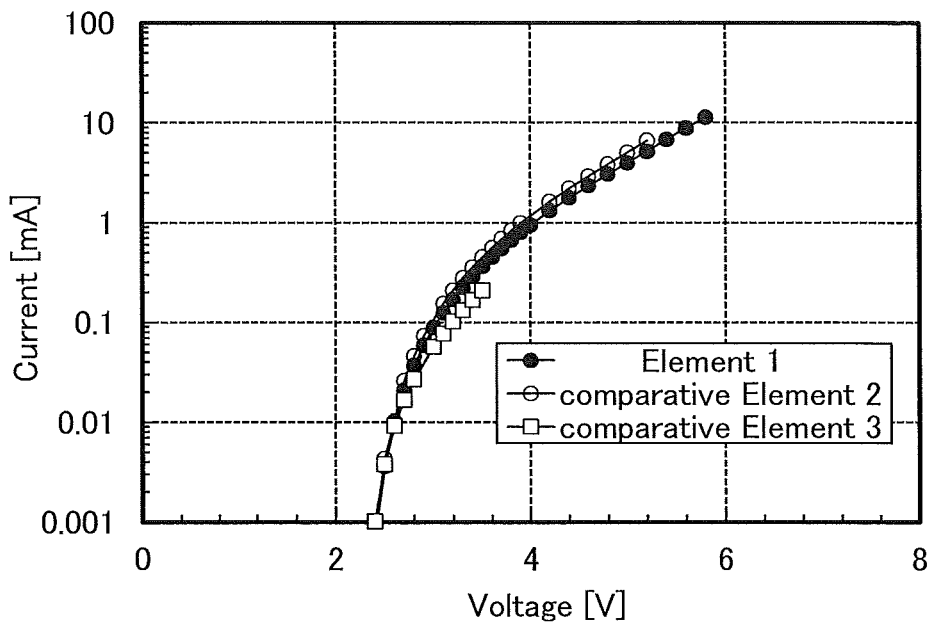
FIG. 14 shows voltage-current characteristics of a light-emitting element 1, a comparative light-emitting element 2, and a comparative light-emitting element 3.
Figure 15:
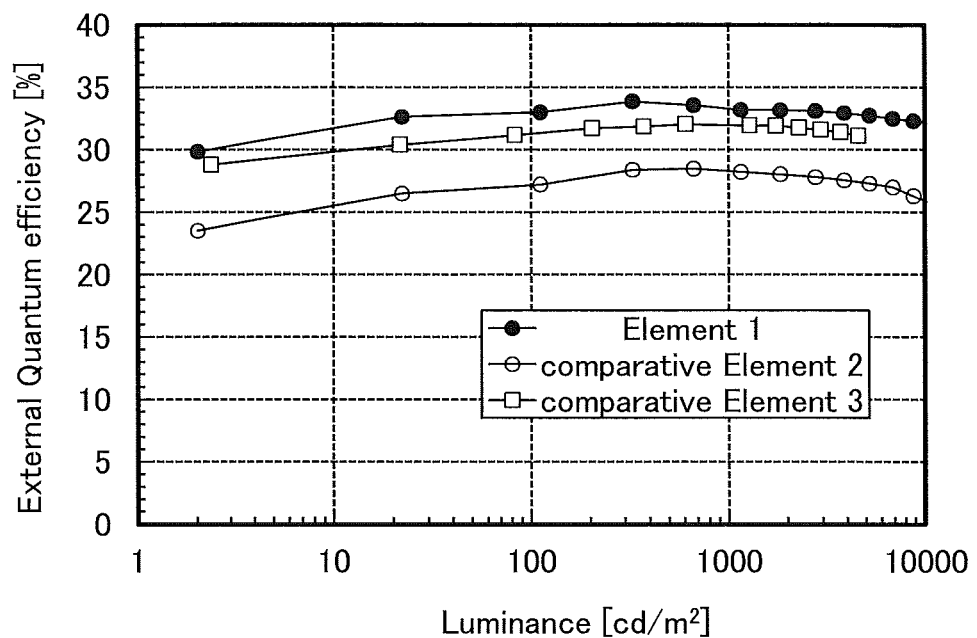
FIG. 15 shows luminance-external quantum efficiency characteristics of a light-emitting element 1, a comparative light-emitting element 2, and a comparative light-emitting element 3.

FIG. 12 shows voltage-luminance characteristics of the light-emitting element 1, the comparative light-emitting element 2, and the comparative light-emitting element 3. In FIG. 12, the horizontal axis represents voltage (V) and the vertical axis represents luminance (cd/m$^2$). Further, FIG. 13 shows luminance-current efficiency characteristics of the light-emitting element 1, the comparative light-emitting element 2, and the comparative light-emitting element 3. In FIG. 13, the horizontal axis represents luminance (cd/m$^2$) and the vertical axis represents current efficiency (cd/A). FIG. 14 shows voltage-current characteristics of the light-emitting element 1, the comparative light-emitting element 2, and the comparative light-emitting element 3. In FIG. 14, the horizontal axis represents voltage (V) and the vertical axis represents current (mA). FIG. 15 shows luminance-external quantum efficiency characteristics of the light-emitting element 1, the comparative light-emitting element 2, and the comparative light-emit ting element 3. In FIG. 15, the horizontal axis represents luminance (cd/m²) and the vertical axis represents external quantum efficiency (%).

The results in FIG. 13 and FIG. 15 show that the light-emitting element 1 of one embodiment of the present invention has higher current efficiency and external quantum efficiency than the comparative light-emitting element 2 and the comparative light-emitting element 3.

Table 3 shows the characteristics of the light-emitting element 1, the comparative light-emitting element 2, and the comparative light-emitting element 3.

TABLE 3

|  | Voltage (V) | Current (mA) | Current density (mA/cm²) | CIA chromaticity coordinates (x, y) | Luminance (cd/m²) | Current efficiency (cd/A) | Power efficiency (lm/W) | External quantum efficiency (%) |
|---|---|---|---|---|---|---|---|---|
| Light-emitting element 1 | 2.8 | 0.037 | 0.9 | (0.44, 0.55) | 1200 | 130 | 140 | 33 |
| Comparative light-emitting element 2 | 2.8 | 0.046 | 1.2 | (0.49, 0.50) | 1100 | 94 | 110 | 28 |
| Comparative light-emitting element 3 | 2.8 | 0.027 | 0.7 | (0.55, 0.45) | 607 | 91 | 102 | 32 |

Figure 16:
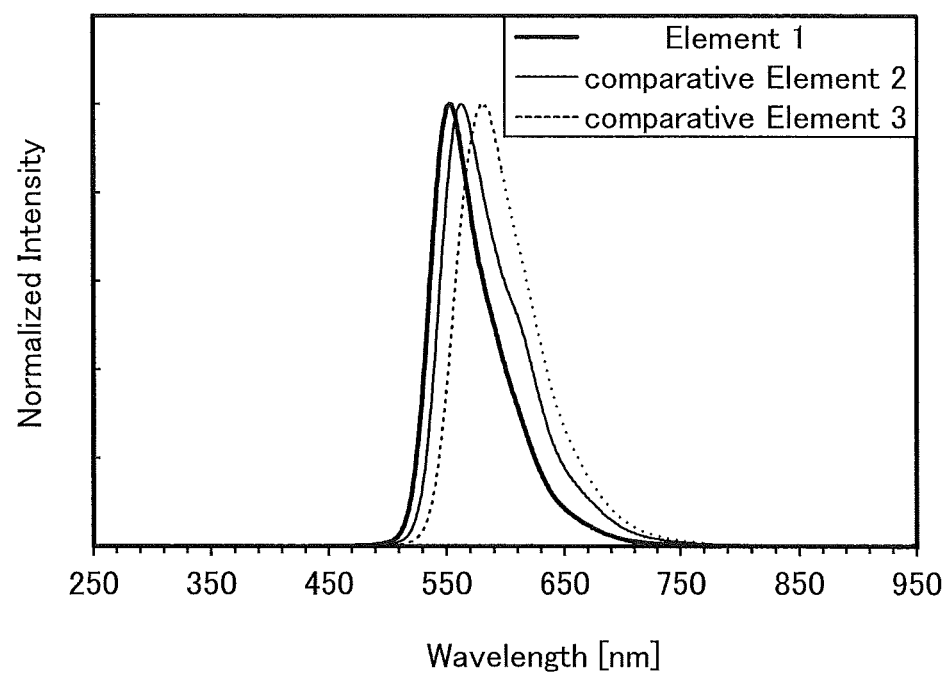
FIG. 16 shows emission spectra of a light-emitting element 1, a comparative light-emitting element 2, and a comparative light-emitting element 3.

FIG. 16 shows emission spectra of the light-emitting element 1, the comparative light-emitting element 2, and the comparative light-emitting element 3 when current was supplied thereto at a current density of 2.5 mA/cm². As shown in FIG. 16, the emission spectra of the light-emitting element 1, the comparative light-emitting element 2, and the comparative light-emitting element 3 have peaks at 553 nm, 563 nm, and 579 nm, respectively.

From the CIE chromaticity coordinates (x, y) in Table 3 and the emission spectra in FIG. 16, it was found that the light-emitting element 1, the comparative light-emitting element 2, and the comparative light-emitting element 3 emit light derived from the dopants.

The above-described results show that the emission spectrum of the light-emitting element 1 of one embodiment of the present invention is located on a shorter wavelength side than the emission spectrum of the comparative light-emitting element 2 and that of the comparative light-emitting element 3. Because the emission spectrum of the light-emitting element 1 peaks at 553 nm, light emitted from the light-emitting element 1 has a higher luminosity factor than light emitted from the comparative light-emitting element 2 and light emitted from the comparative light-emitting element 3. It is also shown that the light-emitting element 1 of one embodiment of the present invention has high luminance and exhibits favorable current efficiency characteristics. Moreover, it can be found that the light-emitting element 1 emits yellow light with excellent color purity.

Calculation of the dihedral angle between the pyrimidine ring and the phenyl group at the 6-position of the pyrimidine ring was performed on Ir(ppm-dmp)$_2$(acac), Ir(mpmppm)$_2$(acac), and Ir(dppm)$_2$(acac) that were used as the light-emitting substances in the light-emitting element 1, the comparative light-emitting element 2, and the comparative light-emitting element 3, respectively.

The calculation device and method that are described in Embodiment 1 were used.

The results of calculation are shown in Table 4.

TABLE 4

| Material | Dihedral angle (°) | Element |
|---|---|---|
| Ir(ppm-dmp)$_2$(acac) | 70 | Light-emitting element 1 |
| Ir(mpmppm)$_2$(acac) | 64 | Comparative light-emitting element 2 |
| Ir(dppm)$_2$(acac) | 18 | Comparative light-emitting element 3 |

As shown in Table 4, the dihedral angle between the pyrimidine ring and the phenyl group at the 6-position of the pyrimidine ring is larger in Ir(ppm-dmp)$_2$(acac), which was used in the light-emitting element 1 of one embodiment of the present invention, than in Ir(mpmppm)$_2$(acac) and Ir(dppm)$_2$(acac), which were respectively used in the comparative light-emitting element 2 and the comparative light-emitting element 3. Consequently, in the organometallic iridium complex of one embodiment of the present invention, a twist is formed owing to steric hindrance and extension of π-conjugation thus can be inhibited.

Note that the structure described in this example can be combined as appropriate with any of the structures described in other embodiments and examples.

REFERENCE NUMERALS

101: first electrode, 102: EL layer, 103: second electrode, 111: hole-injection layer, 112: hole-transport layer, 113: light-emitting layer, 114: electron-transport layer, 115: electron-injection layer, 116: charge generation layer, 201: first electrode, 202: second electrode, 203: EL layer, 204: light-emitting layer, 205: phosphorescent compound, 206: first organic compound, 207: second organic compound, 210: first layer, 212: second layer, 301: first electrode, 302: EL layer, 304: second electrode, 305: charge generation layer, 401: element substrate, 402: pixel portion, 403: driver circuit portion, 404a: driver circuit portion, 404b: driver circuit portion, 405: sealant, 406: sealing substrate, 407: lead wiring, 408: FPC, 409: FET, 410: FET, 411: FET, 412: FET, 413: first electrode, 414: insulator, 415: EL layer, 416: second electrode, 417: light-emitting element, 418: space, 1100: substrate, 1101: first electrode, 1103: second electrode, 1111: hole-injection layer, 1112: hole-transport layer, 1113: light-emitting layer, 1114: electron-transport layer, 1115: electron-injection layer, 7100: television set, 7101: housing, 7103:

display portion, 7105: stand, 7107: display portion, 7109: operation key, 7110: remote controller, 7201: main body, 7202: housing, 7203: display portion, 7204: keyboard, 7205: external connection port, 7206: pointing device, 7302: housing, 7304: display panel, 7305: icon, 7306: icon, 7311: operation button, 7312: operation button, 7313: connection terminal, 7321: band, 7322: clasp, 7400: mobile phone, 7401: housing, 7402: display portion, 7403: button, 7404: external connection portion, 7405: speaker, 7406: microphone, 7407: camera, 8001: lighting device, 8002: lighting device, 8003: lighting device, 8004: lighting device, 8100: mobile phone, 8102: housing, 8104: display portion, 8106: camera, and 8108: illumination device.

This application is based on Japanese Patent Application serial no. 2013-189385 filed with Japan Patent Office on Sep. 12, 2013, the entire contents of which are hereby incorporated by reference.

The invention claimed is:

1. A compound represented by Formula (G5):

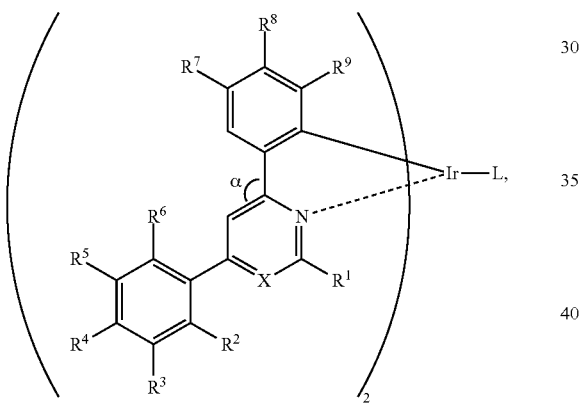

(G5)

wherein:

$R^1$ to $R^9$ independently represent hydrogen or an unsubstituted alkyl group having 1 to 6 carbon atoms;

at least one of $R^2$ and $R^6$ represents a tert-butyl group;

X represents a nitrogen atom;

L represents a monoanionic ligand;

the monoanionic ligand is represented by any one of Formulae (L1) to (L7):

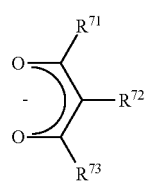

(L1)

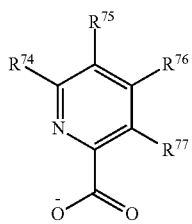

(L2)

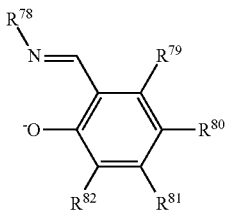

(L3)

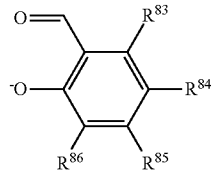

(L4)

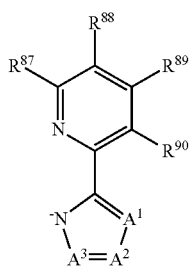

(L5)

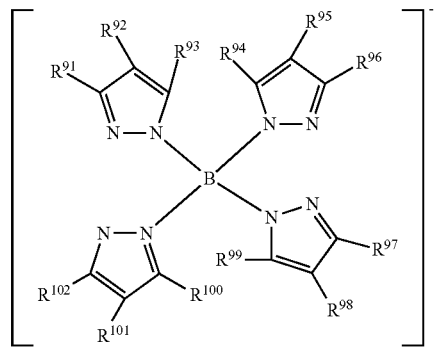

(L6)

-continued

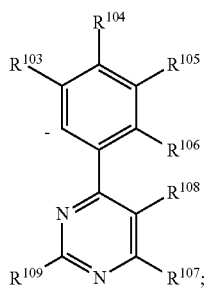
(L7)

$R^{71}$ to $R^{109}$ independently represent any one of hydrogen, an alkyl group having 1 to 6 carbon atoms, a halogen, a vinyl group, a haloalkyl group having 1 to 6 carbon atoms, an alkoxy group having 1 to 6 carbon atoms, and an alkylthio group having 1 to 6 carbon atoms;

$A^1$ to $A^3$ independently represent any one of nitrogen and carbon bonded to hydrogen or to a substituent R;

the substituent R is any one of an alkyl group having 1 to 6 carbon atoms, a halogen, a haloalkyl group having 1 to 6 carbon atoms, and a phenyl group;

when X represents the nitrogen atom, the other of $R^2$ and $R^6$ represents hydrogen, or one of $R^1$, $R^3$ to $R^5$ and $R^7$ to $R^9$ represents an unsubstituted alkyl group having 1 to 6 carbon atoms, a dihedral angle between a ring bonded to $R^1$ and a phenyl group bonded to $R^2$ to $R^6$ is greater than or equal to 30° and less than or equal to 90°;

a dihedral angle between the ring bonded to $R^7$ to $R^9$ is greater than or equal to 0° and less than 2°; and a bond angle denoted by α is greater than or equal to 120° and less than 129°.

2. The compound according to claim 1, wherein $R^3$ to $R^5$ represent hydrogen.

3. The compound according to claim 1, wherein $R^1$ represents hydrogen.

4. The compound according to claim 1, wherein one of $R^2$ and $R^6$ represents hydrogen.

5. A compound represented by Formula (G6):

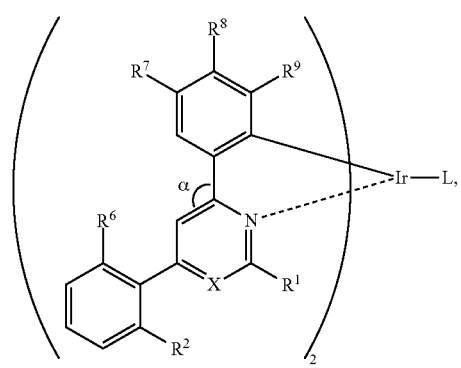
(G6)

wherein:
$R^1$, $R^2$ and $R^6$ to $R^9$ independently represent hydrogen or an unsubstituted alkyl group having 1 to 6 carbon atoms;
one of $R^2$ and $R^6$ represents an alkyl group having 1 to 6 carbon atoms;

the other one of $R^2$ and $R^6$ represents hydrogen;

X represents a nitrogen atom;

the monoanionic ligand is represented by any one of Formulae (L1) to (L7):

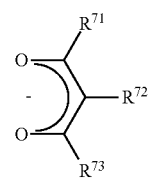
(L1)

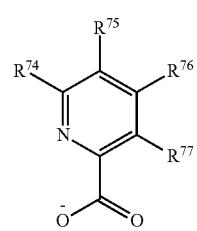
(L2)

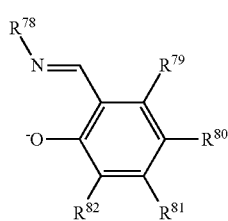
(L3)

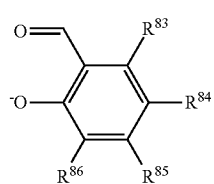
(L4)

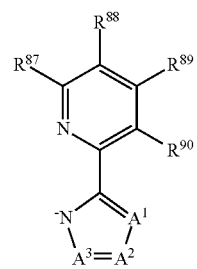
(L5)

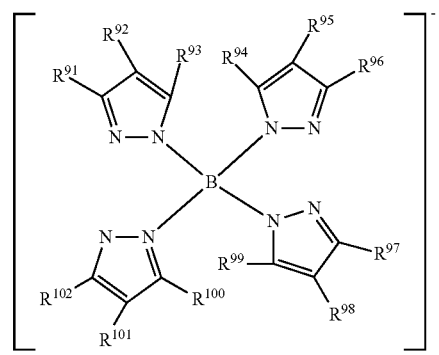
(L6)

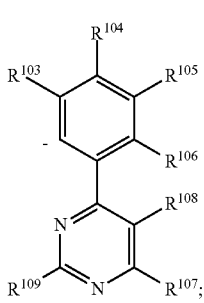

(L7)

$R^{71}$ to $R^{109}$ independently represent any one of hydrogen, a substituted or unsubstituted alkyl group having 1 to 6 carbon atoms, a halogen, a vinyl group, a substituted or unsubstituted haloalkyl group having 1 to 6 carbon atoms, a substituted or unsubstituted alkoxy group having 1to 6 carbon atoms, and a substituted or unsubstituted alkylthio group having 1 to 6 carbon atoms;

$A^1$ to $A^3$ independently represent any one of nitrogen and carbon bonded to hydrogen or to a substituent R;

the substituent R is any one of an alkyl group having 1 to 6 carbon atoms, a halogen, a haloalkyl group having 1 to 6 carbon atoms, and a phenyl group;

L represents a monoanionic ligand, wherein a dihedral angle between a ring bonded to $R^1$ and a phenyl group bonded to $R^2$ to $R^6$ is greater than or equal to 30° and less than or equal to 90°;

wherein a dihedral angle between the ring bonded to $R^1$ and a phenyl group bonded to $R^7$ to $R^9$ is greater than or equal to 0° and less than 2°; and a bond angle denoted by α is greater than or equal to 120° and less than 129°.

6. The compound according to claim 5, wherein the compound is represented by Formula (134):

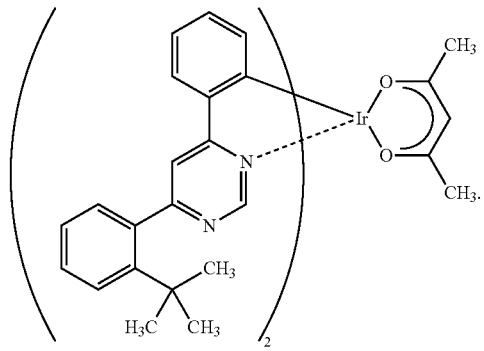

(134)

7. A light-emitting device comprising the compound according to claim 5.

8. A lighting device comprising the compound according to claim 5.

9. An electronic device comprising the light-emitting device according to claim 7.

* * * * *